(12) United States Patent
Karn et al.

(10) Patent No.: US 6,316,194 B1
(45) Date of Patent: Nov. 13, 2001

(54) METHODS AND KITS FOR DISCOVERY OF RNA-BINDING ANTIMICROBIALS

(75) Inventors: Jonathan Karn, Little Shelford; David Justin Charles Knowles, Boroughbridge York; Alastair Iain Hamilton Murchie; Georg Friedrich Lentzen, both of Cambridge, all of (GB)

(73) Assignee: Ribotargets, London (GB)

( * ) Notice: Subject to any disclaimer, the term of this patent is extended or adjusted under 35 U.S.C. 154(b) by 0 days.

(21) Appl. No.: 09/465,355

(22) Filed: Dec. 16, 1999

(51) Int. Cl.⁷ .............. C12Q 1/68; C07G 11/00; C07H 21/02
(52) U.S. Cl. .............. 435/6; 536/16.8; 536/23.1
(58) Field of Search ............ 435/6, 810; 536/23.1, 536/16.8

(56) References Cited

U.S. PATENT DOCUMENTS

| | | | |
|---|---|---|---|
| 4,257,774 | 3/1981 | Richardson et al. | 23/230 B |
| 5,445,935 | 8/1995 | Royer | 435/6 |
| 5,593,835 | * 1/1997 | Rando et al. | 435/6 |
| 5,712,096 | * 1/1998 | Stern et al. | 435/6 |
| 5,783,431 | * 7/1998 | Peterson et al. | 435/172.3 |

OTHER PUBLICATIONS

Zhang, J. et al. J. Biol. Chem. 275(44):34314–34319 [Nov. 2000]).*
Grainger, R.J. et al. J. Mol. Biol. 288:585–594 [May 1999]).*
Ha, T. et al. Proc. Natl. Acad. Sci. USA 96:9077–9082 [Aug. 1999]).*
Furey, W.S. et al. Biochemistry 37(9):2979–2990, May 1998.*
Aboul-ela, F., Karn, J. & Varani, G. (1995) J. Mol. Biol., 253, 313–332.
Brodsky, A.S. & Williamson, J. R. (1997) J. Mol. Biol., 267, 624–639.
Cai, A., Gorin, A., Federick R., Ye, X., Hu, W., Majumdar, A., Kettani, A. & Patel, D.J. (1998). Nature Struct. Biol., 5, 203–212.
DeGuzman, R.N., Wu, Z. R., Stalling, C.C., Pappalardo, L. Borer, P.N. & Summers, M.F. (1998). Science, 279, 384–388.
Metzger, U.A., Bayer, P., Willbold, D., Hoffmann, S., Frank, R.W., Goody, R.S. & Rösch, P. (1997). Biochem. Biophys. Res. Comm., 241, 31–36.
Puglisi, J.D., Tan. R., Calnan, B.J., Frankel, A.D. & Williamson, J.R. (1992). Science, 257, 76–80.
Selvin P.R. (1995) Mehtods Enzymol. 246, 300–335.
Stryer, L. (1978) Ann. Rev. Biochem. 47, 819–846.
Wang, J. Hamasaki, K. & Rando, R.R. (1997). Biochemistry, 36, 768–779.

* cited by examiner

Primary Examiner—Carla A. Myers
Assistant Examiner—Diana Johannsen
(74) Attorney, Agent, or Firm—Kathleen Williams; Palmer & Dodge, LLP

(57) ABSTRACT

The invention provides a method for determining whether a test compound binds to a target RNA, the method comprising the steps of: (a) contacting the test compound with a pair of indicator molecules comprising an antimicrobial labelled with a donor group or an acceptor group and the target RNA labelled with a complementary acceptor or donor group, the pair being capable of binding to each other in an orientation that permits the donor group to come into sufficient proximity to the acceptor group to permit fluorescent resonance energy transfer and/or quenching to take place; and (b) measuring the fluorescence of the target RNA and/or the antimicrobial in the presence of the test compound and comparing this value to the fluorescence of a standard.

28 Claims, 41 Drawing Sheets

FIG. 5

| FIG. 5A |
|---------|
| FIG. 5B |

Decoding site

16S rRNA (E.Coli)

A site

FIG. 5A

GTPase centre

Thiostrepton binding site

| FIG. 12A | FIG. 12B |

16 S rRNA Secondary Structure *E Coli*

Helix 34

A

Secondary Structure:
small subunit
ribosomal RNA:
A site

BACILLUS SUBTILIS

DOMAIN: Bacteria
KINGDOM: Gram-positive
ORDER: Low G+C

BORRELIA BURGDORFERI

DOMAIN: Bacteria
KINGDOM:
ORDER: Spirochaetales

FIG. 13C

CAMPYLOBACTER SPUTORUM

DOMAIN: Bacteria
KINGDOM: Purple Bacteria
ORDER: delta/epsilon

MYCOPLASMA HYPNEUMONIAE

DOMAIN: Bacteria
KINGDOM: Gram-positive
ORDER: Mycoplasmales

*Mycoplasma genitalium*

DOMAIN: *Bacteria*
KINGDOM: *Gram-positive*
ORDER: *Mycoplasmales*

| FIG. 14A | FIG. 14B |
| FIG. 14C | FIG. 14D |
| FIG. 14E | FIG. 14F |

Secondary Structure: large subunit ribosomal RNA - 3' half

*BACILLUS SUBTILIS*

DOMAIN: *Bacteria*
KINGDOM: *Low G+C*
ORDER: *Gram-positive*

BORRELIA BURGDORFERI
DOMAIN: Bacteria
KINGDOM:
ORDER: Spirochaetales

CAMPYLOBACTER SPUTORUM
SUBSP. SPUTORUM

DOMAIN: *Bacteria*
KINGDOM: *Purple Bacteria*
ORDER: *delta/epsilon*

CLOSTRIDIUM INNOCUUM

DOMAIN: Bacteria
KINGDOM: Gram-positive
ORDER: Mycoplasmales

*HAEMOPHILUS INFLUENZAE*

DOMAIN: *Bacteria*
KINGDOM: *Purple Bacteria*
ORDER: *gamma*

MYCOPLASMA GENITALIUM

DOMAIN: Bacteria
KINGDOM: Gram-positive
ORDER: Mycoplasmales

*MYCOPLASMA HYOPNEUMONIAE*
DOMAIN: *Bacteria*
KINGDOM: *Gram-positive*
ORDER: *Mycoplasmales*

SEQUENCE LISTING

<160> NUMBER OF SEQ ID NOS: 37

<210> SEQ ID NO 1
<211> LENGTH: 25
<212> TYPE: RNA
<213> ORGANISM: Escherichia coli

<400> SEQUENCE: 1
ccgucacacc uucgggugaa gucgg     25

<210> SEQ ID NO 2
<211> LENGTH: 1542
<212> TYPE: RNA
<213> ORGANISM: Escherichia coli

<400> SEQUENCE: 2
aaauugaaga guuugaucau ggcucagauu gaacgcuggc ggcaggccua acacaugcaa     60

-continued

```
gucgaacggu aacaggaaga agcuugcuuc uuugcugacg aguggcggac ggguagaguaa    120
ugucugggaa acugccugau ggaggggau aacuacugga aacguagcu aauaccgcau       180
aacgucgcaa gaccaaagag ggggaccuuc gggccucuug ccaucggaug ugcccagaug     240
ggauuagcua guaggugggg uaacggcuca ccuaggcgac gaucccuagc uggucugaga     300
ggaugaccag ccacacugga acugagacac gguccagacu ccuacgggag gcagcagugg    360
ggaauauugc acaaugggcg caagccugau gcagccaugc cgcguguaug aagaaggccu    420
ucggguugua aaguacuuuc agcggggagg aaggaguaua aguuaauacc uuugcucauu   480
gacguuaccc gcagaagaag caccggcuaa cuccgugcca gcagccgcgg uaauacggag    540
ggugcaagcg uuaaucggaa uuacugggcg uaaagcgcac gcaggcgguu uguuaaguca    600
gaugugaaau ccccgggcuc aaccuggaa cugcaucuga uacuggcaag cuugagucuc     660
guagagggg guagaauucc aggugguagcg ugaaaugcg uagagaucug gaggaauacc     720
gguggcgaag gcggccccu ggacgaagac ugacgcucag gugcgaaagc gggggagca     780
aacaggauua gauacccugg uaguccacgc cguaaacgau gucgacuugg agguugugcc    840
cuugaggcgu ggcuuccgga gcuaacgcgu uaagucgacc gccuggggag uacggccgca   900
agguuaaaac ucaaaugaau ugacggggc ccgcacaagc gguggagcau ugguuuaau      960
ucgaugcaac gcgaagaacc uuaccggguc uugacaucca cggaaguuuu cagagaugag  1020
aaugugccuu cgggaaccgu gagacaggug cugcauggcu gucgcagcu cguguuguga    1080
aauguugggu uaaguccgc aacgagcgca acccuuaucc uuuguugcca gcggccggc      1140
cgggaacuca aaggagacug ccagugauaa acuggaggaa ggugggggaug acgucaaguc   1200
aucauggccc uuacgaccag ggcuacacac gugcuacaau ggcgcauaca aagagaagcg    1260
accucgcgag agcaagcgga ccucauaaag ugcgucguag uccggauugg agucugcaac   1320
ucgacuccau gaagucggaa ucgcuaguaa ucguggauca gaaugccacg gugaauacgu    1380
ucccgggccu uguacacacc gcccgucaca ccauggagu ggguugcaaa agaaguaggu     1440
agcuuaaccu ucgggagggc gcuuaccacu uugugauuca ugacuggggu gaagucguaa   1500
caagguaacc guagggggaac cugcgguugg aucaccuccu ua                     1542
```

<210> SEQ ID NO 3
<211> LENGTH: 2904
<212> TYPE: RNA
<213> ORGANISM: Escherichia coli

<400> SEQUENCE: 3

```
gguuaagcga cuaagcguac acgguggaug cccuggcagu cagaggcgau gaaggacgug    60
cuaaucugcg auaagcgucg guaaggugau augaaccguu auaaccggcg auuuccgaau   120
ggggaaaccc agugugutuuc gacacacuau cauuaacuga auccuaggu uaugagggcg    180
aaccggggga acugaaacau cuaaguaccc cgaggaaaag aaaucaaccg agauuccccc  240
aguagcggcg agcgaacggg gagcagccca gagccugaau cagugugugu guuaguggaa  300
gcgucuggaa aggcgcgcga uacaggguga cagccccgua cacaaaaaug cacaugcugu     360
gagcucgaug aguagggcgg gacacguggu auccugucug aauauggggg gaccauccuc    420
caaggcuaaa uacuccugac ugaccgauag ugaaccagua ccgugaggga aaggcgaaaa   480
gaacccggc gaggggagug aaaaagaacc ugaaccgug uacuacaag cagugggagc      540
acgcuuaggc gugugacugc guaccuuuug uauaaugggu cagcgacuua uauucuguag    600
```

-continued

| | | | | |
|---|---|---|---|---|
| caagguuaac | cgaauagggg | agccgaaggg | aaaccgaguc | uuaacugggc | guuaaguugc | 660 |
| aggguauaga | cccgaaaccc | ggugaucuag | ccaugggcag | guugaagguu | ggguaacacu | 720 |
| aacuggagga | ccgaaccgac | uaauguugaa | aaauuagcgg | augacuugug | gcuggggug | 780 |
| aaaggccaau | caaaccggga | gauagcuggu | ucuccccgaa | agcuauuuag | guagcgccuc | 840 |
| gugaauucau | cuccggggu | agagcacugu | uucggcaagg | gggucauccc | gacuuaccaa | 900 |
| cccgaugcaa | acugcgaaua | ccggagaaug | uuaucacggg | agacacacgg | cgggugcuaa | 960 |
| cguccgucgu | gaagagggaa | acaacccaga | ccgccagcua | agguccccaaa | gucauggua | 1020 |
| agugggaaac | gaugugggaa | ggcccagaca | gccaggaugu | uggcuuagaa | gcagccauca | 1080 |
| uuuaaagaaa | gcguaauagc | ucacggucg | agucggccug | cgcggaagau | guaacggggc | 1140 |
| uaaaccaugc | accgaagcug | cggcagcgac | gcuuaugcgu | uguggguag | gggagcguuc | 1200 |
| uguaagccug | cgaaggugug | cugugaggca | ugcuggaggu | aucagaagug | cgaaugcuga | 1260 |
| cauaaguaac | gauaaagcgg | gugaaaagcc | cgcucgccgg | aagaccaagg | guuccuguccc | 1320 |
| aacguuaauc | ggggcagggu | gagucgaccc | cuaaggcgag | gccgaaaggc | guagucgaug | 1380 |
| ggaaacaggu | uaauauuccu | guacuuggug | uuacugcgaa | gggggacgg | agaaggcuau | 1440 |
| guuggccggg | cgacguugu | cccgguuuaa | gcguguaggc | ugguuuucca | ggcaaauccg | 1500 |
| gaaaaucaag | gcugaggcgu | gaugacgagg | cacuacggug | cugaagcaac | aaaugcccug | 1560 |
| cuuccaggaa | aagccucuaa | gcaucaggua | acaucaaauc | guaccccaaa | ccgacacagg | 1620 |
| uggucaggua | gagaauacca | aggcgcuuga | gagaacucgg | gugaaggaac | uaggcaaaau | 1680 |
| ggugccguaa | cuucgggaga | aggcacgcug | auauguaggu | gaagcgacuu | gcucguggag | 1740 |
| cugaaaucag | ucgaagauac | cagcuggcug | caacuguuua | uuaaaaacac | agcacugugc | 1800 |
| aaacacgaaa | guggacguau | acggugugac | gccugcccgg | ugccggaagg | uuaauugaug | 1860 |
| ggguuagcgc | aagcgaagcu | cuugaucgaa | gccccgguaa | acggcggccg | uaacuauaac | 1920 |
| gguccuaagg | uagcgaaaau | uccuugucgg | guaaguuccg | accugcacga | auggcguaau | 1980 |
| gauggccagc | ugucuccac | ccgagacuca | gugaaauuga | acucgcugug | aagaugcagu | 2040 |
| guacccgcgg | caagacggaa | agaccccgug | aaccuuuacu | auagcuugac | acugaacauu | 2100 |
| gagccuugau | guguaggaua | ggugggaggc | uuagaagugu | ggacgccagu | cugcauggag | 2160 |
| ccgaccuuga | aauaccaccc | uuuaauguuu | gauguucuaa | cguugacccg | uauccgggu | 2220 |
| ugcggacagu | gucuggugg | uaguuugacu | ggggcggucu | ccuccuaaag | aguaacggag | 2280 |
| gagcacgaag | guuggcuaau | ccuggucgga | caucaggagg | uuagugcaau | ggcauaagcc | 2340 |
| agcuugacug | cgagcgugac | ggcgcgagca | ggugcgaaag | cagguucauag | ugauccggug | 2400 |
| guucugaaug | gaagggccau | cgcucaacgg | auaaaaggua | cuccggggau | aacaggcuga | 2460 |
| uaccgcccaa | gaguucauau | cgacggcggu | guuuggcacc | ucgaugucgg | cucaucacau | 2520 |
| ccugggggcug | aaguaggucc | ccaagggguau | gcuguucgcc | auuuaaagug | guacgcgagc | 2580 |
| ugggguuuaga | acgucgugag | acaguucggu | cccuaucugc | cgugggcgcu | ggagaacuga | 2640 |
| gggggggcugc | uccuaguacg | agaggaccgg | agugacgca | ucacuggugu | ucgguugc | 2700 |
| augccaaugc | acugcccggu | agcuaaaugc | ggaagauga | agcugaaaa | gcaucuaagc | 2760 |
| acgaaacuug | ccccgagaug | aguucccccu | gacccuuuaa | ggguccugaa | ggaacguuga | 2820 |
| agacgacgac | guuuauaggc | cgggugugua | agcgcagcga | ugcguugagc | uaaccgguac | 2880 |
| uaaugaaccg | ugaggcuuaa | ccuu | | | | 2904 |

-continued

<210> SEQ ID NO 4
<211> LENGTH: 145
<212> TYPE: RNA
<213> ORGANISM: Escherichia coli

<400> SEQUENCE: 4
accgcccguc acaccauggg aguggguugc aaaagaagua gguagcuuaa ccuucgggag    60
ggcgcuuacc acuuugugau ucaugacugg ggugaagucg uaacaaggua accguagggg   120
aaccugcggu uggaucaccu ccuua                                         145

<210> SEQ ID NO 5
<211> LENGTH: 101
<212> TYPE: RNA
<213> ORGANISM: Escherichia coli

<400> SEQUENCE: 5
gcccgucaca ccaugggagu ggguugcaaa agaaguaggu agcuuaaccu ucgggagggc    60
gcuuaccacu uugugauuca ugacuggggu gaagucguaa c                       101

<210> SEQ ID NO 6
<211> LENGTH: 33
<212> TYPE: RNA
<213> ORGANISM: Bacillus subtilis

<400> SEQUENCE: 6
gcccgucaca ccauggcugg ggugaagucg ggc                                 33

<210> SEQ ID NO 7
<211> LENGTH: 24
<212> TYPE: RNA
<213> ORGANISM: Bacillus subtilis

<400> SEQUENCE: 7
ggcgucacac cuucggguga aguc                                           24

<210> SEQ ID NO 8
<211> LENGTH: 104
<212> TYPE: RNA
<213> ORGANISM: Escherichia coli

<400> SEQUENCE: 8
gaacauugag ccuugaugug uaggauaggu gggaggcuua gaagugugga cgccagucug    60
cauggagccg accugaaaau accacccuuu aauguuugau guuc                    104

<210> SEQ ID NO 9
<211> LENGTH: 94
<212> TYPE: RNA
<213> ORGANISM: Escherichia coli

<400> SEQUENCE: 9
gaugugggaa ggcccagaca gccaggaugu uggcuuagaa gcagccauca uuuaaagaaa    60
gcguaauagc ucacggucg agucggccug cgcg                                 94

<210> SEQ ID NO 10
<211> LENGTH: 58
<212> TYPE: RNA
<213> ORGANISM: Escherichia coli

<400> SEQUENCE: 10
gccaggaugu uggcuuagaa gcagccauca uuuaaagaaa gcguaauagc ucacgguu      58

<210> SEQ ID NO 11
<211> LENGTH: 162
<212> TYPE: RNA
<213> ORGANISM: Escherichia coli

<400> SEQUENCE: 11
gugcugcaug gcugucguca gcucguguug ugaaauguug gguuaagucc cgcaacgagc    60
gcaacccuua uccuuuguug ccagcggucc ggccgggaac ucaaaggaga cugccaguga   120
uaaacuggag aaggugggg augacgucaa gucaucaugg cc                       162

<210> SEQ ID NO 12
<211> LENGTH: 147
<212> TYPE: RNA
<213> ORGANISM: Bacillus subtilis

<400> SEQUENCE: 12
ccgcccguca caccacgaga guuuguaaca cccgaagucg gugagguaac cuuuuaggag    60
ccagccgccg aagguggggac agaugauugg ggugaagucg uaacaaggua gccguaucgg   120
aaggugcggc uggaucaccu ccuuucu                                       147

<210> SEQ ID NO 13
<211> LENGTH: 144
<212> TYPE: RNA
<213> ORGANISM: Borrelia burgdorferi

<400> SEQUENCE: 13
cgcccgucac accacccgag uugaggauac ccgaagcuau uauucuaacc cguaaggagg    60
aagguauuua agguauguuu agugaggggg gugaagucgu aacaagguag ccguacugga   120
aagugcggcu ggaucaccuc cuuu                                          144

<210> SEQ ID NO 14
<211> LENGTH: 137
<212> TYPE: RNA
<213> ORGANISM: Campylobacter sputorum
<220> FEATURE:
<221> NAME/KEY: misc_feature
<222> LOCATION: ()..()
<223> OTHER INFORMATION: "n" is any ribonucleotide

<400> SEQUENCE: 14
cgcccgucac accaugggag uugauuucac ucgaagccca aauaccaaau ugguuauggu    60 ccacaguggaa aucagcgacu ggggugaagu cguaacaagg uaaccguagg agaacnnnnn   120
nnnnnnnnnn nnnnnnn                                                  137

<210> SEQ ID NO 15
<211> LENGTH: 145
<212> TYPE: RNA
<213> ORGANISM: Mycoplasma hyopneumoniae

<400> SEQUENCE: 15
ccgcccguca caccauggga guugguaaug cccaaagucg gugaguuaac uucggagacc    60
auugccuaag gcaggaccga ugacuggggu gaagucguaa caagguaucc cuacgagaac   120 gugggaugg aacaccuccu uucua                                          145

<210> SEQ ID NO 16
<211> LENGTH: 144
<212> TYPE: RNA
<213> ORGANISM: Clostridium innocuum

```
<400> SEQUENCE: 16
ccgcccguca aaccauggga gucaguaaua cccgaagccg guggcauaac cguaaggagu      60
gagccgucga agguaggacc ggacuggggu uaagucguaa caagguaucc cuacgggaac    120 gugggaugg aucaccuccu uucu                                             144

<210> SEQ ID NO 17
<211> LENGTH: 144
<212> TYPE: RNA
<213> ORGANISM: Haemophilus influenzae

<400> SEQUENCE: 17
ccgcccguca caccauggga gugguugua ccagaaguag auagcuuaac cuuuuggagg       60
gcguuuacca cgguaugauu caugacuggg gugaagucgu aacaagguaa ccguaggga     120 accugcgguu ggaucaccuc cuua                                            144

<210> SEQ ID NO 18
<211> LENGTH: 142
<212> TYPE: RNA
<213> ORGANISM: Mycoplasma genitalium

<400> SEQUENCE: 18
ccgcccguca aacuaugaaa gcugguaaua uuuaaaaacg uguugcuaac cuuuauugga      60
agcgcauguc aaggauagca ccggugauug gaguuaaguc guaacaaggu accccuacga    120
gaacgugggg guggaucacc uc                                              142

<210> SEQ ID NO 19
<211> LENGTH: 96
<212> TYPE: RNA
<213> ORGANISM: Bacillus subtilis

<400> SEQUENCE: 19
guugguacag cuuguacagg auagguagga gccuuggaaa ccggagcgcc agcuucggug      60
gaggcaucgg uggauacua cccuggcugu auugac                                96

<210> SEQ ID NO 20
<211> LENGTH: 100
<212> TYPE: RNA
<213> ORGANISM: Borrelia burgdorferi

<400> SEQUENCE: 20
gauuugauua aauaugugua ggauaggugg gagacuuuga agcuaucucg ucagggguag      60
uggagucaau cuugaaauac cacccuuguu uaauuagguu                          100

<210> SEQ ID NO 21
<211> LENGTH: 100
<212> TYPE: RNA
<213> ORGANISM: Haemophilus influenzae

<400> SEQUENCE: 21
acauugaauu uugaugugua ggauaggugg gagccuuuga agcagugacg ccagucauug      60
uggaggcgac cuugaaauac cacccuuuaa cguuugaugu                          100

<210> SEQ ID NO 22
<211> LENGTH: 100
<212> TYPE: RNA
<213> ORGANISM: Helicobacter pylori
```

<400> SEQUENCE: 22
uaaugggaau aucaugcgca ggauaggugg gaggcuuuga aguaagggcu uuggcucuua    60
uggagucauc cuugagauac cacccuugau guuucuguua    100

<210> SEQ ID NO 23
<211> LENGTH: 102
<212> TYPE: RNA
<213> ORGANISM: Mycobacterium leprae

<400> SEQUENCE: 23
auguucggug cgguuugugu aggauaggug ggagacugug aaacuucgac gcuaguuggg    60
guggagucgu uguugaaaua ccacucugau uguauugaac au    102

<210> SEQ ID NO 24
<211> LENGTH: 99
<212> TYPE: RNA
<213> ORGANISM: Mycoplasma genitalium

<400> SEQUENCE: 24
caaaacacca ccauguagag aauagguagg agcaauugau gcaaguucgc aaggauuugu    60
ugaugugaaa ugugaauac uacccuuggu uauguuuug    99

<210> SEQ ID NO 25
<211> LENGTH: 88
<212> TYPE: RNA
<213> ORGANISM: Bacillus subtilis

<400> SEQUENCE: 25
guggaguugc uuagacaacc aggauguugg cuuagaagca gccaccauuu aaagagugcg    60
uaauagcuca cggucgagu gacucugc    88

<210> SEQ ID NO 26
<211> LENGTH: 89
<212> TYPE: RNA
<213> ORGANISM: Borrelia burgdorferi

<400> SEQUENCE: 26
guuuagguac guaaacagcc aggagguugg cuuagaagca gccauaccuu uaaagagugc    60
guaauagcuc acggucgag uacuuaagc    89

<210> SEQ ID NO 27
<211> LENGTH: 88
<212> TYPE: RNA
<213> ORGANISM: Haemophilus influenzae

<400> SEQUENCE: 27
gugggaaggc uuagacagcu aggauguugg cuuagaagca gccaucauuu aaagaaagcg    60
uaauagcuca cuagucgagu cggccugc    88

<210> SEQ ID NO 28
<211> LENGTH: 89
<212> TYPE: RNA
<213> ORGANISM: Helicobacter pylori

<400> SEQUENCE: 28
uguguggcua cuaaacaac caggagguug gcuuagaagc agccauccuu uaaagaaagc    60
guaacagcuc acuggucuag uggucaugc    89

<210> SEQ ID NO 29
<211> LENGTH: 88
<212> TYPE: RNA
<213> ORGANISM: Mycobacterium leprae

<400> SEQUENCE: 29
gugcagucgc aaagacaacc aggagguugg cuuagaagca gccacccuug aaagagugcg       60
uaauagcuca cuggucaagu gauugugc                                         88

<210> SEQ ID NO 30
<211> LENGTH: 88
<212> TYPE: RNA
<213> ORGANISM: Mycoplasma genitalium

<400> SEQUENCE: 30
gugaaagugc uaaaacagca aggauguugg cuuagaagca gccaucguuu aaagagugcg       60
uaacagcuca cuugucgagu guuuuugc                                         88

<210> SEQ ID NO 31
<211> LENGTH: 156
<212> TYPE: RNA
<213> ORGANISM: Bacillus subtilis

<400> SEQUENCE: 31
gugcaugguu gucgucagcu cgugucguga gauguugggu uaagucccgc aacgagcgca       60
acccuugauc uuaguugcca gcauucaguu gggcacucua aggugacugc cggugacaaa      120
ccggaggaag gugggauga cgucaaauca ucaugc                                 156

<210> SEQ ID NO 32
<211> LENGTH: 165
<212> TYPE: RNA
<213> ORGANISM: Borrelia burgdorferi

<400> SEQUENCE: 32
ggugcugcau gguugucguc agcucgugcu gugagguguu ggguuaaguc ccgcaacgag       60
cgcaacccuu guuaucuguu accagcaugu aauggugggg acucagauaa gacugccggu      120
gauaagucgg aggaagguga ggaugacguc aaaucaucau ggccc                      165

<210> SEQ ID NO 33
<211> LENGTH: 161
<212> TYPE: RNA
<213> ORGANISM: Campylobacter sputorum

<400> SEQUENCE: 33
gugcugcacg gcugucguca gcucgugucg ugagauguug gguuaagucc cgcaacgagc       60
gcaacccacg uguuuaguug cuaacaguua ggcugagcac ucuaaacaga cugccuucgu      120
aaggaggagg aaggugugga cgacgucaag ucaucauggc c                          161

<210> SEQ ID NO 34
<211> LENGTH: 166
<212> TYPE: RNA
<213> ORGANISM: Clostridium innocuum

<400> SEQUENCE: 34 aggugguagca ugguugucgu cagcucgugu cgugagaugu uggguuaagu cccgcaacga      60
gcgcaacccu ugucgcaugu uaccagcauc aaguggggga cucaugcgag acugccggug      120
acaaaccgga ggaaggugggg gaugacguca aaucaucaug ccccuu                    166

```
<210> SEQ ID NO 35
<211> LENGTH: 160
<212> TYPE: RNA
<213> ORGANISM: Haemophilus influenzae

<400> SEQUENCE: 35
ugcugcaugg cugucgucag cucguguugu gaaauguugg guuaaguccc gcaacgagcg      60
caacccuuau ccuuuguugc cagcgacuug gucgggaacu caaaggagac ugccagugau     120
aaacuggagg aaggugggga ugacgucaag ucaucauggc                          160

<210> SEQ ID NO 36
<211> LENGTH: 150
<212> TYPE: RNA
<213> ORGANISM: Mycoplasma genitalium

<400> SEQUENCE: 36
aggugguGca ugguugucgu cagcucgugu cgugagaugu uggguuaagu cccgcaacga      60
gcgcaacccu uaucguuagu uacauuguuu aacgagacug cuaauguaaa uuggaggaag     120
gaagggauga cgucaaauca ucaugccccu                                     150

<210> SEQ ID NO 37
<211> LENGTH: 162
<212> TYPE: RNA
<213> ORGANISM: Mycoplasma hyopneumoniae

<400> SEQUENCE: 37
gauggugcau gguugucguc agcucguguc gugagauguu agguuaaguc cugcaacgag      60
cgcaacccuu uucuuuaguu gcuaacauuu aguugagaac ccuaaagaua cugccggcgc     120
aagccggagg aaggugggga cgacgucaaa ucaucaugcc uc                       162
```

METHODS AND KITS FOR DISCOVERY OF RNA-BINDING ANTIMICROBIALS

FIELD OF THE INVENTION

The present invention relates to the specific interactions of low molecular weight compounds with RNA. More particularly, the present invention relates to compositions, methods and kits for identifying antimicrobials and other compounds that interfere with RNA-antimicrobial interactions.

BACKGROUND OF THE INVENTION

In most biological systems, the function of RNA is often determined by the interactions between highly conserved RNA structures. In many circumstances it is desirable to develop drugs that bind RNA at sites of conserved structure to act as competitive inhibitors of the RNA function that is derived from various RNA interactions, such as those exemplified by RNA—RNA and RNA-protein interactions. These types of drugs have potential applications in a wide range of diseases including bacterial, viral, and fungal infections.

1. Use of Fluorescence to Measure Ligand Binding to RNA

A critical step in the development of RNA-binding drugs is the development of simple and robust assays that are suitable for the high throughput screening of large compound libraries developed either by combinatorial synthesis traditional medicinal chemistry approaches, or from collections of natural products.

There are many different types of assays that measure the binding of ligands to nucleic acids and utilize fluorescence resonance energy transfer (FRET) to generate a signal. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap. FRET is also a distance-dependent interaction which is dependent on the inverse sixth power of the intermolecular separation, making it a sensitive measurement of molecular distances (Stryer, 1978 and Selvin, 1995).

An improvement in the technology for measuring the ability of small molecules to bind to RNA is to utilize fluorescent reporters. Current methods all rely on the labeling of either the nucleic acid or the ligand with a fluorescent tag and measuring changes in fluorescence emission spectrum after binding. For example, Royer (U.S. Pat. No. 5,445,935 (issued Aug. 29, 1995)) described the use of polarization of the fluorescence emission from a labeled macromolecule, such as a DNA or RNA oligonucleotide, to assess the binding of the labeled macromolecule to a second unlabeled macromolecule, such as a protein. Similarly, (Metzger et al. (1997) have measured binding of unlabeled pep tides derived from Tat to TAR RNA by measuring quenching of the intrinsic fluorescence of the peptide after it is bound to RNA.

In another application of fluorescence polarization, Richardson and Schulman (U.S. Pat. No. 4,257,774 (issued Mar. 24, 1981)) reported a method for detecting compounds that interact with nucleic acids by inhibition of acridine orange binding to the nucleic acid which results in a change in fluorescence polarization. This method is of limited practical use because the binding of acridine is through intercalation at a wide variety of sites on double-helical structures, with the consequent result that the specificity of the assay is limited.

Wang & Rando (U.S. Pat. No. 5,593,835 (issued Jan. 14, 1997) and Wang et al., 1997) discovered that the attachment of certain fluorescent moieties to an aminoglycoside antibiotic enables the subsequent binding interaction of the antibiotic with an RNA molecule to be enhanced. They have used this property to develop quantitative screening methods and kits for RNA binding compounds. In their method the fluorescently-labeled antibiotic is bound to a pre-selected region of the target RNA, thereby forming a complex which is less fluorescent than the unbound fluorescent antibiotic because of quenching of the fluorescent moiety due to its interaction with the target RNA molecule. The complex is then mixed with a compound-to-be-tested, and the fluorescence of the antibiotic measured. The antibiotic becomes more fluorescent if the compound displaces the antibiotic in the complex and binds to the pre-selected region of the target RNA.

A general limitation to the use of a single fluorescent group on a reporter molecule is that this group has to interact directly with the RNA target in order to show alterations in its fluorescence emission spectrum. This severely limits the number of positions on the reporter that can be modified and can also alter the nature of the binding of the reporter to the RNA.

It is an object of the invention to apply FRET methodologies to measure the formation of a complex between a fluorescently-labeled antimicrobial and fluorescently-labeled RNA target. One reason why this approach has not been undertaken previously is that NMR studies have shown that of RNA-peptide complexes are in intermediate exchange, suggesting a high degree of conformational flexibility and dynamic exchange at the RNA-peptide interface (Puglisi et al., 1992; Aboul-ela et al., 1995; Brodsky & Williamson, 1997; Cai et al., 1998; De Guzman et al., 1998). These dynamic properties are, in theory, a severe hindrance to the development of FRET.

2. RNA Targets for Drug Discovery

Although RNA is often referred to as being single stranded and unstructured, most biologically active RNA molecules actually have a number of intramolecular bindings and contacts that create a wide variety of structures and folds. In RNA structures, the secondary structure is energetically the largest contributor to the overall three-dimensional fold. A primary element of secondary structure in large RNA molecules is the RNA double helix built by Watson-Crick base pairings between two regions of the RNA polynucleotide. The helical elements in RNA are typically interrupted by bulges and internal loops. In addition to disruptions of the helical structures, biologically active RNA molecules typically contain specialized loop sequences that create stable bends in RNA. Associations between single stranded regions as well as those between single stranded regions and double helices lead to structural elements creating tertiary structures. Many tertiary structural elements in RNA form recurrent motifs, such as "pseudoknots"created by the interactions of pairs of loop structures. Additional tertiary structure elements such as base triples are also commonly found in large RNA structures.

3. RNA Targets in Ribosomal RNA

Many antibiotics function by inhibiting protein synthesis, and it has become increasingly clear that many do so by acting at the level of ribosomal RNA (rRNA). The 16S rRNA of the small, 30S ribosomal subunit and the 23S rRNA of the large, 50S ribosomal subunit are both large RNAs for which there are highly refined secondary structure models. The rRNA binding sites of many different types of antibiotics have been mapped by chemical and enzymatic probing approaches. These antibiotic binding sites are localized to various subregions on the 16S and 23S rRNAs, as exemplified by those identified for the *Escherichia coli* rRNAs (FIGS. 1 and 2). These sites include, but are not limited to, the 16S rRNA A site (FIGS. 5 and 13), the 16S rRNA spectinomycin binding site (FIGS. 12 and 16), the 23S rRNA L1 (or E site) (FIGS. 10 and 14), and the 23S rRNA GTPase center (L11 binding site) (FIGS. 11 and 15). Examples of antibiotics targeted to these sites include, but are not limited to, binding of the 16S rRNA A site by members of the aminoglycoside class, binding of the 23S rRNA L1 site (the E site) by the oxazolidinone class, and binding of the 23S rRNA GTPase center by the thiazole class.

4. RNA Mimics of Antibiotic Binding Sites

Targeting drugs against large RNAs such as the 16S rRNA (>1,400 nucleotides) and 23S rRNA (>2,700 nucleotides) can be difficult in part due to the size of the RNAs, which can hinder drug development assays. For instance, it can be difficult to produce a suitable quantity and quality of large RNA molecules for assays, and the large size of RNAs can make them refractory to the physical or chemical manipulations of assays. Studies on RNA structure have shown that large RNAs are often composed of subdomains which have the ability to fold autonomously. Based on subdomains, it is possible to generate small fragments of RNA that are often able to fold into structures that mimic binding sites found in the entire, larger RNA. Model RNAs that fold into the correct structures have been demonstrated to bind molecules with similar affinities and specificities to those of the original RNA sequences. These small RNAs are useful for studying RNA binding interactions, since their small size permits synthesis on a large scale either by chemical methods or by transcription from DNA templates.

RNA model sequences include nucleic acid structures derived from parental ribosomal RNA that are capable of binding to a ligand (such as an aminoglycoside) as in the original RNA structure. These model sequences often include a stabilizing sequence that provides the model RNA with a conformation that permits ligand binding that is substantially identical to the parental RNA ligand binding pattern. For example, a small model RNA sequence used for investigating the binding of an aminoglycoside on *Escherichia coli* 16S rRNA has been described by Purohit and Stern (1994, and U.S. Pat. No. 5,712,096 (issued Jan. 27, 1998). The use of small model RNAs based on subdomains from large rRNAs will facilitate the development of RNA-binding drugs.

SUMMARY OF THE INVENTION

The invention provides a method for determining whether a test compound binds to a target RNA, the method comprising the steps of: (a) contacting the test compound with a pair of indicator molecules comprising an antimicrobial labelled with a donor group or an acceptor group and the target RNA labelled with a complementary acceptor or donor group, the pair being capable of binding to each other in an orientation that permits the donor group to come into sufficient proximity to the acceptor group to permit fluorescent resonance energy transfer and/or quenching to take place; and (b) measuring the fluorescence of the target RNA and/or the antimicrobial in the presence of the test compound and comparing this value to the fluorescence of a standard.

In preferred embodiments, the standard comprises the indicator pair in the presence or absence of test compound, the fluorescently-labelled target RNA in the presence or absence of test compound, or fluorescently-labelled antimicrobial in the presence or absence of test compound. It will be appreciated that the fluorescence of the standard may have been determined before performing the method, or may be determined during or after the method has been performed. It may be an absolute standard.

The method may also be used in the identification of compounds that bind to the target RNA from within a plurality of test compounds, such as in screening methods. The method may, therefore, involve the initial step of providing a plurality of test compounds, which may include compounds not already known to bind to the target RNA sequence.

In a typical embodiment, therefore, the invention provides a method of screening for compounds that bind to a target RNA, comprising the steps of (a) contacting a test compound with an indicator complex, the indicator complex comprising a fluorescently-labeled antimicrobial bound to a fluorescently labeled target RNA in an orientation that permits the fluorescent groups present on each molecule to come into sufficient proximity to permit fluorescent resonance energy transfer to take place; and (b) measuring the fluorescence of the target RNA and the antimicrobial in the presence of the test compound and comparing this value to the fluorescence of a standard.

In preferred embodiments of the methods of the invention, the antimicrobial is selected from the antimicrobial classes aminoglycoside, cyclic peptide, macrolide, tetracycline, oxazolidinone, thiazole, protein, glycoprotein, alkyloid, nuclease, and N-glycosidase.

Typically, the antimicrobial binds the target RNA with a Kd of between $1 \times 10^{-12}$ and $1 \times 10^{-4}$ M, and the target RNA is between 5 and about 750 nucleotides in length.

In other embodiments, the target RNA is derived from bacterial or viral eukaryotic RNA, and may be chemically modified.

In a particularly preferred embodiment, the target RNA is bacterial 16S rRNA or 23 S rRNA or is a fragment of 5-750, 10-450, 15-150, or 20-50 nucleotides of 16S rRNA or 23S rRNA that binds to an antimicrobial.

In other preferred embodiments, the target RNA and the antimicrobial are fluorescently labelled by covalent attachment of a fluorescent group. For instance, the target RNA may be fluorescently labelled at the 3' or 5' end of a strand within th e target RNA, or within the chain of the target RNA.

It also may be preferred in some instances that the antimicrobial or the target RNA molecule is adhered to a solid support.

In the methods of the invention, it also is preferred that either (i) the donor is attached to the target RNA, and the acceptor is attached to the antimicrobial, or (ii) the donor is attached to the antimicrobial, and the acceptor is attached to the target RNA.

The invention also includes a method for determining the presence in a biological sample of a compound that binds to a target RNA molecule, comprising (a) contacting the sample with a pair of indicator molecules comprising an antimicrobial labelled with a donor group or an acceptor group and the target RNA labelled with a complementary acceptor or donor group, the pair being capable of binding to each other in an orientation that permits the donor group to come into sufficient proximity to the acceptor group to permit fluorescent resonance energy transfer and/or quenching to take place; and (b) measuring the fluorescence of the target RNA and the antimicrobial as an indication of binding. Preferably in this method, said biological sample comprises a tissue or fluid from a mammal, a plant extract, or prokaryotic extract.

In other preferred embodiments, the acceptor is able to quench the fluorescence of the donor after binding of the target RNA and the antimicrobial.

In certain preferred embodiments of the invention, only quenching of the donor due to the proximity of the acceptor in the antimicrobial/RNA complex is measured. In certain embodiments of the invention, the target RNA carries a chromophore or fluorophore that quenches the fluorescence of the fluorescent group on the antimicrobial after binding of the two molecules. In other embodiments of the invention, the antimicrobial carries a chromophore or fluorophore that quenches the fluorescence of the fluorescent group on the target RNA after binding of the two molecules.

In some methods according to the invention, the target RNA, the antimicrobial, and the test compound are mixed, and the fluorescence of the mixture is compared to standards. In other methods, the test compound is first mixed with the labelled RNA in order to form a complex in the absence of the labelled antimicrobial, and the antimicrobial is then added. Alternatively, a complex is pre-formed between the labelled RNA and the labelled antimicrobial before addition of the test compound.

The invention also encompasses a kit for determining whether a test compound binds to a target RNA, the kit comprising (a) a target RNA labelled with a donor group or an acceptor group and (b) an antimicrobial labelled with a complementary acceptor or donor group, wherein the antimicrobial and the target RNA are capable of binding to each other in an orientation that permits the donor group to come into sufficient proximity to the acceptor group to permit fluorescent resonance energy transfer and/or quenching.

As used herein, "antimicrobial" refers to an agent that inhibits the growth (i.e. by 5%, 10%, 50%, or even up to 100%, as determined by measuring optical density of cells during log phase growth) and/or metabolism of a microorganism or kills a microorganism, including a prokaryotic and/or a eukaryotic cell, such as yeast, and/or a virus. Antimicrobials useful in the invention can thus be virtually any of those that may bind to RNA in such a manner so as to reduce or prevent metabolism and/or growth of the microorganism containing the RNA, and include but are not limited to antimicrobials from the classes aminoglycosides, peptides, cyclic peptides, macrolides, lincomycins, tetracyclines, chloramphenicols, cycloheximides, oxazolidinones, thiazoles, proteins, glycoproteins, alkyloids, nucleases, and N-glycosidases.

As used herein, "target RNA" refers to the fluorescently labelled RNA that binds the fluorescently labelled antimicrobial. The target RNA can constitute a complete RNA that may include one or more ribosomal proteins and that is capable of binding an antimicrobial, such as a complete 16S ribosomal RNA or a complete 23S ribosomal RNA. Alternatively, the target RNA can be comprised of a fragment or subregion of the entire 16S or 23S rRNA that may include one or more ribosomal proteins and that binds to an antimicrobial. Ribosomal RNAs useful as targets in the invention include those from microorganisms, such as eubacteria and yeast, as many antimicrobials have been demonstrated to bind to both 16S rRNA (FIG. 1) and 23S rRNA (FIG. 2). Ribosomal RNAs are highly conserved in their sequences, secondary and tertiary structure, as are the antimicrobial binding fragments of rRNAs (see FIGS. 5 and 12), and thus prokaryotic and eukaryotic rRNAs of lower organisms are useful according to the invention.

As used herein, the term "fragment" refers to a RNA that is structurally similar to a portion of a larger RNA, wherein the fragment is capable of binding molecules in the same manner as the entire, larger RNA.

As used herein, the term "antimicrobial binding site" refers to a site on a RNA that is capable of binding an antimicrobial molecule. Antimicrobial binding sites on the 16S rRNA include but are not limited to those on the 16S A site, the 16S spectinomycin site, and sites capable of binding pactamycin and edeine, as shown in FIG. 1. Antimicrobial binding sites on the 23S rRNA include but are not limited to those 23S GTPase center/L11 binding site, the L1 (E site) binding site, the viomycin binding site, the vernamycin B binding site, and the site bound by the MLS group of antibiotics, as shown in FIG. 2.

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1–100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers that, following attachment to either the RNA target molecule or to the antimicrobial, show alterations in absorption spectrum which permit the group to exhibit either FRET or quenching when placed in proximity to the donor through the binding interactions of two molecules.

As used herein, references to "fluorescence" or "fluorescent groups" or "fluorophores" include luminescence and luminescent groups, respectively.

As used herein, the term "quenching" refers to the transfer of energy from donor to acceptor which is associated with a reduction of the intensity of the fluorescence exhibited by the donor.

Standard nucleotide abbreviations are used herein: A is a nucleotide comprising an adenine base; G is a nucleotide comprising a guanine base; C is a nucleotide comprising a cytosine base, and U is a nucleotide comprising a uracil base; R is a nucleotide comprising a purine base (i.e. A or G), Y is a nucleotide comprising a pyrimidine base (i.e. C or U); and N is any nucleotide. Each occurrence of R, Y or N in a sequence may be the same or different. As used herein the term nucleotide may refer to a deoxyribonucleic acid (DNA) or ribonucleic acid (RNA). Preferably, the compounds of the present invention are RNA.

Further features and advantages of the invention will become more fully apparent in the following description of the embodiments and drawings thereof, and from the claims.

DESCRIPTION

The invention pertains to a simple and robust solution-based assay designed to detect compounds that compete for RNA-binding with an antimicrobial.

The use of an appropriately positioned donor group on one molecule and acceptor group on a second molecule leads to significantly improved sensitivity and specificity in the assay and distinguishes this assay from previous approaches involving the use of only a single fluorescent group placed on either the target RNA or the antimicrobial.

These findings have been exploited to develop the present invention, which includes quantitative screening methods and kits for identifying RNA-binding compounds. The invention is described in detail below.

All references below are incorporated herein in their entirety.

The Antimicrobial

Figure 3:
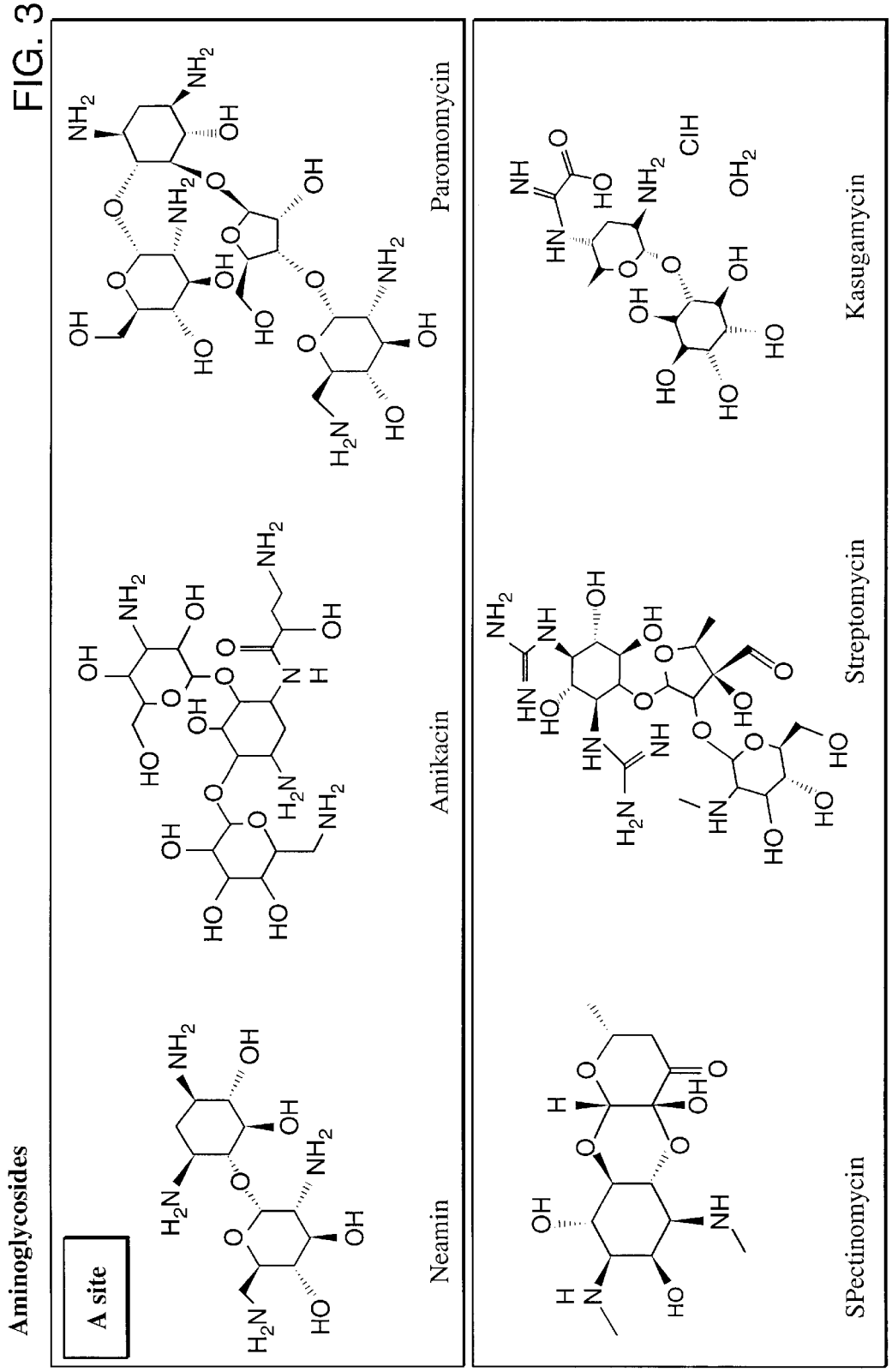
FIG. 3 shows the structures of several aminoglyosides.
Figure 4:
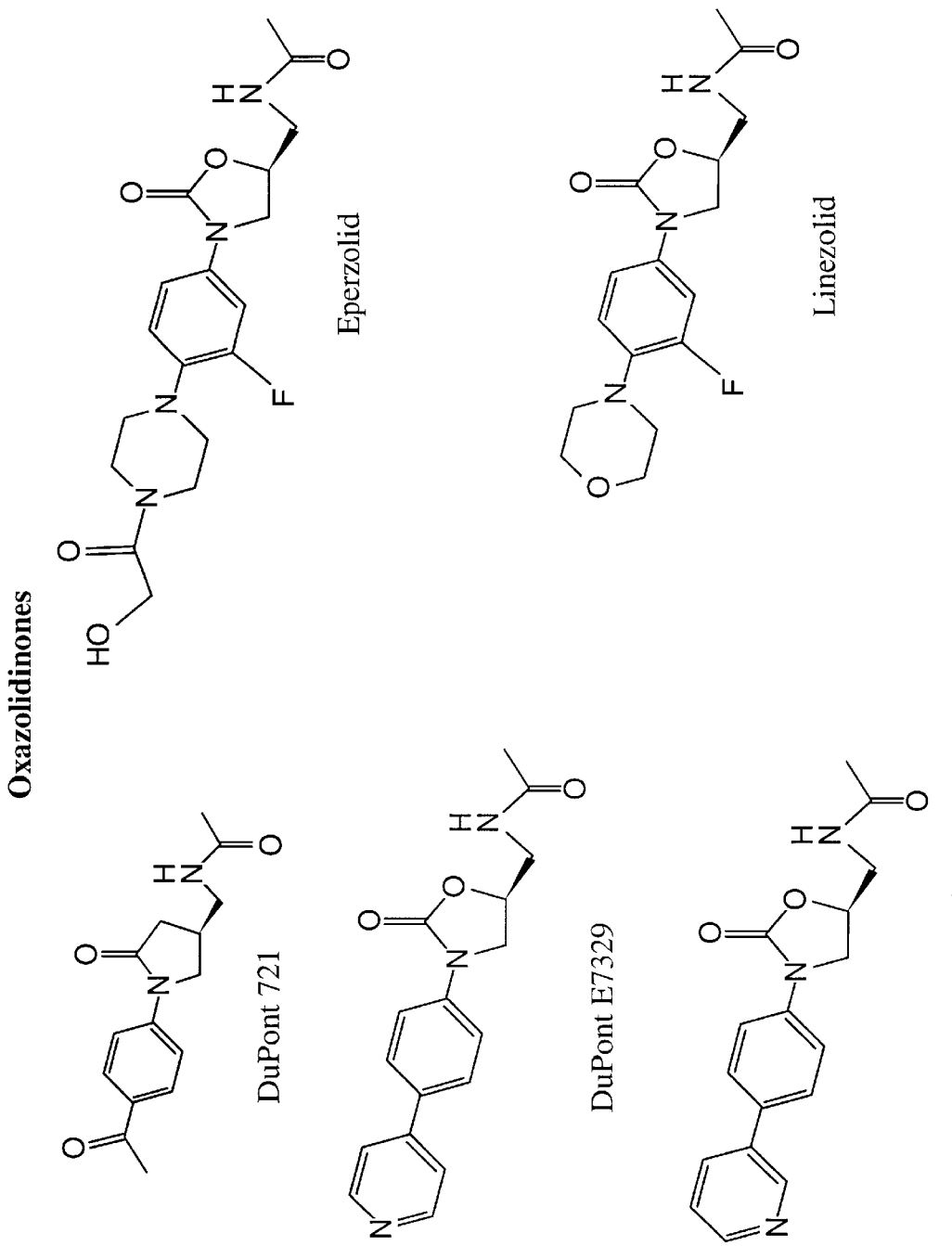
FIG. 4 shows the structures of several oxazolidinones.

An antimicrobial useful according to the invention is capable of binding to the target RNA. Several antimicrobials function by inhibiting protein synthesis, and have been demonstrated to inhibit a variety of steps in translation by binding to eubacterial ribosomal RNA (rRNA) (Spahn and Prescott, 1996). Many antibiotic binding sites on rRNAs have been identified by mutational and structural probing analyses (Spahn and Prescott, 1996, supra). These binding sites are exemplified by, but not limited to, those shown for 16S rRNA in FIG. 1 and 23S rRNA in FIG. 2. The binding of antibiotics is not limited to binding of rRNA, as antibiotics have been found to bind to other RNAs, including but not limited to transfer RNA (tRNA) (see Table 7), the HIV-1 RRE transcriptional activator region (Zapp et al., 1993, Cell 74:969), self-splicing group I intron RNA (von Ahsen et al., 1991, Nature 353: 268) and hammerhead ribozymes (Stage et al., 1995, RNA 1:95). Antimicrobials useful in the invention can thus be virtually any of those that may bind to RNA, and include but are not limited to antimicrobials from the classes aminoglycosides, peptides, cyclic peptides, macrolides, lincomycins, tetracyclines, chloramphenicols, cycloheximides, oxazolidinones, thiazoles, proteins, glycoproteins, alkyloids, nucleases, and N-glycosidases. Representative antimicrobials of these classes include but are not limited to those listed in Tables 1–4, 7, and 8, as well as the aminoglycosides pictured in FIG. 3 and the oxazolidinones pictured in FIG. 4. The antimicrobial may bind at a particular site of interest in the target RNA, and preferably forms a one-to-one complex with the target RNA, except for catalytic antimicrobials. The affinity with which the antimicrobial binds the target RNA may range in values of Kd of between $1\times10^{-12}$ and $1\times10^{-4}$ M.

The Target RNA

A "target RNA" useful according to the invention includes an RNA of interest which can be appropriately labeled (i.e., as described herein so as to provide FRET as fluorescence or quenching) and to which a suitable antimicrobial can be bound. Ribosomal RNAs useful as targets in the invention include those from microorganisms, such as eubacteria (exemplified by *Escherichia coli, Bacillus subtilis, Borrelia burgdorferi, Campylobacter sputorum, Mycoplasma hyopneumoniae, Clostridium innocuum, Haemophilus influenzae, Mycoplasma genitalium, Helicobactor pylori, Mycobacterium leprae*), yeast, actinomyces, and streptomyces, as many antibiotics have been demonstrated to bind to both 16S rRNA (FIG. 1) and 23S rRNA (FIG. 2) (Spahn and Prescott, 1996). Targets may also include other RNAs identified as having antibiotic binding sites. Examples of such RNAs include, but are not limited to, the self-splicing group I introns (von Ahsen et al., 1991, supra), the hammerhead ribozyme derived from the Avocado Sunblotch Viroid (Stage et al, 1995), the ribozyme derived from the human Hepatitis Delta Virus (Rogers et al., 1996), and the HIV RNA (Zapp et al., 1993). In addition, RNAs that have been selected for their ability to bind antimicrobials, using techniques such as in vitro evolution and selection of RNAs, may be useful targets.

Within the target 16S and 23S rRNAs, particular subregions of the rRNAs have been identified as the sites for which several antibiotics bind (Spahn and Prescott, 1996, supra). These rRNA subregions can serve as model target sequences that are representative of the sequences within the context of the entire rRNA. Such rRNA subregions include but are not limited to the 16S rRNA A site, the spectinomycin site in 16S rRNA, the L1 binding site (the E site) in 23S rRNA, and the GTPase center in 23S rRNA. An example of an effective model rRNA sequence has been described for an aminoglycoside antibiotic binding site on *Escherichia coli* 16S rRNA by Purohit and Stern (1994, and U.S. Pat. No. 5,712,096 (issued Jan. 27, 1998). This RNA model sequence includes a nucleic acid structure derived from the parental rRNA that is capable of binding to an aminoglycoside ligand (as in the parental structure) and a stabilizing sequence that provides the model RNA with a conformation that permits ligand binding that is substantially identical to the parental RNA ligand binding pattern.

A target site useful in the invention may include the antimicrobial target site or a nucleic acid structure which mimics the antimicrobial binding site in the native RNA. Preferably the mimic adopts a conformation substantially identical to the antimicrobial binding site in the native RNA and exhibits a ligand binding pattern substantially identical to that site bound in the native RNA.

The RNA targets of the present invention may comprise a single molecule, for example a single stranded RNA. Alternatively, the RNA targets of the present invention may comprise two or more, preferably two, annealed molecules, for example two single stranded RNA molecules annealed to one another.

A linker can serve to stabilize the RNA target. The linker may be a nucleotide (RNA or DNA) sequence capable of forming a duplex comprising Watson-Crick base pairs, a cross-linked sequence, and/or a sequence capable of forming a secondary structure such as a loop.

Target RNA sequences for use in the present invention can therefore be RNA sequences typically between 10 and about 750 nucleotides in length, or model RNA fragments preferably between about 20 and about 150 nucleotides. Target RNA sequences can be comprised of either chemically synthesized or enzymatically transcribed RNA. The RNA can be a single RNA capable of folding to form a secondary structure present in the original RNA target. Alternatively, the target sequences can be assembled from a number of short oligoribonucleotides that have been hybridized together and are capable of creating the RNA structure of interest present in the original RNA structure. Discontinuities in the target RNA sequence such as single stranded regions or helical junctions that are not involved in antimicrobial recognition can also be connected by short, single-stranded regions of RNA, tetraloops or other non-nucleotide linkers. Double stranded target RNA sequences, constructed from short oligoribonucleotides can be further stabilized in regions that are not involved in antimicrobial recognition by the extension of the helix beyond its normal length. The integrity of the RNA folding, and the stability of the folded structure can be increased by including the ribosomal protein that is associated with the region in the intact ribosome. Examples of the use of pairs of oligonucleotides which, after annealing, are able to mimic a folded RNA target structure are given in Karn et al. (WO92/02228 and U.S. Pat. No. 5,821,046 (issued Oct. 13, 1998)) and Karn et al. (WO92/05195 and U.S. Pat. No. 5,786,145 (issued Jul. 28, 1998)). A synthetic analogue of a ribozyme formed by the annealing of a pair of oligonucleotides is described in Slim et al., (1991) and Grasby et al., (1993). An example of the use of three oligonucleotides, which after annealing, are able to mimic a folded RNA target structure is the TWJ6 mimic of the Rev binding site on RRE RNA (Iwai et al., 1992; WO92/05195).

The target RNA may be a natural or synthetic RNA.

Since oligoribonucleotides are sensitive to cleavage by cellular ribonucleases, as well as to alkaline or acid conditions, it may be preferable to use as the RNA target molecule a chemically modified molecule that mimics the action of the RNA binding sequence but is more stable. Other modifications may also be desirable to provide groups for immobilizing the RNA target oligonucleotide on solid supports by covalent or non-covalent attachments. The RNA target oligonucleotide may be a naturally occurring oligonucleotide, or may be a structurally related variant of such an oligonucleotide having modified bases and/or sugars and/or linkages. The terms "RNA target" or "RNA target oligonucleotides" or "RNA oligonucleotides" as used herein are intended to cover all such variations.

Modifications, which may be made either into the binding site per se or to a part of the RNA target oligonucleotide that does not inhibit binding of the antimicrobial, may include, but are not limited to the following types:

a) Backbone modifications:
   (i) phosphorothioates (single S substituents or any combination of two or more with the remainder as O (Stein et al., 1988; Cosstick, 1990; Caruthers, 1989);
   (ii) methylphosphonates (Miller et al., 1980);
   (iii) phosphoramidates (Agrawal et al., 1988; Mag & Engels, 1988);
   (iv) phosphotriesters (Miller et al., 1982); and
   (v) phosphorus-free linkages (e.g. carbamate, acetamidate, acetate), (Gait et al., 1974);

b) Sugar modifications:
   (i) 2'-deoxynucleosides (R=H);
   (ii) 2'-O-methylated nucleosides (R=OMe; (Sproat et al., 1989));
   (iii) 2'-fluoro-2'-deoxynucleosides (R =F; (Schmidt et al., 1992)); and
   (iv) 2'-O-alkylated nucleosides (Sproat et al., 1991);

c) Base modifications (for a review see Gait et al., 1998):
   (i) pyrimidine derivatives substituted in the 5-position (e.g. methyl, bromo, fluoro etc. . . or replacing a carbonyl group by an amino group, (Piccirilli et al., 1990); and
   (ii) purine derivatives lacking specific nitrogen atoms (e.g. 7-deaza-adenine, hypoxanthine, or functionalised in the 8-position (e.g. 8-azido adenine, 8-bromo adenine), or additional functionalities (e.g. 2,6-diaminopurine (Lamm et al., 1991));

d) Oligonucleotides covalently linked to reactive functional groups (e.g. psoralens, (Lee et al., 1988); phenanthrolines, (Sun et al., 1988); mustards, (Vlassov et al., 1988));

e) irreversible cross-linking agents with or without the need for co-reagents)
   (i) acridine (intercalating agents, (Helene et al., 1985));
   (ii) thiol derivatives (reversible disulphide formation with proteins, (Connolly & Newman, 1989));
   (iii) aldehydes (Schiff's base formation);
   (iv) azido, bromo groups (UV cross-linking); and
   (v) ellipticenes (photolytic cross-linking, (Perrouault et al., 1990);

f) oligonucleotides containing haptens or other binding groups;

g) fluorescent moieties or other non-radioactive labels (Tuschl et al., 1994); and h) combination of two or more modifications selected from a to g.

Regions of the target RNA selected for binding to the antimicrobial include, but are not limited to, sequences bound by an RNA-binding protein and sequences with specific secondary structures formed by bulges, internal loops and junctions etc.

Figure 1:
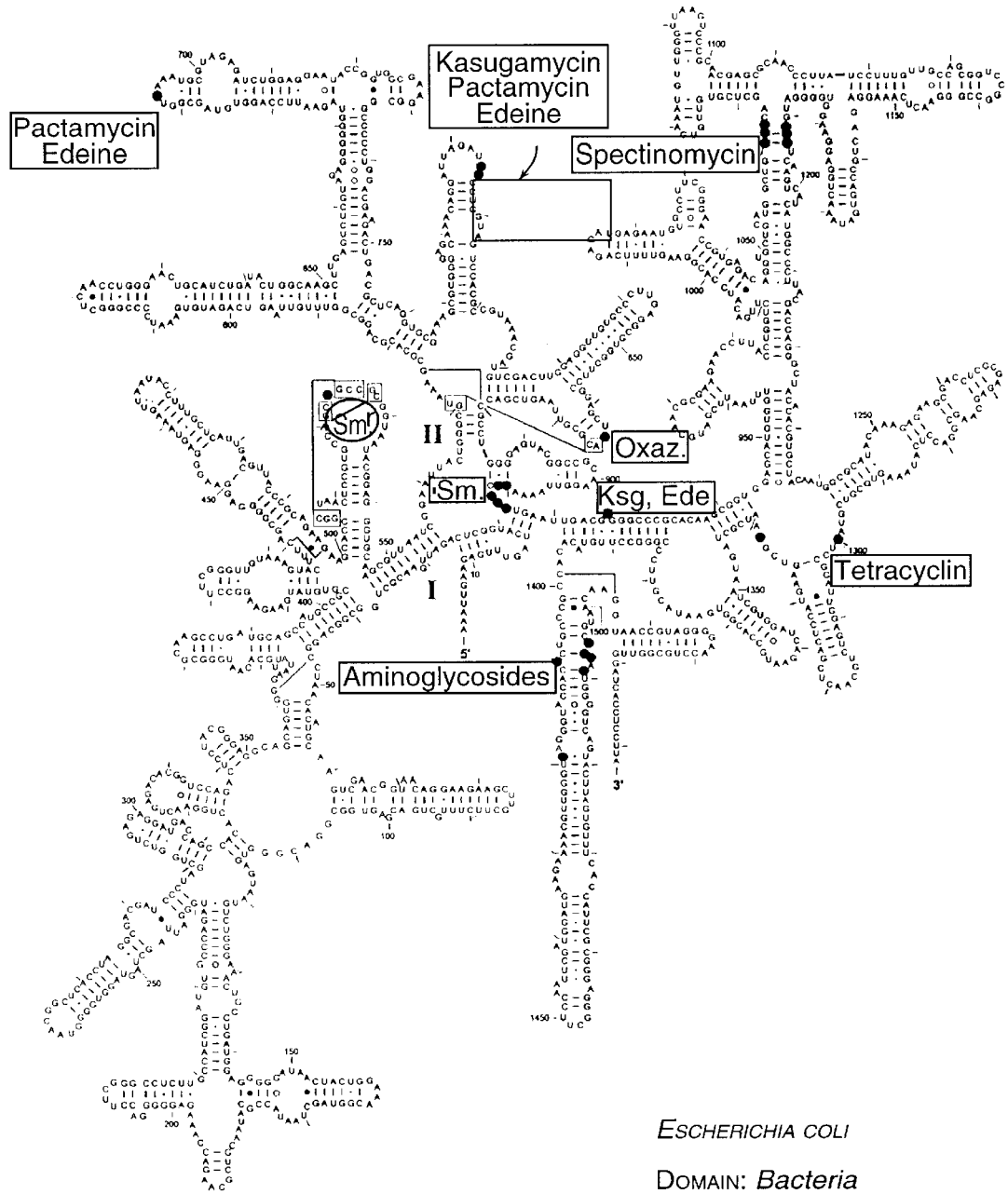
FIG. 1 shows a secondary structure model of 16S rRNA (SEQ ID NO: 2) with numerous antibiotic binding sites indicated.
Figure 2A:
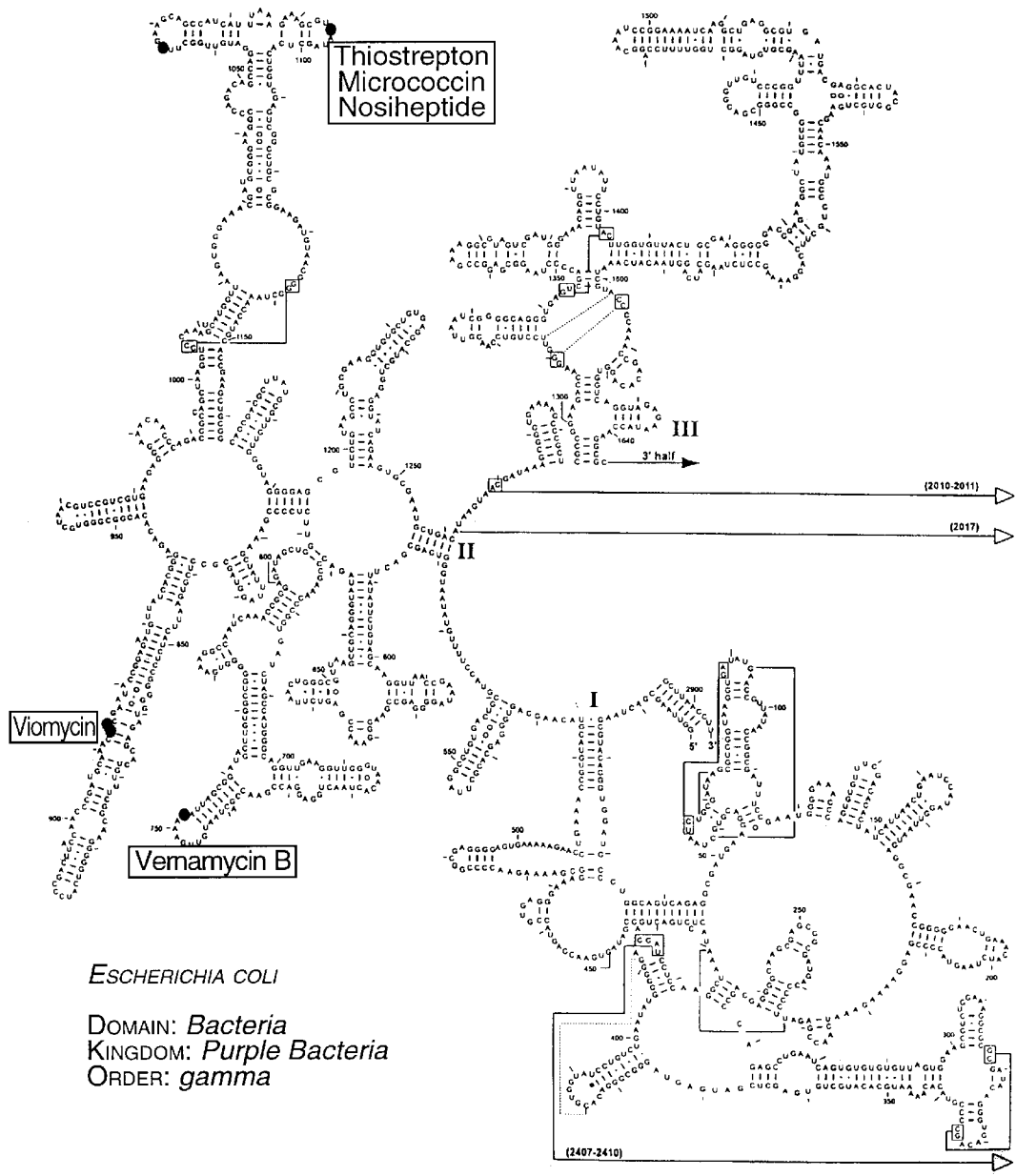
FIG. 2A shows a secondary structure model of the 5' half of 23S rRNA (SEQ ID NO: 3) with numerous antibiotic binding sites indicated.
Figure 2B:
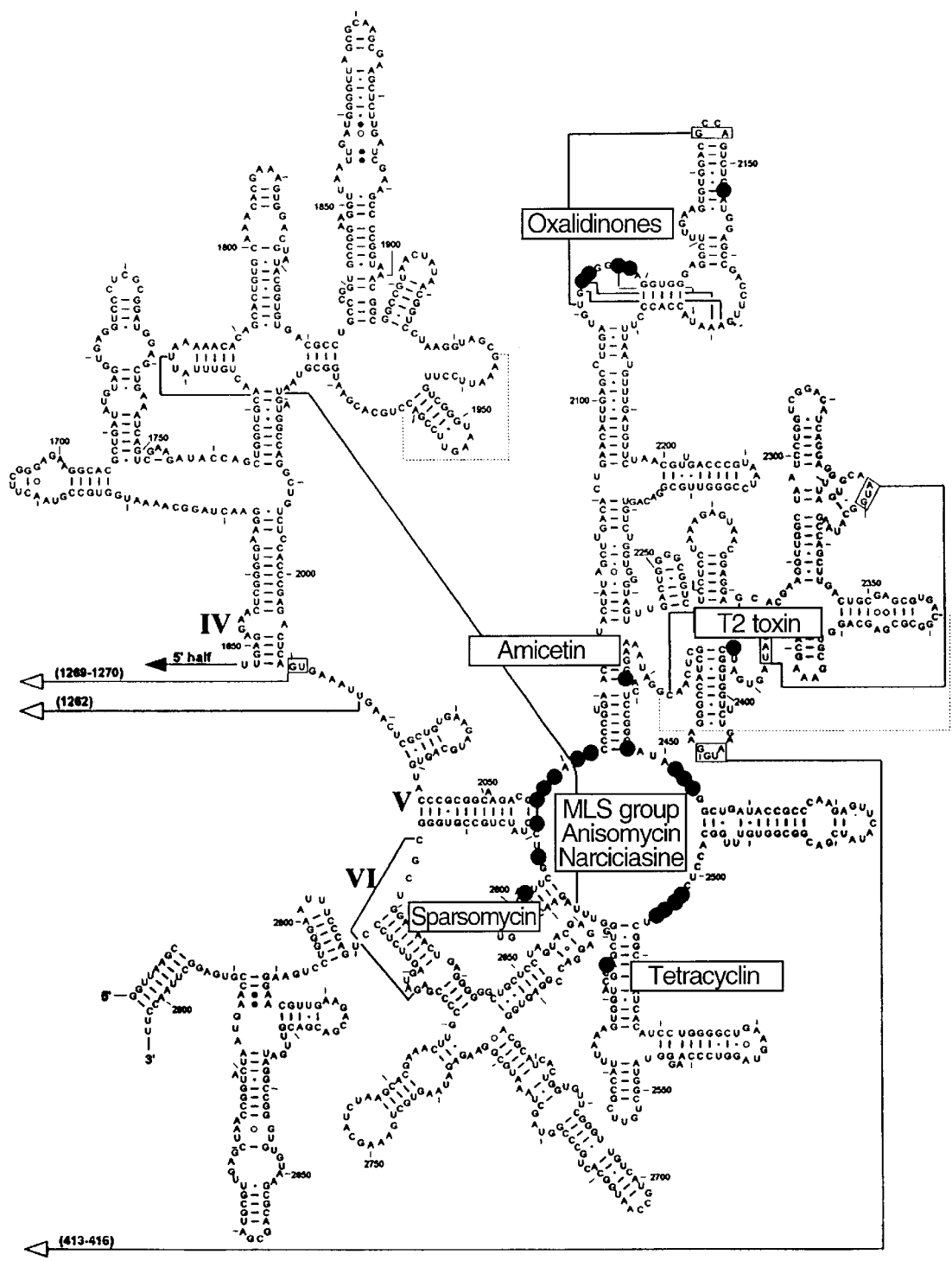
FIG. 2B shows a secondary structure model of the 3' half of 23S rRNA (SEQ ID NO: 3) with numerous antibiotic binding sites indicated.
Figure 9:
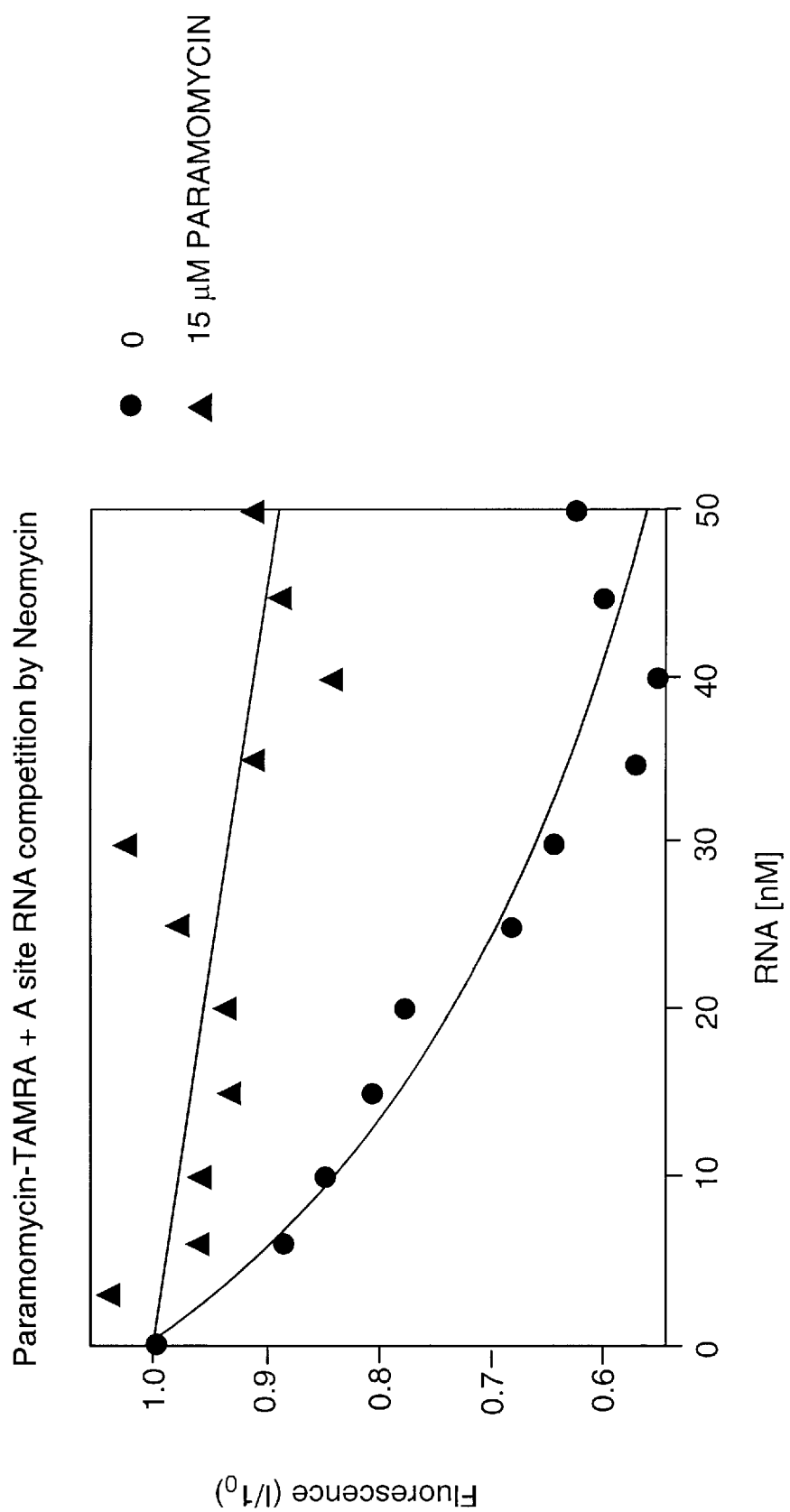
FIG. 9 shows the inhibition of binding of paramomycin-TAMRA to DABCYL-A site RNA by paramomycin.
Figure 10:
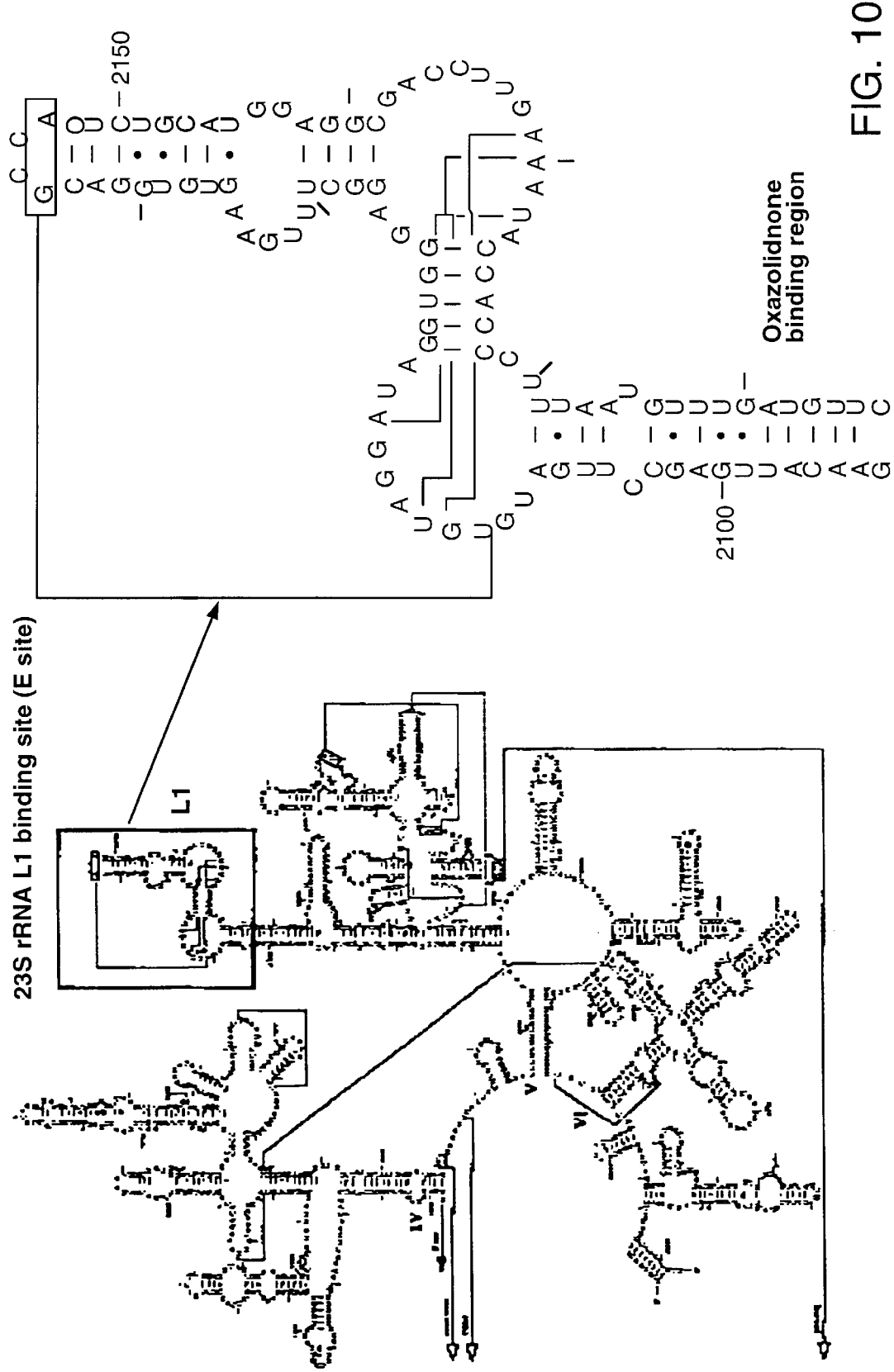
FIG. 10 shows the identification of a model sequence for the 23S rRNA L1 binding site (the E site) (SEQ ID NO 8).
Figures 14, 14A:
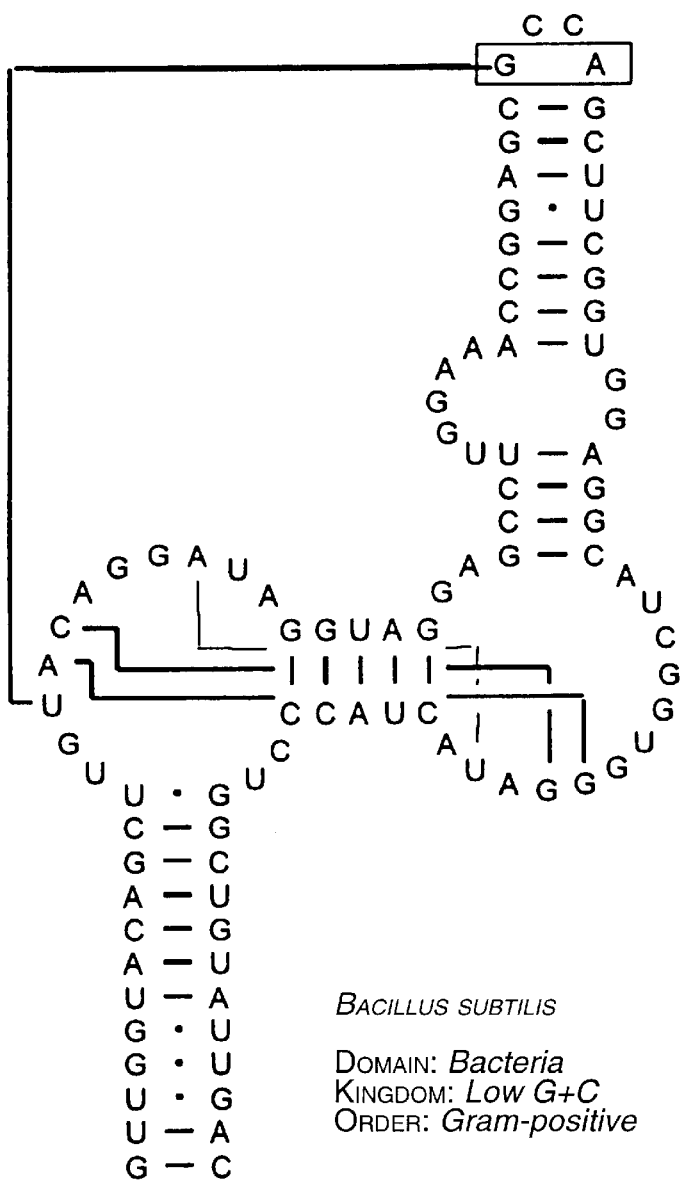
FIG. 14 Representative 23S rRNA sequences for the L1 binding site including the diverse organisms *Bacillus subtilis* (SEQ ID NO: 19), *Borrelia burgdorferi* (SEQ ID NO: 20), *Helicobacter pylori* (SEQ ID NO: 21), *Mycoplasma genitalium* (SEQ ID NO: 22), *Mycobacterium leprae* (SEQ ID NO: 23) and *Haemophilus influenzae* (SEQ ID NO: 24).
Figure 14B:
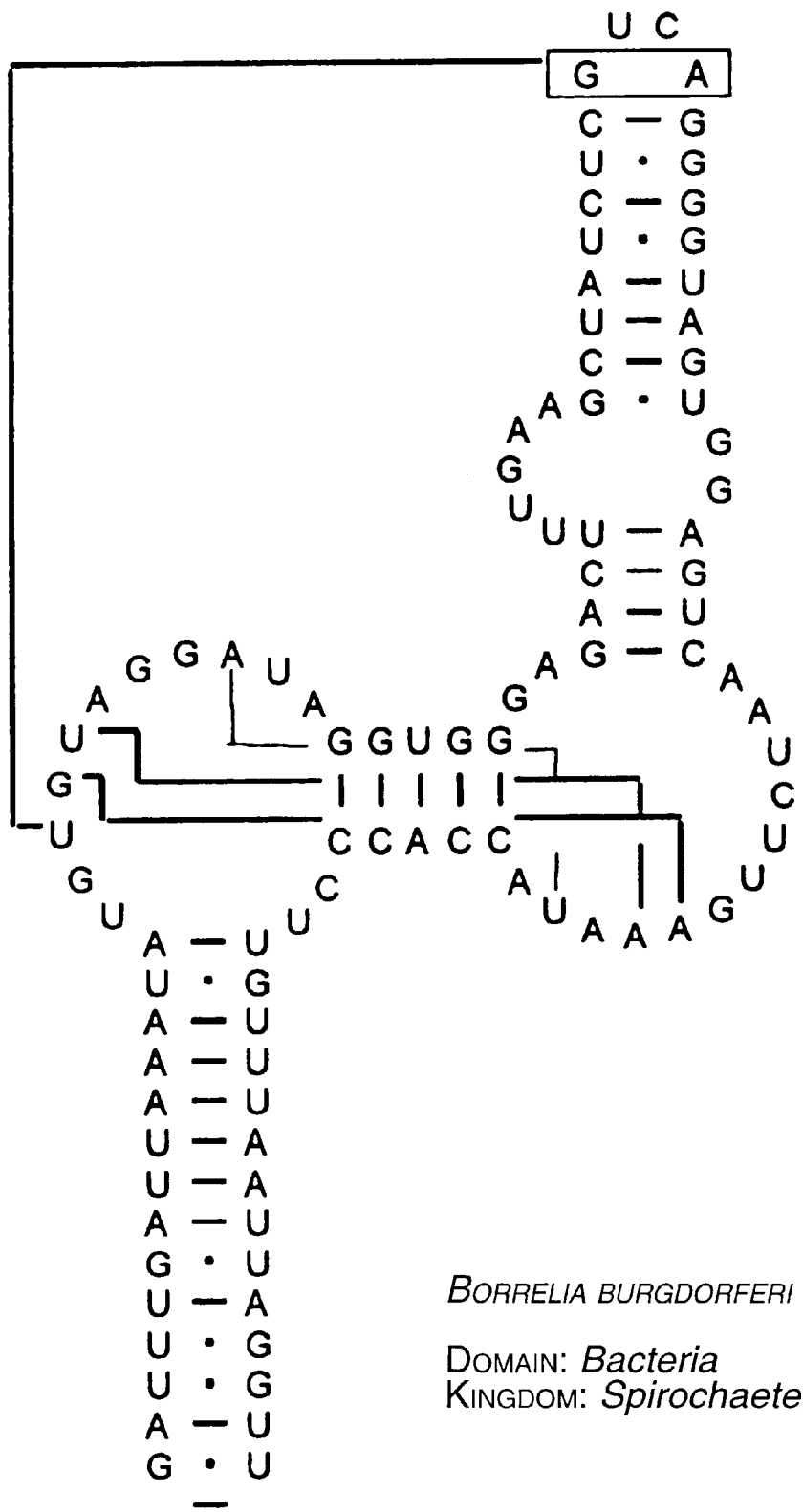
Figure 14C:
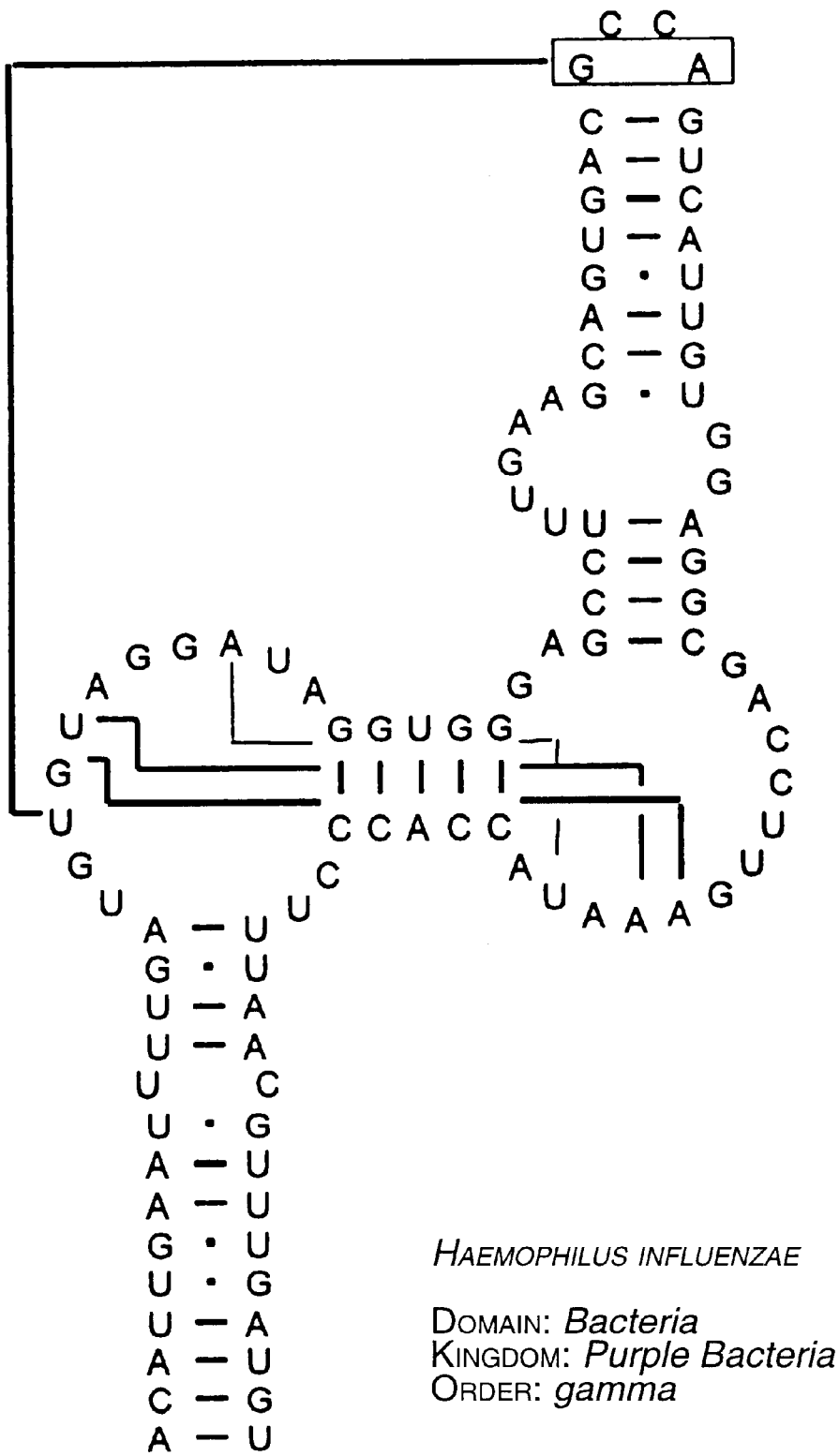
Figure 14D:
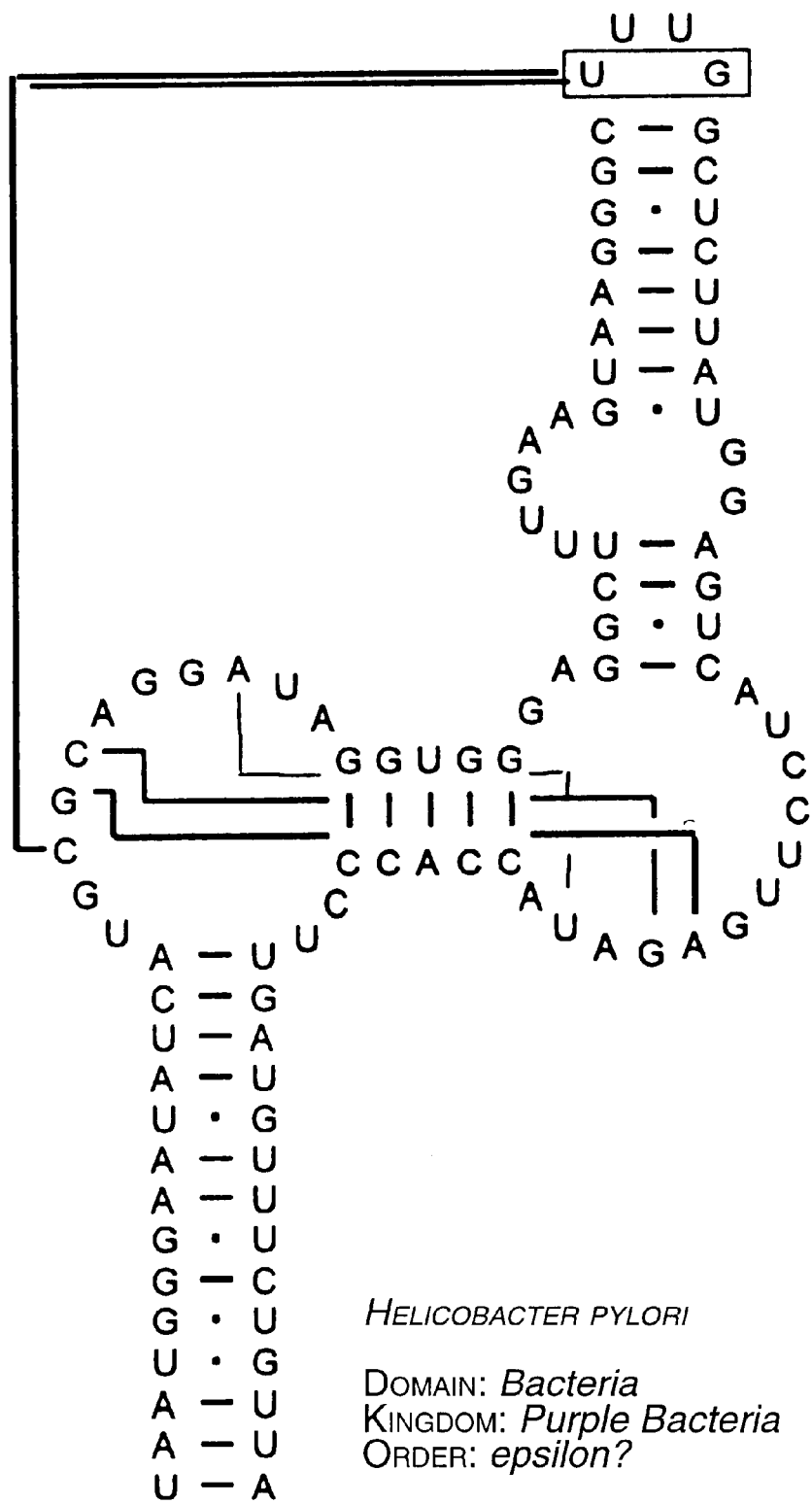
Figure 14E:
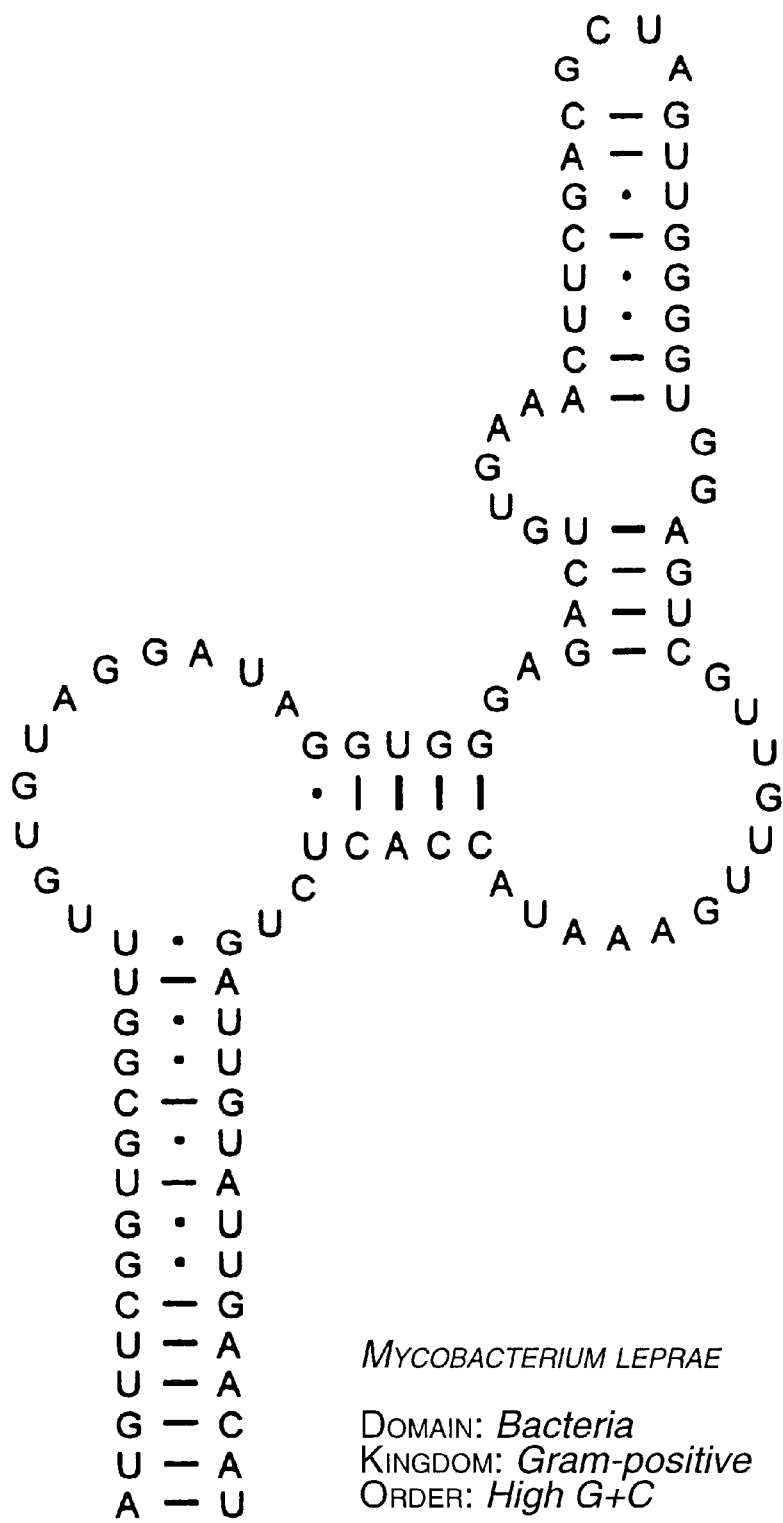
Figure 14F:
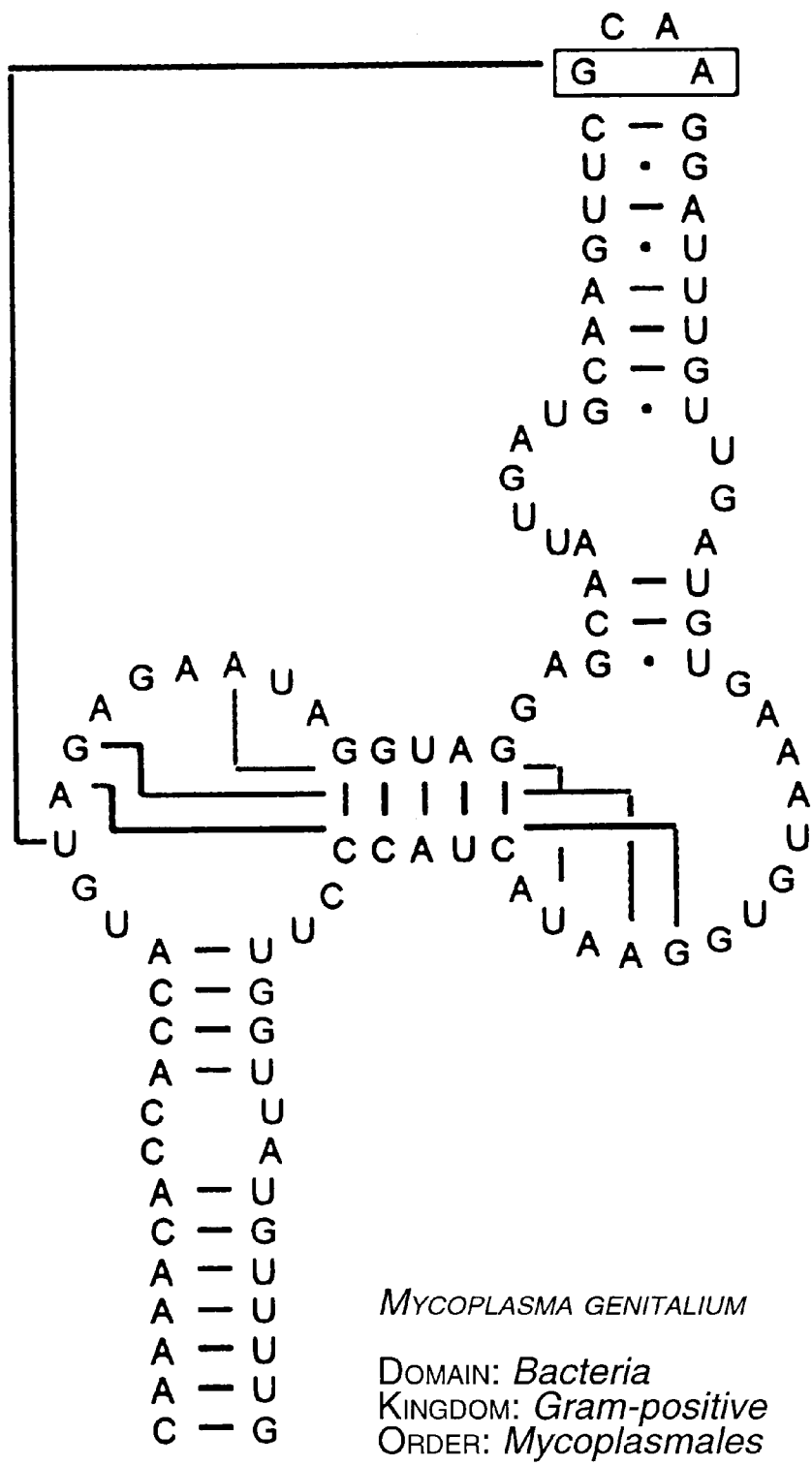
Figure 15A:
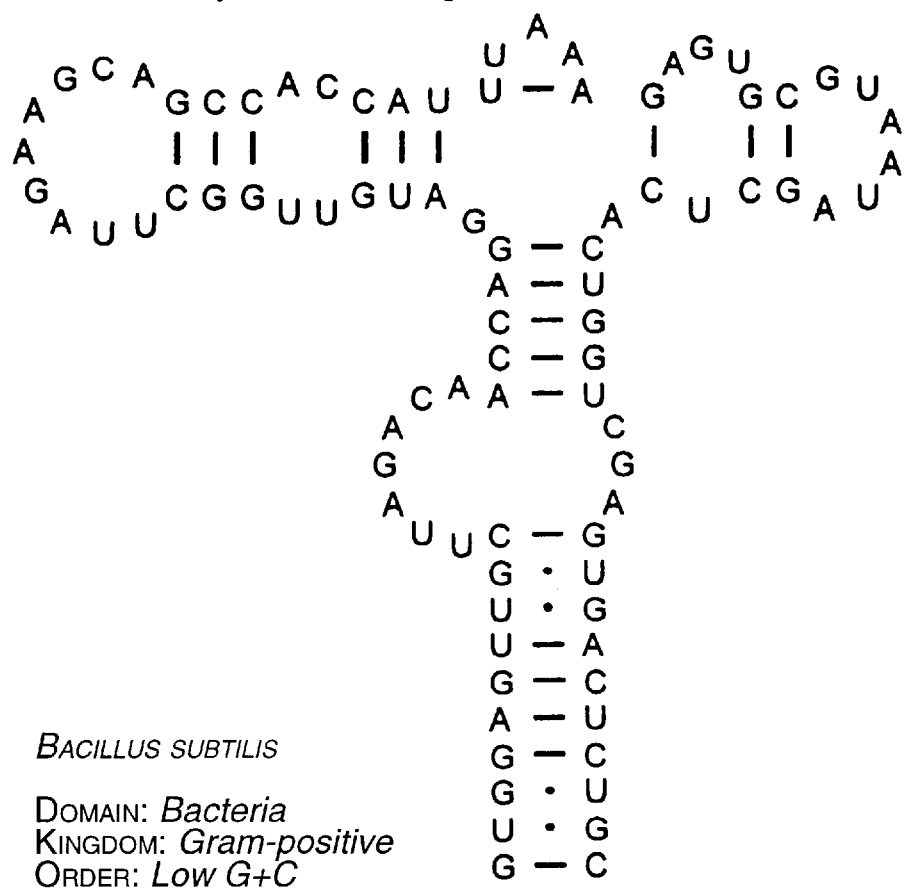
FIG. 15 Representative 23S rRNA sequences for the L11 binding site including the diverse organisms *Bacillus subtilis* (SEQ ID NO: 25), *Borrelia burgdorferi* (SEQ ID NO: 25), *Helicobacter pylori (SEQ ID NO:* 27), *Mycoplasma genitalium* (SEQ ID NO: 28), *Mycobacterium leprae* (SEQ ID NO: 29) and *Haemophilus influenzae* (SEQ ID NO: 30).
Figure 15B:
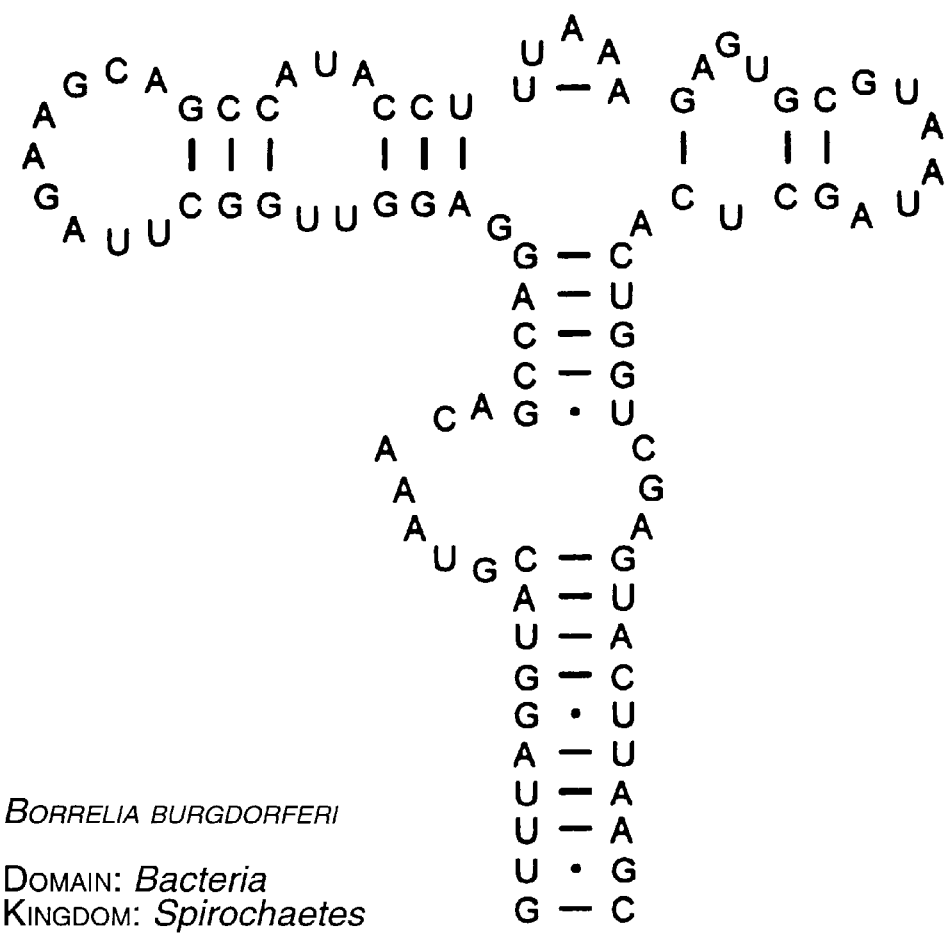
Figure 15C:
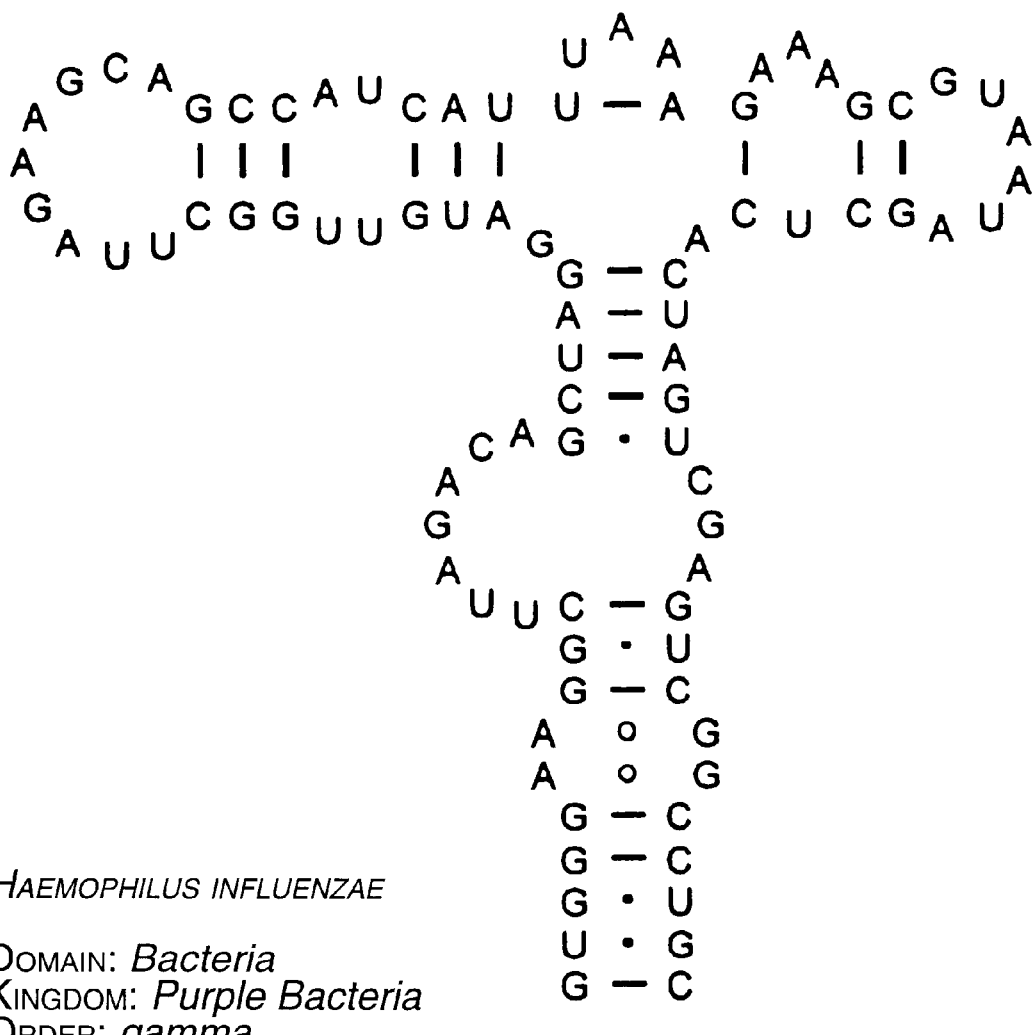
Figure 15D:
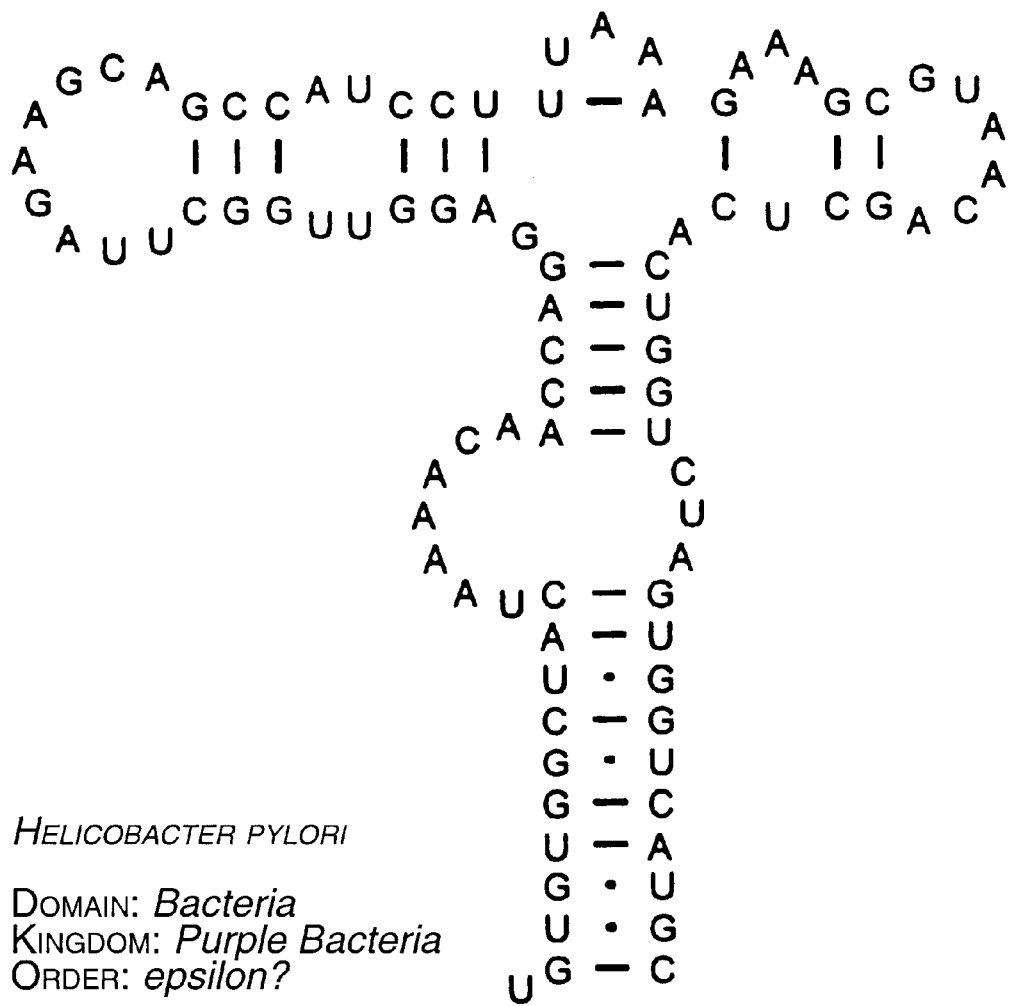
Figure 15E:
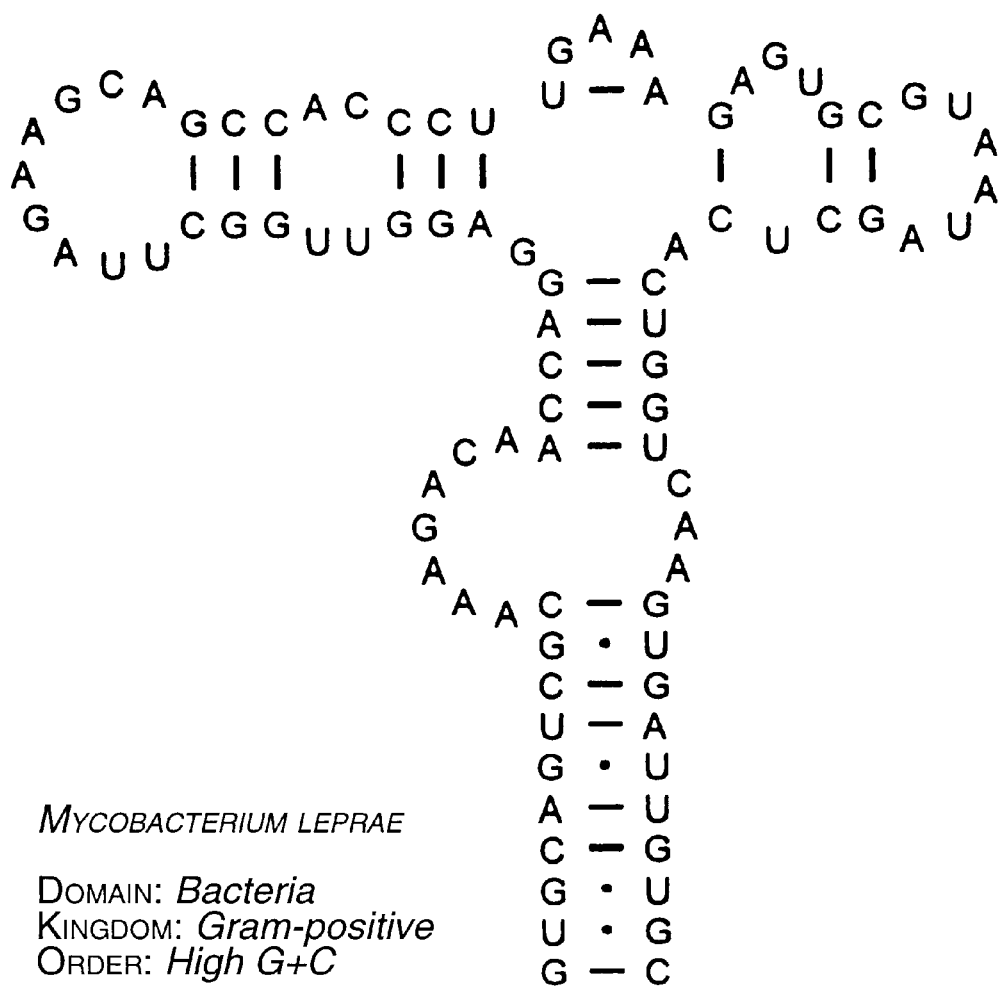
Figure 15F:
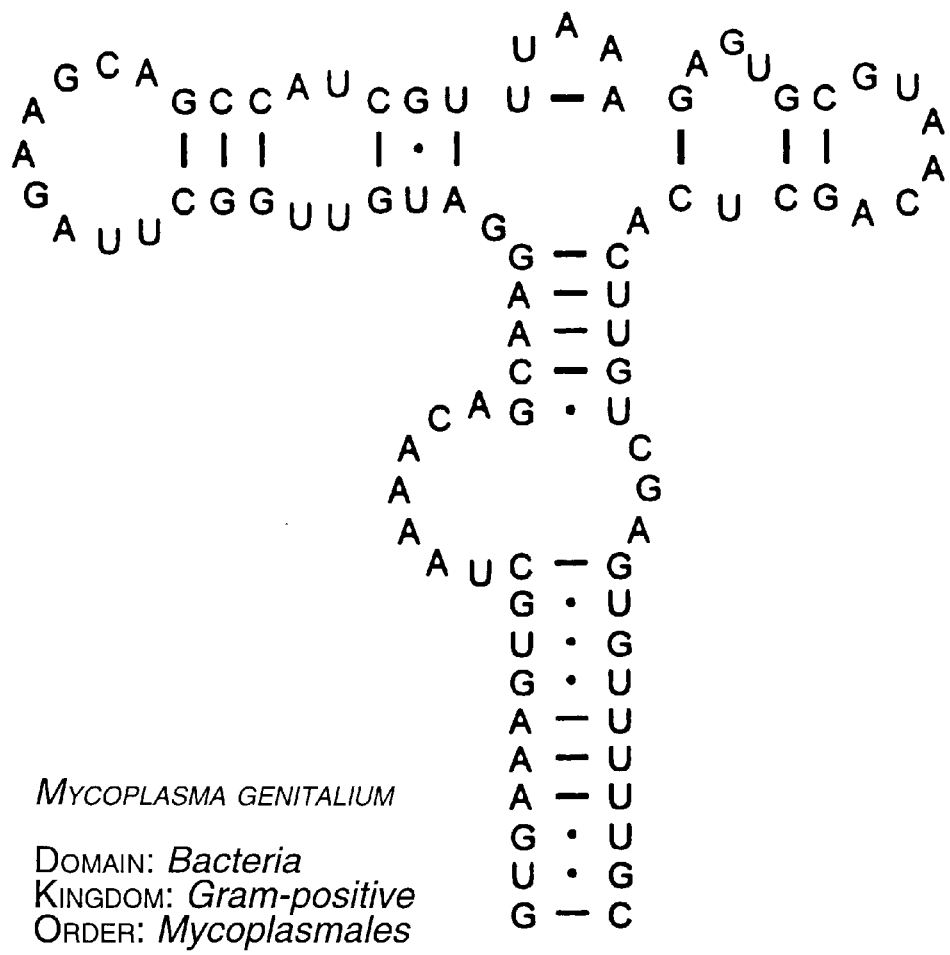

Target 16S and 23S rRNAs are shown in FIGS. 1 and 2, respectively. The sequence (5'-CCGUCACACCUUCGGGUGAAGUCGG -3'; SEQ ID NO: 1) used for the 16S A site binding studies was derived from 16S rRNA as depicted in FIG. 9. Examples for target RNA sequences that could be derived for the L1 binding site (the E site) in 23S rRNA (FIGS. 10 and 14), the GTPase center in 23S rRNA (FIGS. 11 and 15), and the spectinomycin site in 16S rRN A (FIGS. 12 and 16) are represented in the indicated figures.

Fluorescent Labeling

The target RNA and the antimicrobial may be fluorescently labeled for use according to the invention by any suitable method, preferably by covalent attachment of a fluorescent group. The labels may be any fluorescent label or fluorophore that does not interfere with the ability of the antimicrobial to interact with the target RNA and is able to show quenching and/or fluorescence resonance energy transfer with the corresponding label on the target RNA.

The target RNA may be fluorescently labeled at any suitable position. For instance, the fluorescent group or quenching group is placed on or adjacent to the 5' end of the target RNA. Alternatively, the fluorescent or quenching group is placed on or adjacent to the 5' end of one of a pair of oligonucleotides forming an RNA duplex, or the 5' end of one of the component oligonucleotides in RNA structure created by the annealing of three or more RNA oligonucleotides. In other instances, the fluorescent group may be placed on or adjacent to the 3' end of one of the synthetic RNA molecules. Fluorescent dyes can be introduced specifically at the 3' end of transcribed RNA by oxidation with periodate followed by coupling with the dye-hydrazide.

The fluorescent group also may be placed within the chain of the synthetic RNA molecules, for instance by incorporation of a fluorescent nucleotide derivative, modification of a nucleotide or substitution of a nucleotide by a fluorescent molecule. For example, tetramethylrhodamine (TAMRA) can be introduced into synthetic RNA by incorporating the modified deoxy-uridine phosphoramidite (5'-Dimethoxytrityloxy-5-[N-((tetramethyl-odaminyl)-aminohexyl)-3-acryimido]-2'-deoxy-uridine-3'-[(2-cyanoethyl)-(N,N-diisopropyl)]-phosphoramidite). Fluorescein may be incorporated in an analogous way with: 5'-Dimethoxytrityloxy-5-[N-((3',6'-dipivaloylfluoresceinyl)-aminohexyl)-3-acryimido]-2'-deoxy-uridine-3'-[(2-cyanoethyl)-(N,N-diisopropyl)]-phosphoramidite. The DABCYL group may also be incorporated using 5'-Dimethoxytrityloxy-5-[N-((4-(dimethylamino)azobenzene)-aminohexyl)-3-acryimido]-2'-deoxy-uridine-3'-[(2-cyanoethyl)-(N,N-diisopropyl)]-phosphoramidite. More generally, a free amino group may be reacted with the active ester of any dye; such an amino group may be introduced by the inclusion of the modified uridine 5'-Dimethoxytrityl-5-[N-(trifluoroacetylaminohexyl)-3-acrylimido]-2'-deoxy-uridine,3'-[(2-cyanoethyl)-(N,N-diisopropyl)]-phosphoramidite. The incorporation of a single deoxy-uridine often does not significantly perturb RNA structure and the modification at the 5 position of the base allows for normal base-pairing.

It is also possible to include more than one fluorescent label on a synthetic RNA target molecule without departing from the scope the invention. For instance, a target RNA molecule is labelled with 2 fluorescent groups, with one group placed adjacent to the 5' end of the target RNA sequence and a second fluorescent group placed adjacent to the 3' end of the target RNA sequence. In other embodiments, two or more fluorescent groups are placed adjacent to the 5' and/or 3' ends of the target RNA molecule and/or at internal sites in the RNA target sequences. Multiply labelled target RNAs can be used to increase the intensity of the signals detected in the assay.

Antimicrobial molecules that bind to RNA contain functional groups that render them amenable to derivatization by fluorescent dyes. The antimicrobials contain primary and secondary amines, hydroxyl, nitro and carbonyl groups. Methods that can be used to make fluorescent antimicrobial ligands are described below.

A number of chemical reactions can be applied to the fluorescent labelling of amines including but not limited to the following, where the fluorescent dye is conjugated to the indicated reactive group:

| Functional Group | Reaction | Product |
| --- | --- | --- |
| Amine | dye-isothiocyanates | Thiourea |
| Amine | dye-succinimidyl ester | Carboxamide |
| Amine | dye-sulfonyl chloride | Sulphonamide |
| Amine | dye-aldehyde | Alkylamine |

Antimicrobials containing amine groups that are appropriate for the introduction of fluorescent dyes include but are not limited to those listed in Table 1.

A number of chemical reactions can be applied to the fluorescent labelling of ketone groups including but not limited to the following, where the fluorescent dye is conjugated to the indicated reactive group:

| Functional Group | Reaction | Product |
| --- | --- | --- |
| Ketone | dye-hydrazides | Hydrazones |
| Ketone | dye-semicarbazides | Hydrazones |
| Ketone | dye-carbohydrazides | Hydrazones |
| Ketone | dye-amines | Alkylamine |

Antimicrobials containing ketone groups that are appropriate for the introduction of fluorescent dyes include but are not limited to those listed in Table 2.

A number of chemical reactions can be applied to the fluorescent labelling of aldehyde groups including but not limited to the following, where the fluorescent dye is conjugated to the indicated reactive group:

| Functional Group | Reaction | Product |
| --- | --- | --- |
| Aldehyde | dye-hydrazides | Hydrazones |
| Aldehyde | dye-semicarbazides | Hydrazones |
| Aldehyde | dye-carbohydrazides | Hydrazones |
| Aldehyde | dye-amines | Alkylamine |

Antimicrobials containing aldehyde groups that are appropriate for the introduction of fluorescent dyes include but are not limited to those listed in Table 3.

Dehydrobutyrene and dehydroalanine moieties have characteristic reactions that can be utilized to introduce fluorophores, as illustrated but not limited to the following, where the fluorescent dye is conjugated to the indicated reactive group:

| Functional Group | Reaction | Product |
|---|---|---|
| Dehydrobutyrine | dye-sulphydryl | Methyl lanthionine |
| Dehydroalanine | dye-sulphydryl | Lanthionine |

Antimicrobials containing aldehyde groups that are appropriate for the introduction of fluorescent dyes include but are not limited to those listed in Table 4.

Useful fluorophores (in addition to those listed in Tables 5 and 6) include, but are not limited to: Texas Red™ (TR), Lissamine™ rhodamine B, Oregon Green™ 488 (2',7'-difluorofluorescein), carboxyrhodol and carboxyrhodamine, Oregon Green™ 500, 6-JOE (6-carboxy-4',5'-dichloro-2',7'-dimethyoxyfluorescein, eosin F3S (6-carobxymethylthio-2', 4',5',7'-tetrabromo-trifluorofluorescein), cascade blue™ (CB), aminomethylcoumarin (AMC), pyrenes, dansyl chloride (5-dimethylaminonaphthalene-1-sulfonyl chloride) and other napththalenes, PyMPO, ITC (1-(3-isothiocyanatophenyl) -4-(5-(4-methoxyphenyl)oxazol-2-yl)pyridinium bromide).

Donor/Acceptor Pairing

Contact between the pair of indicator molecules may occur in solution (e.g., a test tube, dish or well of a microtitre plate) or, alternatively, either the antimicrobial molecule or the target RNA molecule may be adhered to a solid support (e.g. an affinity gel, matrix, or column) by covalent or non-covalent linkages using methods known in the art. The support bound target RNA or antimicrobial molecule is then mixed with a solution containing the other compound of the indicator pair.

When the antimicrobial and RNA target are mixed, they can form a complex which brings the donor and acceptor groups into proximity. The "fluorescence" of, or light emitted from, the complex formed between the antimicrobial molecule and the target RNA is altered by fluorescence resonance energy transfer (FRET). "FRET" is a distance-dependent interaction between the electronic exited states of two dye molecules in which excitation is transferred from a donor molecule to an acceptor molecule. FRET is dependent on the inverse sixth power of the intermolecular separation, making it useful over distances comparable to the dimensions of biological macromolecules and obtainable in the complexes formed between the antimicrobial molecules and target RNA molecules in the method of this invention. In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization.

The donor group may be attached to either the target RNA or to the antimicrobial. When the donor is attached to the target RNA, the complementary acceptor is attached to the antimicrobial; conversely, when the donor is attached to the antimicrobial, the complementary acceptor is attached to the target RNA.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro (isobenzofuran-1(3H), 9'-(9H)xanthene)-5-carboxylic acid, 3', 6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid ]); 6-Hexachloro-Fluorescein ([4,7,2',4',5',7'-hexachloro-(3',6'-dipivaloylfluorsceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl) -3, 6-bis(dimethylamino); EDANS (5-((2-aminoethyl) amino)naphthalene-1-sulfonic acid); 1,5-IAEDANS (5-((((2-iodoacetyl)amino)ethyl) amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), as well as suitable derivatives thereof.

According to some methods of the invention, the RNA target molecule has been specifically labelled by a donor/acceptor that is different from the acceptor/donor that is present on the antimicrobial. Preferred combinations of donors and acceptors are listed as, but not limited to, the donor/acceptor pairs shown in Tables 5 and 6 (which includes values for $R_o$—the distance at which 50% of excited donors are deactivated by FRET).

Reference herein to "fluorescence"or "fluorescent groups" or "fluorophores" include luminescence, luminescent groups and suitable chromophores, respectively. In the present invention, the target RNA and antimicrobial may be labelled with luminescent labels and luminescence resonance energy transfer is indicative of complex formation. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin, 1995). Luminescent groups containing lanthanide ions can be incorporated into nucleic acids utilizing an 'open cage' chelator phosphoramidite. Table 5 gives some preferred luminescent groups.

In certain embodiments of the invention, the target RNA and antimicrobial may also be labelled with two chromophores, and a change in the absorption spectra of the label pair is used as a detection signal, as an alternative to measuring a change in fluorescence.

Measurable Changes

In the method of the present invention, the labelled antimicrobial is capable of binding to the labelled target RNA, thereby forming a complex in which the donor present on one molecule comes into proximity with the acceptor on the other molecule. This results in reduced fluorescence of the complex compared to the uncomplexed fluorescence exhibited by the antimicrobial and/or target RNA when free in solution.

In the method of the invention, fluorescence intensity of the antimicrobial, the fluorescence intensity of the RNA target and the fluorescence intensity of the complex is measured at one or more wavelengths with a fluorescence spectrophotometer or microtitre plate reader. It is generally preferred that the antimicrobial and RNA target form a one-to-one complex and equimolar concentrations of antimicrobial and RNA target are present in the binding reaction. However, an excess of one reagent may be used without departing from the scope of the invention.

In some embodiments, a fraction of the antimicrobial molecules and RNA target molecules in the binding reaction can be replaced by unlabelled analogues. The optimal proportions of labelled and unlabelled antimicrobial and RNA target molecules can be determined by titration of the different components and measuring the optimal concentrations required in order to obtain maximal FRET or fluorescent quenching.

The labelled RNA and labelled antimicrobial molecules are then mixed with a test compound and the fluorescence in the mixture is measured. If the test compound is able to bind to the region of the target RNA that binds to the antimicrobial, then a fraction of the antimicrobial will be prevented from binding to the RNA target. The proportions of the free antimicrobial, free test RNA and complex can be quantitatively determined by comparing the spectral properties of the complex, partially dissociated complex and the uncomplexed target RNA and antimicrobials. The amount of antimicrobial displacement will be a function of the relative affinity of the test compound for the target RNA compared to the antimicrobial and the relative concentrations of the two molecules in the sample. Preferably, a variety of different concentrations of the molecule to-be-tested are compared to generate a binding curve. Saturation of the target RNA is reached when the fluorescence emission of the antimicrobial or RNA target molecule is restored to the levels obtained from the free molecules.

The concentration of compounds binding to RNA targets can be determined with a fluorescence standard curve depicting the fluorescence of the labelled antimicrobial and target RNAs with varying known concentrations of competing unlabelled test compound.

In some embodiments of the invention, fluorescence resonance energy transfer between the donor and acceptor may give rise to a distinct fluorescence emission spectrum of the complex which can be compared to the fluorescence emission spectra of the separate antimicrobial and target RNA molecules.

In some embodiments of the invention, FRET is detected by steady state measurements of the integrated emission intensity of the donor (i.e. the fluorescent dye that is excited by the light source used in the spectral measurement) and/or the acceptor (i.e. the fluorescent dye which has a absorption spectrum that overlaps the emission spectrum of the donor). In addition, FRET may be detected by time-resolved measurements in which the decay of donor fluorescence is measured after a short pulse of excitation. In certain embodiments of the invention the donor is excited at a wavelength that does not itself result in efficient excitation of the acceptor, and FRET is detected by measuring the excitation of the acceptor due to transfer of a photon from the donor.

Typically, it is preferable to look for a signal (a positive), rather than for the absence of a signal (a negative) in an assay of the invention, but it will be appreciated that either or both may be followed.

Test Compound

The present invention may be used to identify an antimicrobial or compound capable of binding to any target RNA, preferably as part of a screening process.

As used herein, the term "test compound" refers to an agent comprising an antimicrobial, compound, molecule, or complex, that is being tested for its ability to bind to a target RNA. Test compounds can be any agent, including, but not restricted to, antimicrobial, peptides, peptoids, proteins, lipids, metals, nucleotides, nucleosides, small organic molecules, polyamines, and combinations and derivatives thereof. Small organic molecules have a molecular weight of more than 50 and less than about 2,500 daltons, and most preferably between about 300 and about 800 daltons. Complex mixtures of substances, such as extracts containing natural products, or the products of mixed combinatorial syntheses, can also be tested and the component that binds to the target RNA can be purified from the mixture in a subsequent step. The test compound may be a close structural relative of a known antimicrobial that binds to the target RNA with higher affinity than the known drug.

Test compounds may be derived from large libraries of synthetic or natural compounds. For instance, synthetic compound libraries are commercially available from Maybridge Chemical Co. (Trevillet, Cornwall, UK) or Aldrich (Milwaukee, Wis.). Alternatively, libraries of natural compounds in the form of bacterial, fungal, plant and animal extracts may be used. Additionally, test compounds may be synthetically produced using combinatorial chemistry either as individual compounds or as mixtures.

Order of Mixing

A significant advantage of the method of the invention is that it measures equilibrium binding. The invention also exploits the principle that the most reliable type of assays for RNA-binding compounds are based on competition assays between the RNA-binding protein and the drug candidates.

In preferred embodiments of the invention, the target RNA, the antimicrobial, and the test compound are mixed, and the fluorescence of the mixture is compared to standards. Competitive inhibitors of the binding of the antimicrobial prevent the formation of the antimicrobial-target complex and therefore increase the amount of free target RNA and free antimicrobial in the reaction. Since the fluorescence of the free RNA and antimicrobial molecules is unquenched, the overall fluorescence in the reaction increases in direct relation to the amount of test compound in the binding reaction and its relative affinity for the target RNA compared to the antimicrobial.

In some embodiments of the invention, the test compound is first mixed with the labelled RNA in order to form a complex in the absence of the labelled antimicrobial, and the antimicrobial is then added. Since the antimicrobial will only be able to bind to the free RNA in the reaction, there will be a reduced amount of complex formed between the antimicrobial and the target RNA compared to the amount of complex formed in the absence of test compound. As a result, the fluorescence of the mixture containing the test compound will be increased compared to a similar mixture prepared in the absence of the test compound.

In other embodiments, a complex is pre-formed between the labelled RNA and the labelled antimicrobial before addition of the test compound. If the test compound is able to disrupt the complex formed between the labelled-RNA and the labelled-antimicrobial, or alter the equilibrium binding state by binding to RNA that has dissociated from the antimicrobial, the amount of complex in the reaction will be reduced and the overall fluorescence of the mixture will increase.

In some circumstances, the test compound may itself be fluorescent and/or be capable of quenching the fluorescent group present on the target RNA and/or the antimicrobial. In preferred embodiments of the invention, the fluorescence of standards containing the test compound on its own, and in pairwise combinations with the target RNA or antimicrobial, are measured and these values are compared to the fluorescence of the complete test mixture containing the test compound, the fluorescent RNA and the antimicrobial.

Quenching of fluorescence arising from the RNA due to the binding of the test compound to the RNA will result in a decrease in the signal arising from the RNA that is not complexed to the antimicrobial, but will not affect the fluorescent signal arising from the group on the antimicrobial or the signal obtained from the RNA in a complex with the antimicrobial. In this circumstance it is preferable to configure the donor/acceptor pairs on the RNA and the antimicrobial such that an increase in the fluorescence of the antimicrobial is detectable when the formation of the complex between the antimicrobial and the RNA is blocked by the test compound.

Quantitative Nature of the Assay

An important feature of the invention is that the test compound competes for RNA binding against a specific pre-defined antimicrobial. This provides specificity in the assay and permits exclusion of compounds that bind to the target RNA but do not interfere with the binding of the antimicrobial. In preferred embodiments, the antimicrobials are designed to bind to discrete regions in the target RNA that are involved in biological activity or function, to permit identification of compounds that are likely to have biological or pharmaceutical activity.

The invention allows the measurement of the dissociation constant ($K_d$) between the antimicrobial and the target RNA. $K_d$ is defined by equation [1]:

$$K_d = \frac{[R_f][P_f]}{[RP]}$$

Where $[R_f]$ is the concentration of free RNA, $_f[P]$ is the concentration of free antimicrobial, and $[RP]$ is the concentration of the complex.

$K_d$ may be determined experimentally by incubating a predetermined concentration of target RNA together with a series of concentrations of antimicrobial. An increase in the formation of complexes of the antimicrobial and the target RNA in solution results in a progressive increase in FRET and/or quenching. As the concentration of antimicrobial increases the spectral values approach a maximal value asymptotically due to the formation in solution of the antimicrobial-target RNA complex. In some embodiments of the invention the $K_d$ of an antimicrobial is determined by incubating a pre-determined concentration of antimicrobial together with a series of concentrations of target RNA.

The value for $K_d$ is preferably determined by fitting the experimental data to a binding curve derived from equation [1] by least-squares fit regression analysis. Alternatively, $K_d$ values can be approximated by graphical analysis of the data using double reciprocal (Scatchard) or similar plots. $K_d$ values are physical-chemical constants that define the affinity between the antimicrobial and the target RNA. The relative affinities of different antimicrobial for target RNAs may be determined by comparing measured $K_d$ values.

In preferred embodiments, the binding constant of a test compound relative to the antimicrobial ($K_i$), is measured by incubating a pre-determined concentration of target RNA and antimicrobial, together with a series of different compound concentrations. The concentrations of target RNA and antimicrobial molecules are chosen to give a measurable amount of complex formation; preferably greater than 10% complex formation and most preferably greater than 50% complex formation. The most preferable starting conditions are obtained using equimolar concentrations of antimicrobial and target RNA molecules at concentrations that are greater than $5 \times K_d$ of the antimicrobial-target RNA. Under these circumstances essentially all of the antimicrobial and target RNA is found in the complex.

$K_i$ is then determined by measuring the inhibition of complex formation as a function of the amount of test compound added. A formal description of the binding equilibrium is as follows:

$$[R]+[P] \rightleftharpoons [RP]; [R]+[I] \rightleftharpoons [RI]$$

where $[R]$ is the target RNA concentration, $[P]$ is antimicrobial concentration, $[I]$ is the inhibitor (i.e., test compound) concentration, $[RP]$ is the concentration of the complex formed between the antimicrobial and the target RNA; and $[RI]$ is the concentration of the complex formed between the test compound and the target RNA. It follows that:

$$K_d = \frac{[R_f][P_f]}{[RP]} \quad \text{and}$$

$$K_i = \frac{[R_f][I_f]}{[RI]}$$

where $K_d$ is the dissociation constant between the target RNA and the antimicrobial, $K_i$ is the dissociation complex between the test compound and the target RNA, $[R_f]$ is the free RNA concentration; $[P_f]$ is the free antimicrobial concentration; and If is the free test compound (inhibitor) concentration.

Hence $[R_f] = [R] - [RP] - [RI]$;

$[P_f] = [P] - [RP]$; and $[I_f] = [I] - [RI]$.

Combining the equations yields the cubic equation [2] in which $K_d$ and $K_i$ are related to the experimentally determined values for $[R]$, $[P]$, $[I]$ and $[RP]$:

$$[RP]^3(K_d - K_i) +$$
$$[RP]^2\{K_d(K_i - K_d) + (K_i - K_d)[R] + (2K_i - K_d)[P] +$$
$$K_d[I]\} + [RP][P]\{(K_d - 2K_i)[R] - K_i[P] - K_d[I] -$$
$$K_d K_i\} + K_i[R][P]^2 = 0$$

equation [2]

Solutions of equation [2] by regressional analysis yield values for $K_i$. However, in practice, it is preferable to simplify equation [2] to a quadratic equation by approximating certain of the starting conditions. A typical simplification occurs when $K_i >> K_d$ and therefore the experimental inhibitor concentration is much greater than the total RNA, under conditions where the antimicrobial is partially displaced from the RNA by inhibitor, hence, $[I_f] \approx \{I\}$. Reworking the above derivation, with this simplification, then yields the quadratic equation:

$$K_d\left(1 + \frac{[I]}{K_i}\right) + [P] + [P][R] = 0 \qquad \text{equation [3]}$$

which has the solution $$[RP] = \frac{\left[K_d\left(I + \frac{[I]}{K_i}\right) + [P] + [R]\right] - \sqrt{\left[K_d\left(I + \frac{[I]}{K_i}\right) + [P] + [R]\right]^2 - 4[P][R]}}{2}$$ equation [4]

If a value of $K_d$ has already been determined for the antimicrobial, values of $K_i$ for various inhibitors can be determined by non-linear regression analysis of data of [RP] against [I].

An alternative method to estimate $K_i$ which has been applied in the examples given below, is to fit the data to the equation:

$$FI = [B_{max}][K_i] + [I]$$

where: FI is the experimentally measured fluorescence intensity; $B_{max}$ is the maximal fluorescent signal (determined by measuring the fluorescence of the antimicrobial combined with inhibitor); and [I] is the inhibitor concentration. This simplified method ignores the effect of antimicrobial binding on reducing the free RNA concentration, but is a useful simplification when $K_i >> K_d$.

Library Screening (Including High Throughput Screens)

The present invention also encompasses high-throughput screening methods for identifying compounds that bind to a target RNA. Preferably, all the biochemical steps for this assay are performed in a single solution in, for instance, a test tube or microtitre plate, and the test compounds are analyzed initially at a single compound concentration. For the purposes of high throughput screening, the experimental conditions are adjusted to achieve a proportion of test compounds identified as "positive" compounds from amongst the total compounds screened. The assay is preferably set to identify compounds with an appreciable affinity towards the target RNA e.g., when 0.1% to 1% of the total test compounds from a large compound library are shown to bind to a given target RNA with a $K_i$ of 10 μM or less (e.g. 1 μM, 100 nM, 10 nM, or less).

Kits Useful According to the Invention

The invention also provides a kit for determining whether a test compound binds to a target RNA, the kit comprising (a) a target RNA labelled with a donor group or an acceptor group and (b) an antimicrobial labelled with a complementary acceptor or donor group, wherein the antimicrobial and the target RNA are capable of binding to each other in an orientation that permits the donor group to come into sufficient proximity to the acceptor group to permit fluorescent resonance energy transfer and/or quenching. The kits will include the components useful in the inventive methods, as well as packaging materials therefor.

Measurement of RNA Binding Compound

The invention may be embodied as a clinical assay or method for determining the presence of an RNA-binding compound in a biological sample such as the serum or tissues of a subject. Many drugs, including RNA-binding compounds such as antibiotics, are routinely assayed for their serum levels when administered to patients to prevent administration of toxic levels of compounds.

The invention thus provides a method for determining the amount of a predetermined RNA-binding compound in a subject or biological sample. In this method a complex consisting of a labelled target RNA specifically bound to a labelled antimicrobial is mixed with a sample to be analyzed (e.g., a serum sample or tissue extract from a subject). The level of RNA-binding compound in the sample is determined by comparing the level of fluorescence emitted by the labelled target RNA and/or labelled antimicrobial in the presence of the sample with the level of fluorescence obtained using a known amount of the RNA-binding compound of interest. In some embodiments of this method, the antimicrobial is unrelated to the RNA-binding compound of interest; in other embodiments it is a fluorescent version of the compound of interest.

The invention also provides a kit for determining the level of an RNA-binding compound of interest in a subject or sample, comprising (a) RNA labelled with a donor group or an acceptor group and which is specifically bound by the compound of interest (b) a antimicrobial labelled with a complementary acceptor or donor group, wherein the antimicrobial and the target RNA are capable of binding to each other in an orientation that permits the donor group to come into sufficient proximity to the acceptor group to permit fluorescent resonance energy transfer and/or quenching. The kit preferably further comprises a sample of the compound of interest in unlabelled and uncomplexed form, with which to prepare a standard fluorescence curve.

Typically, a serum or blood sample, or a tissue extract, is taken from a patient and contacted with the complex. The fluorescence of the complex is then measured and compared to a standard curve depicting the fluorescence of the complex in the presence of known concentrations of the RNA-binding compound of interest.

In this, and other, aspects of the invention, it may be desirable to add a ribonuclease inhibitor to the sample or to the mixture of the sample and complex to prevent degradation of the RNA. As an alternative, the fluorescently labelled target RNA could be protected by the inclusion of modified bases, sugars or backbone modifications as described above.

EXAMPLES

The following examples illustrate the preferred modes of making and practicing the present invention, but do not limit the scope of the invention.

The method of the invention is illustrated by the binding of a fluorescently labeled antibiotic to a fluorescently labelled RNA target and the competitive inhibition of binding by unlabelled antibiotic. The fluorescently labelled antibiotic used here is paramomycin, which contacts a specific region in the 16S rRNA A site (Fourmy et al., 1998). The fluorescently labelled RNA is a small, 25 nucleotide RNA that mimics the double helical region of the 16S A site that is bound by paramomycin. The ability to detect a competitive inhibitor of binding of the fluorescently labelled antibiotic is demonstrated with unlabeled antibiotic, either neomycin or paramomycin.

In further examples, the identification of model RNA targets that are useful according to the invention are described for the GTPase center of 23S rRNA, the L1 (E site) of 23S rRNA, and the spectinomycin binding site of 16S rRNA.

Example 1

Identifying a model sequence for the A site, the site of action for a number of aminoglycoside antibiotics.

Figure 5B:
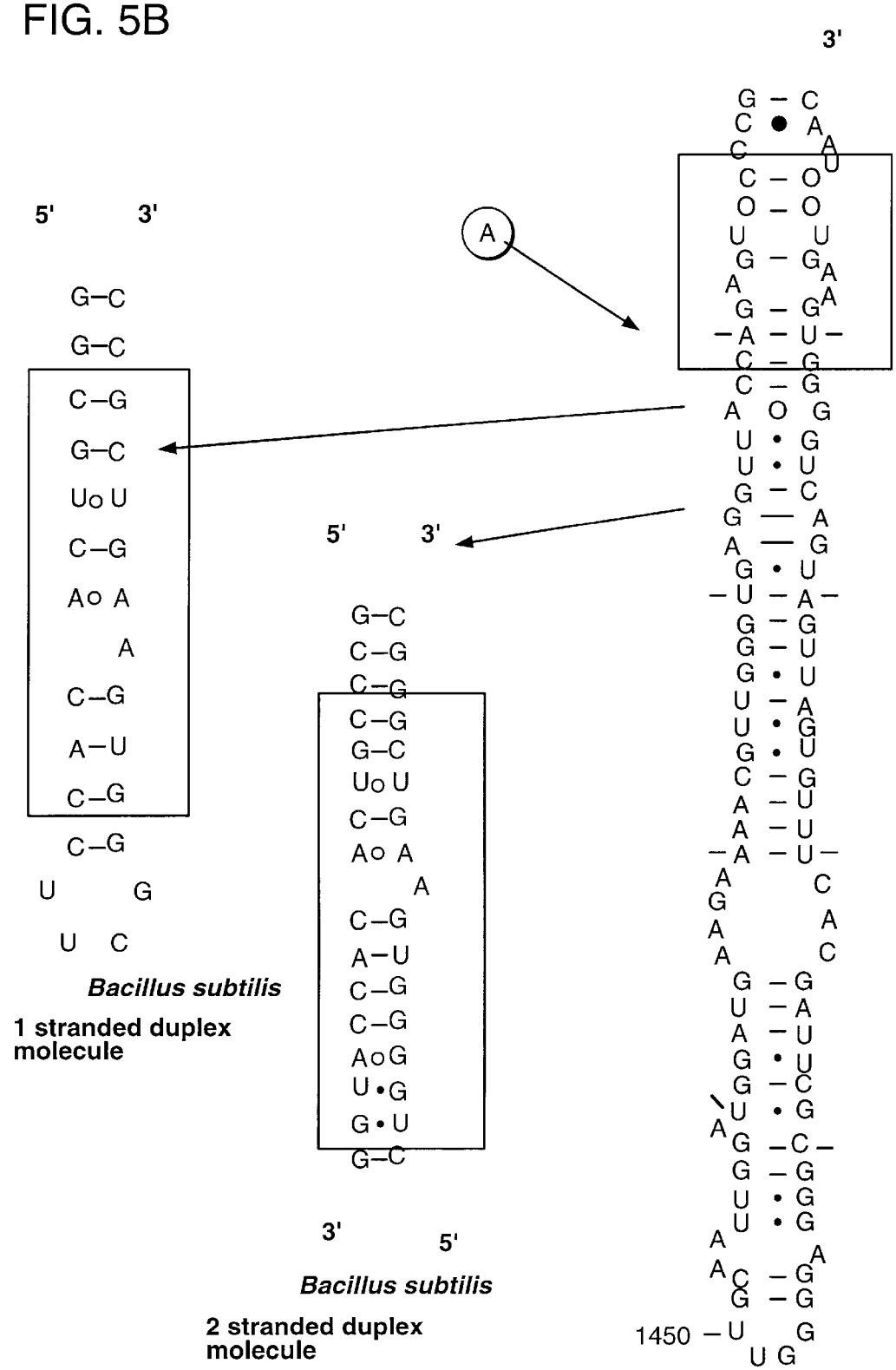
FIG. 5 shows the identification of a model sequence for the 16S rRNA A site *E. coli* A site, SEQ ID NO: 4; B. Subtilis A site, SEQ ID NO: 5; two-stranded duplex A site model, SEQ ID NO: 6; One-stranded duplex A site model, SEQ ID NO: 7.
Figures 13, 13A:
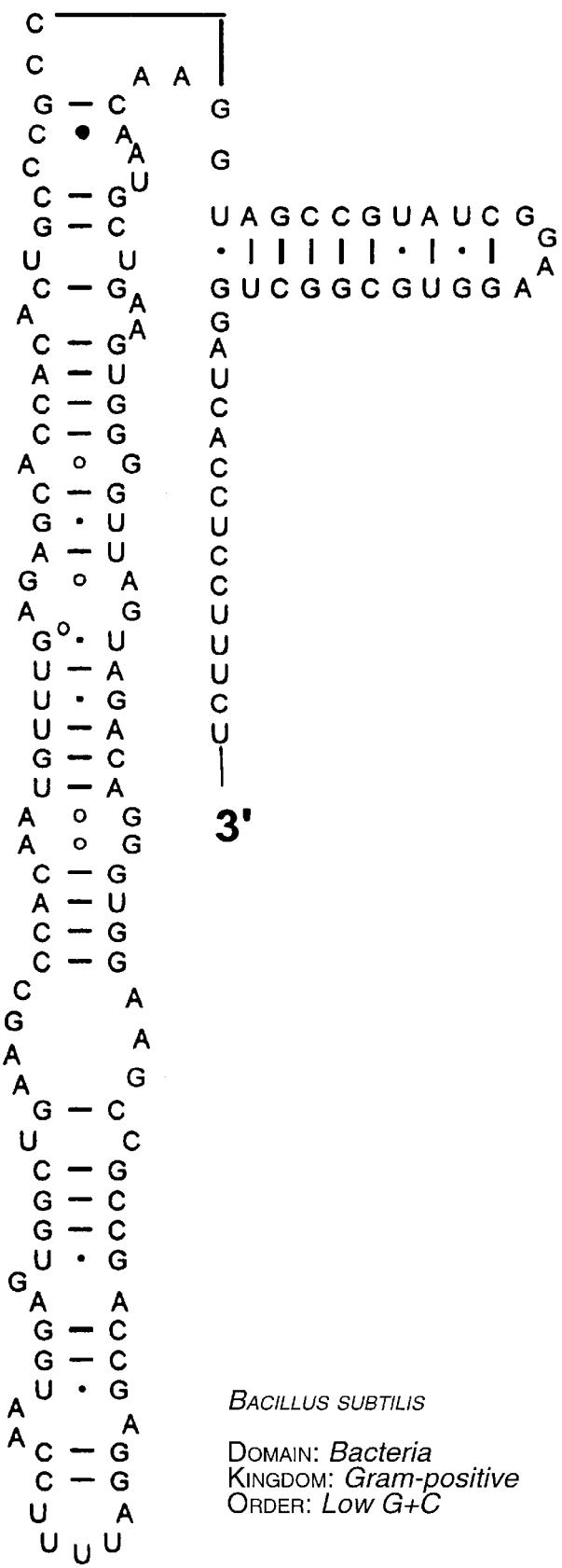
FIG. 13 Representative 16S rRNA sequences for the ribosomal A site, including the diverse organisms *Bacillus subtilis* (SEQ ID NO: 12), *Borrelia burgdorferi* (SEQ ID NO: 13), *Campylobacter sputorum* (SEQ ID NO: 14), *Mycoplasma hyopneumoniae* (SEQ ID NO: 15), *Clostridium innocuum* (SEQ ID NO: 16), *Haemophilus influenzae* (SEQ ID NO: 17), and *Mycoplasma genitalium* (SEQ ID NO: 18).
Figure 13B:
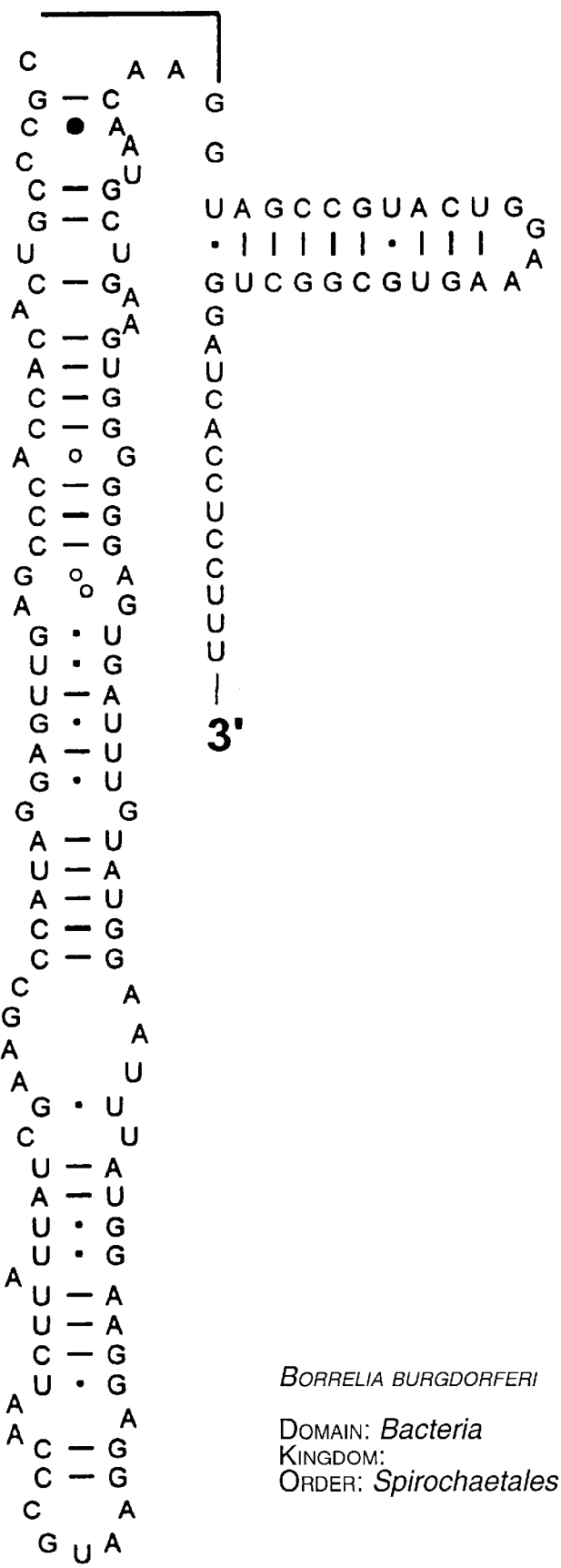
Figure 13D:
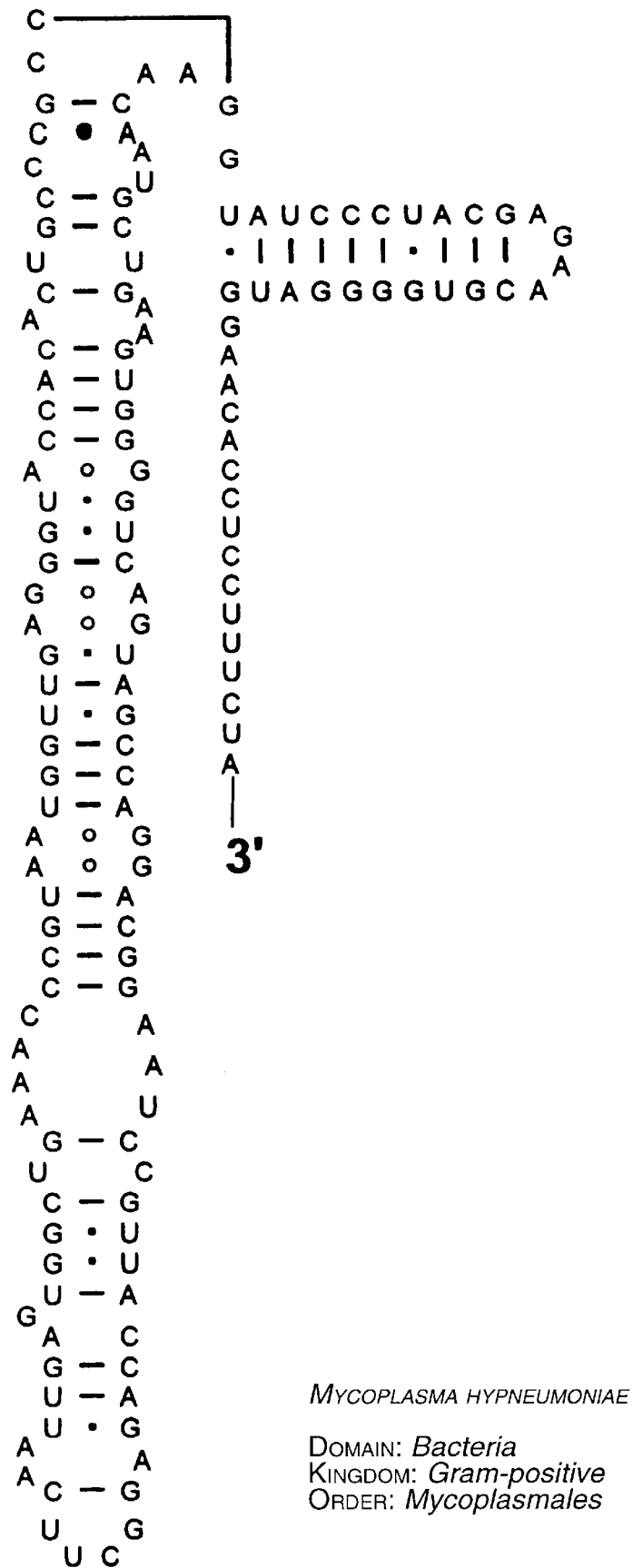
Figure 13E:
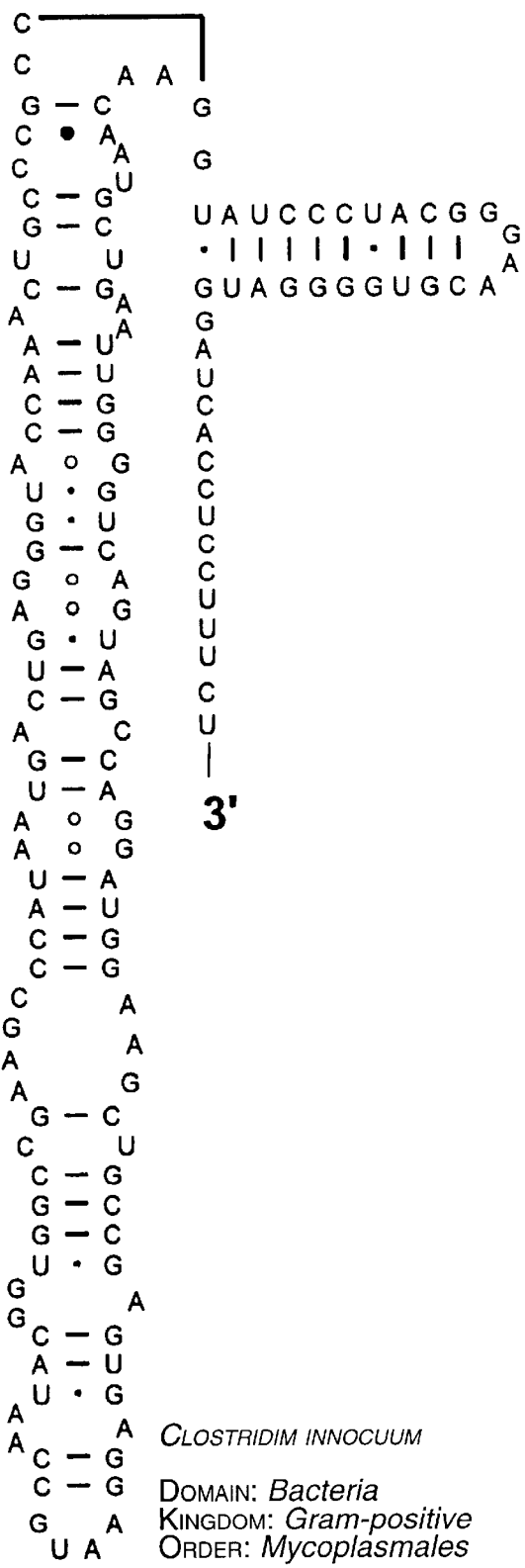
Figure 13F:
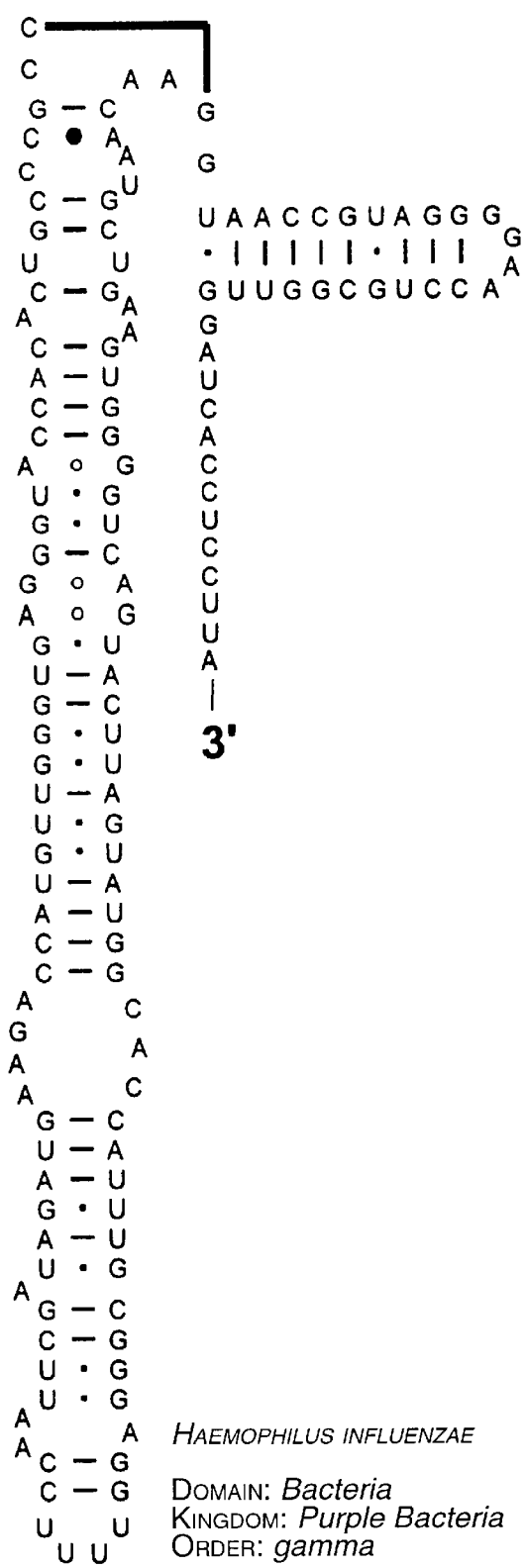
Figure 13G:
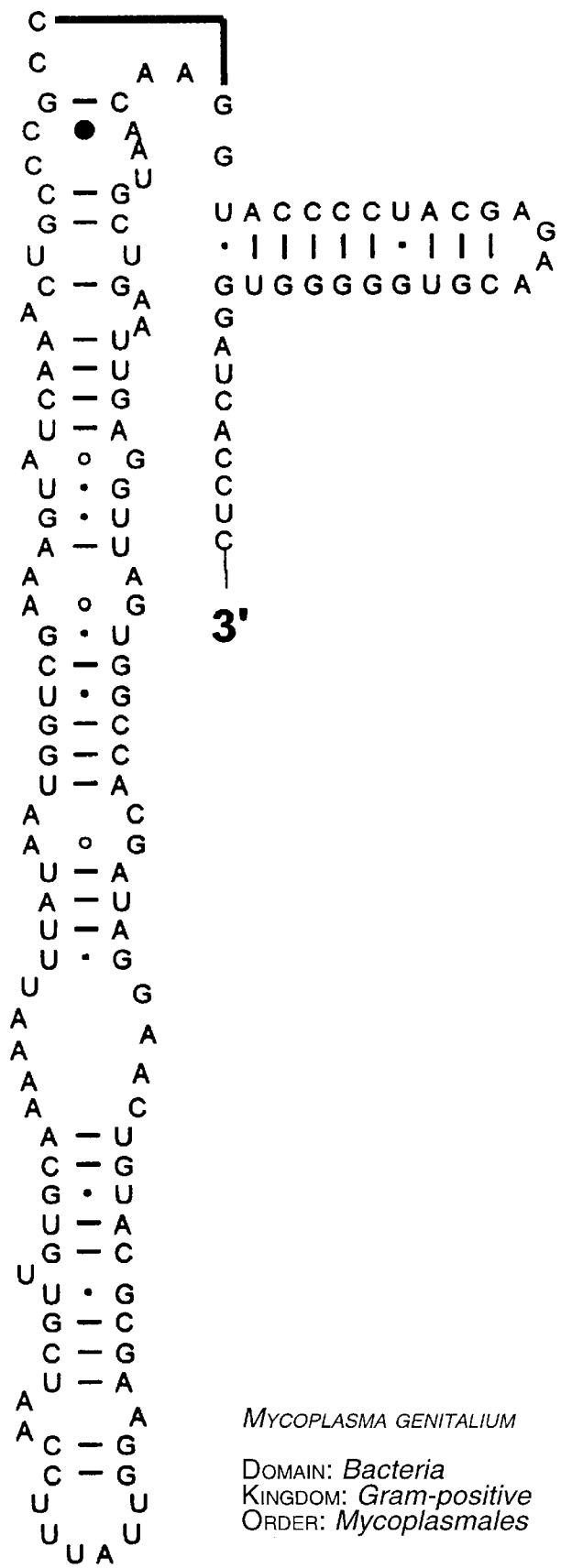

A number of antibiotics bind to the 16S rRNA in a variety of subregions of the rRNA, as illustrated in FIG. 1. Several aminoglycoside antibiotics, including paramomycin, bind the 16S rRNA in the subregion that is part of the ribosome acceptor site or A site, which is where amino acids (acylated to tRNAs) enter the ribosome to activate elongation of the nascent peptide (Spahn and Prescott, 1996, supra). The bacterial A site is highly conserved, as shown for several bacteria, including *Escherichia coli, Bacillus subtilis, Borrelia burgdorferi, Campylobacter sputorum, Mycoplasma hyopneumoniae, Clostridium innocuum, Haemophilus influenzae,* and *Mycoplasma genitalium* in FIGS. 5 and 13. The A site of the 16S rRNA can be reduced to generate small ribosomal sub domains that maintain the essential features of the RNA target (Gutell et al., 1993, Schnare et al., 1996), as shown in FIG. 5. The RNA target can be constructed from two small oligoribonucleotides (FIG. 5). Alternatively the ends of the double stranded RNA can be linked by a loop (FIG. 5).

1. Synthesis of DABCYL-labelled A Site RNA:

5'-CCGUCACACCUUCGGGUGAAGUCGG-3' (SEQ ID No. 1)

An oligoribonucleotide of the sequence shown above containing a 5' DABCYL group was synthesized by XERAGON using TOM phosphoramidite chemistry. It was purified by gel electrophoresis in a 20% acrylamide gel containing 7M urea, and extracted from the gel by electroelution (Fourmy et al., 1998).

2. Synthesis of Paramomycin-TAMRA

Paramomycin TAMRA was synthesized by reacting 55 mg paramomycin sulphate in sodium bicarbonate (6 mL 0.067M in 30% dimethyl formamide (DMF) with 5 mg 5-carboxytetramethyl rhodamine (in 1 mL DMF) over 12 hours at room temp. The solution was diluted and purified by anion exchange chromatography, and reversed phase HPLC (Wang et al., 1997).

3. Demonstration of Quenching Due to FRET Between TAMRA-labelled Paramomycin and DABCYL-labelled A Site RNA.

Figure 6:
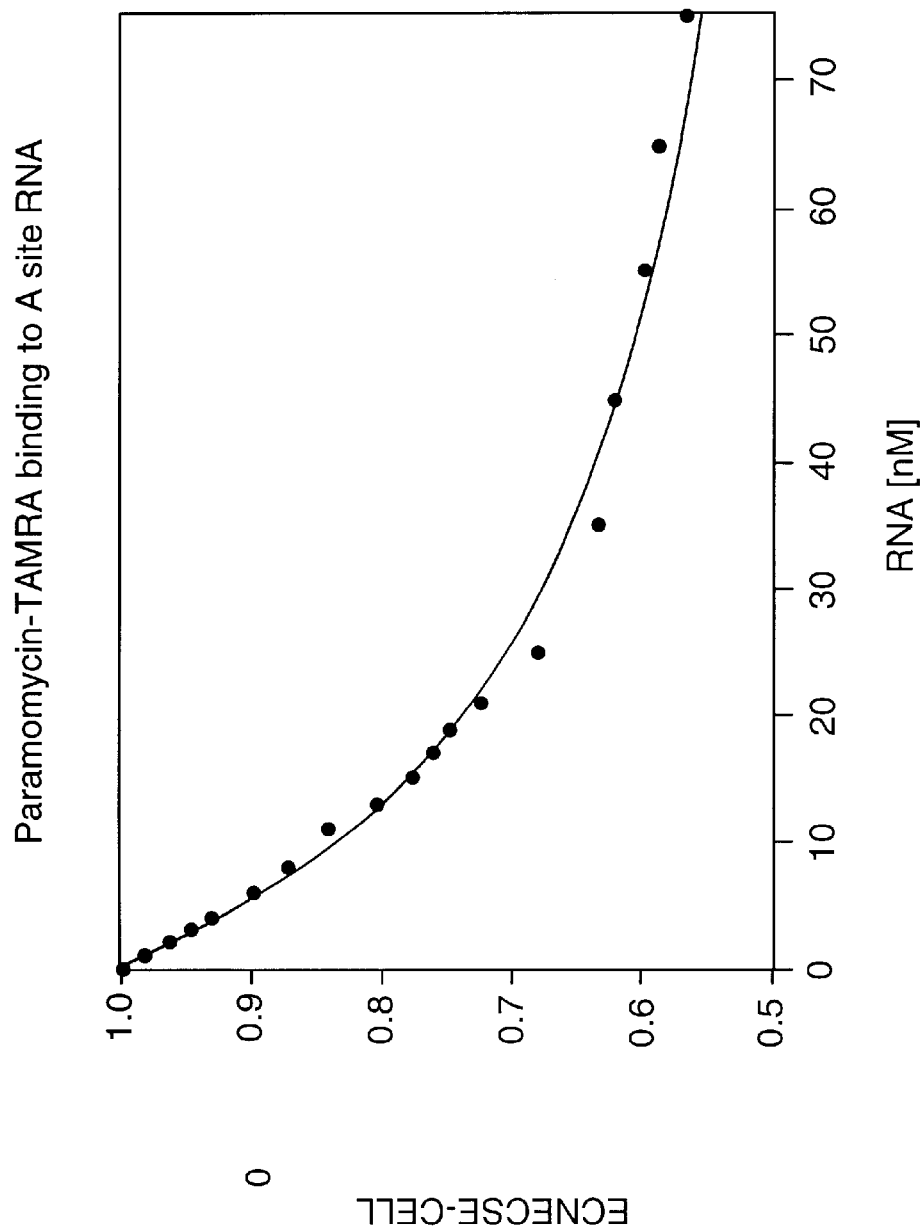
FIG. 6 shows the results of binding paramomycin-TAMRA to DABCYL-A site RNA.

FIG. 6 shows an experiment in which complex formation between a fluorescently labelled target RNA (DABCYL-labelled A site RNA) and a fluorescently labelled antibiotic (paramomycin-TAMRA) is measured by quenching in the complex due to fluorescent resonance energy transfer.

In this experiment, a small RNA derived from the 16S A site (see FIG. 5) was used as the target RNA or A site RNA. The interaction between paramomycin-TAMRA and A site RNA was measured utilizing paramomycin-TAMRA as a donor and DABCYL-A site RNA as an acceptor. Each measurement was made in a 2 mL cuvette, in a Perkin Elmer LS50B fluorimeter. Increasing amounts of DABCYL-A site RNA (corresponding to the amounts shown in FIG. 6) were added to a solution of 25 nM paramomycin-TAMRA in the presence of 50 mM Tris-HCl pH7.5, 80 mM KCl, 0.1% DMSO 0.00007% Triton X-100 and 0.5 ug/mL BSA. For each titration point emission spectra were acquired using a fixed wavelength of 544 nm with the excitation slits set to 5 nm and the emission slits set to 5 nm. Emission spectra were acquired over the range 570–600 nm. This range encompasses the emission spectrum of the donor (TAMRA). As shown in FIG. 6, a reduction in donor intensity was observed, which is due to fluorescence resonance energy transfer taking place between the two dyes upon the antibiotic binding to the A site RNA. The donor ratio presented is the difference in donor intensity on addition of DABCYL-A site RNA stock solution as a proportion of the total donor intensity in the absence of acceptor.

The results of the experiment presented in FIG. 6 demonstrate that complex formation between a fluorescently-labelled antimicrobial and a fluorescently-labelled target RNA is quantitatively measured according to the invention by quenching due to fluorescent resonance energy tranfer.

Example 2

Binding of paramomycin-TAMRA to A site RNA measured in a fluorescent plate reader.

Figure 7:
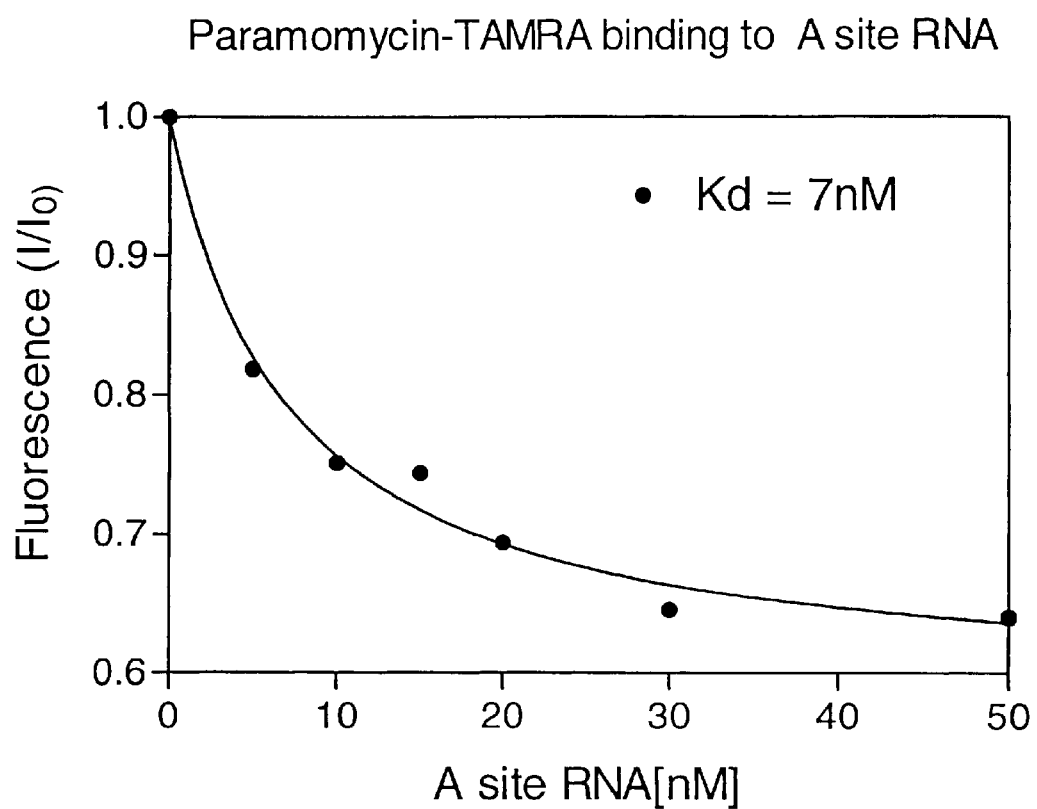
FIG. 7 shows the results of binding paramomycin-TAMRA to DABCYL-A site RNA as measured in a fluorescent plate reader.

To facilitate screening of competitive binding by the antimicrobial-RNA FRET assay, test compounds (antimicrobials) are measured in plates containing multiple wells. To demonstrate the ability of the assay to be utilized in this format, measurements were made in a 96-well plate reader (Wallac victor) with a fixed wavelength of 544 nm and emission at 590 run, as shown in FIG. 7.$I_0$ was determined by an initial measurement of a 95 μL solution of 25 nM paramomycin-TAMRA in the presence of 50 mM Tris-HCl pH7.5, 80 mM KCl, 0.1% DMSO 0.00007% Triton X-100 and 0.5 μg/mL BSA. I, (the final measurement) was then measured following the addition of 5 μL of a 20×DABCYL-A site RNA stock solution (corresponding to the amounts shown in FIG. 7). In the assay performed in the 96-well plate reader, quenching by FRET between the TAMRA-labelled paramomycin and DABCYL-labelled A site RNA was observed (FIG. 7) and is similar to the quenching observed for the FRET assay that was measured in cuvettes (FIG. 6). The invention is therefore applicable for screening of competitive binding by test compounds in a multiple well assay.

Example 3

Inhibition of paramomycin-TAMRA to A site binding by 10 μM Neomycin.

In the method of this invention, the ability of compounds to bind to rRNA is measured by competition binding assays involving an antimicrobial/target RNA pair and the compound to be tested. An important illustration of the method is to demonstrate that unlabelled antimicrobials can act as competitive inhibitors of the binding of the labelled antimicrobials.

Figure 8:
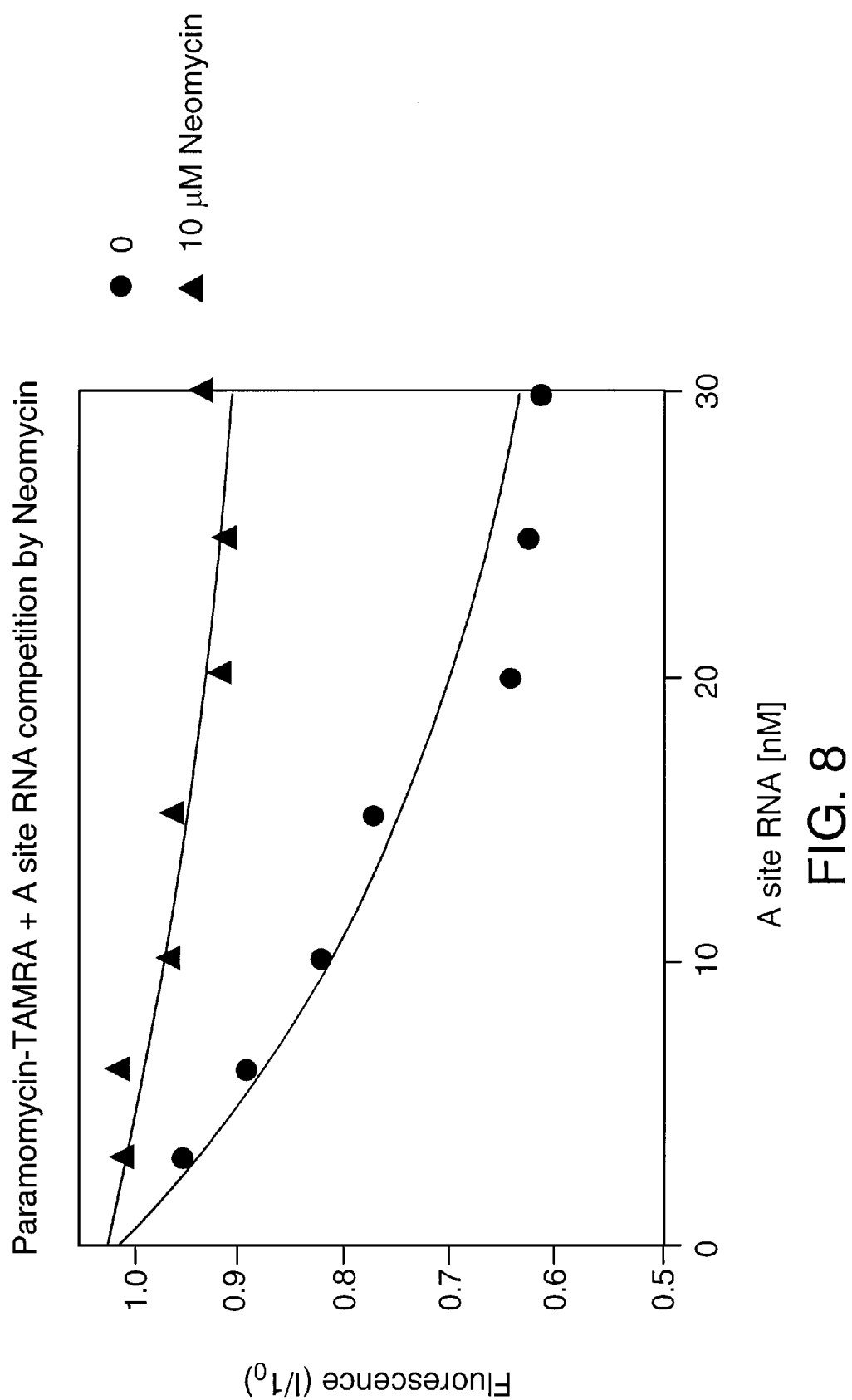
FIG. 8 shows the inhibition of binding of paramomycin-TAMRA to DABCYL-A site RNA by neomycin.

A control experiment of this type which demonstrates the use of unlabelled neomycin as a competitor is shown in FIG. 8. Binding of paramomycin-TAMRA to A site RNA was measured in a fluorescent plate reader. Measurements were made in a 96-well plate reader (Wallac victor) with a fixed wavelength of 544 nm and emission at 590 nm. $I_0$ was determined by an initial measurement of a 95 μL solution of 25 nM paramomycin-TAMRA in the presence of 50 mM Tris-HCl pH7.5, 80 mM KCl, 0.1% DMSO 0.00007% Triton X-100 and 0.5 ug/mL BSA presence of 10 μM Neomycin. I (the final measurement) was then measured following the addition of 5 μL of a 20×DABCYL-A site RNA stock solution (corresponding to the amounts shown in the figure). As shown in FIG. 8, a reduction in fluorescence in the presence of the neomycin competitor was observed compared to that of the control without neomycin, demonstrating the ability of the assay to detect binding of a competitor antibiotic to the target RNA.

Example 4

Inhibition of paramomycin-TAMRA to A site binding by 15 μM Paramomycin.

To further illustrate that the method of this invention can be applied to measure the competitive binding of test antimicrobials or compounds in assays involving an antimicrobial/target RNA pair, unlabelled paramomycin was used as a competitor in the paramomycin-TAMRA and DABCYL-A site RNA assay.

The results of testing unlabelled paramomycin as a competitive inhibitor of the binding of fluorescently-labelled paramomycin to fluorescently-labelled A site RNA is shown in FIG. 9. Binding of paramomycin-TAMRA to A site RNA was measured in a fluorescent plate reader. Measurements were made in a 96-well plate reader (Wallac victor) with a fixed wavelength of 544 nm and emission at 590 nm. $I_0$ was determined by an initial measurement of a 95 µL solution of 25 nM paramomycin-TAMRA in the presence of 50 mM Tris-HCl pH7.5, 80 mM KCl, 0.1% DMSO 0.00007% Triton X-100 and 0.5 ug/mL BSA presence of 15 µM Neomycin. I (the final measurement) was then measured following the addition of 5 µL of a 20×DABCYL-A site RNA stock solution (corresponding to the amounts shown in FIG. 9). Unlabelled paramomycin is a competitive inhibitor of the paramomycin-TAMRA and DABCYL-A site RNA FRET assay, as there was a reduction of quenching by FRET in the presence of unlabelled paramomycin (FIG. 9). The results of the assay are in agreement with those obtained using neomycin as the competitive antibiotic, further illustrating use of the invention to measure competitive binding assays involving an antimicrobial/target RNA pair and an antimicrobial (or other compound) to be tested.

Example 5

A model sequence for the L1 site (the E site), the site of action of the oxazolidinones.

Figures 11, 11A:
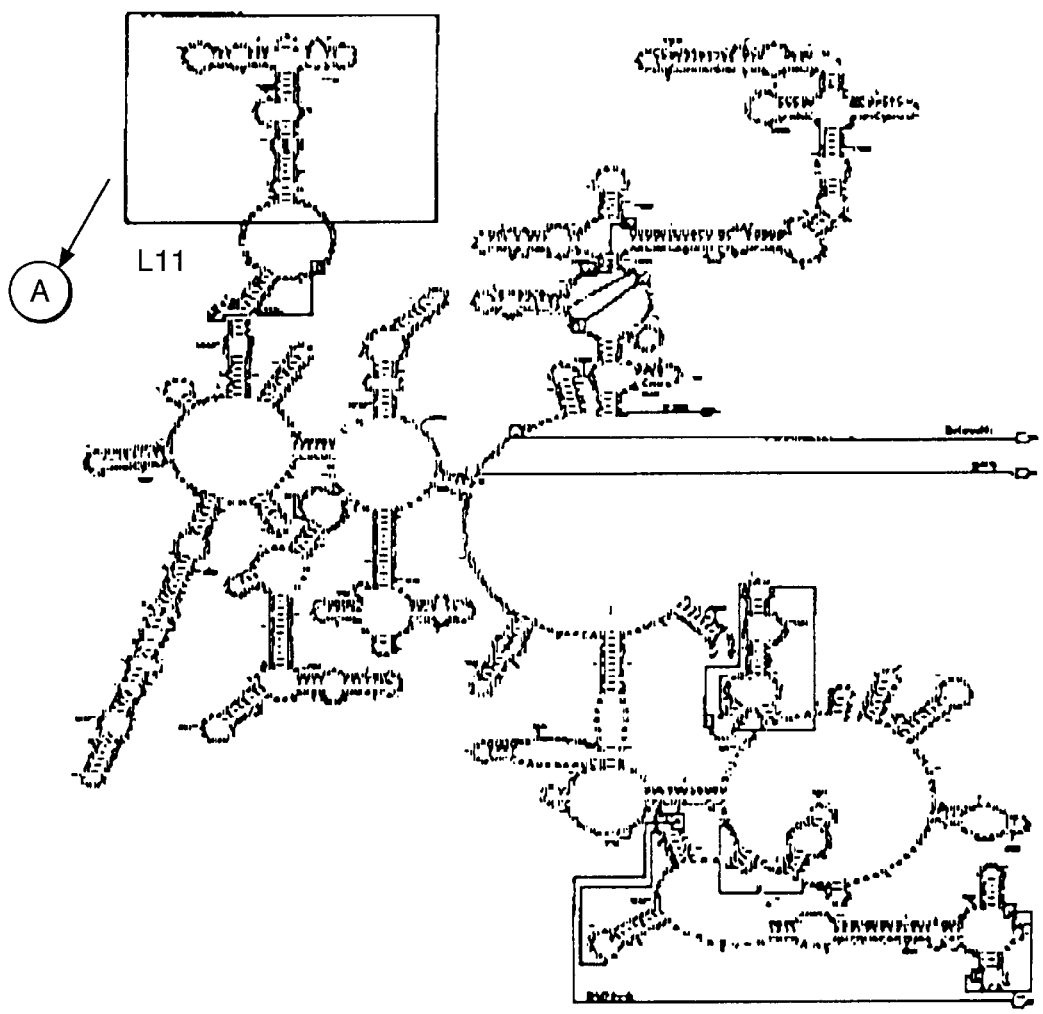
FIG. 11 shows the identification of a model sequence for the 23S rRNA GTPase center (SEQ ID NOs: 9 and 10), the site of action of the thiazole antibiotics.
Figure 11B:
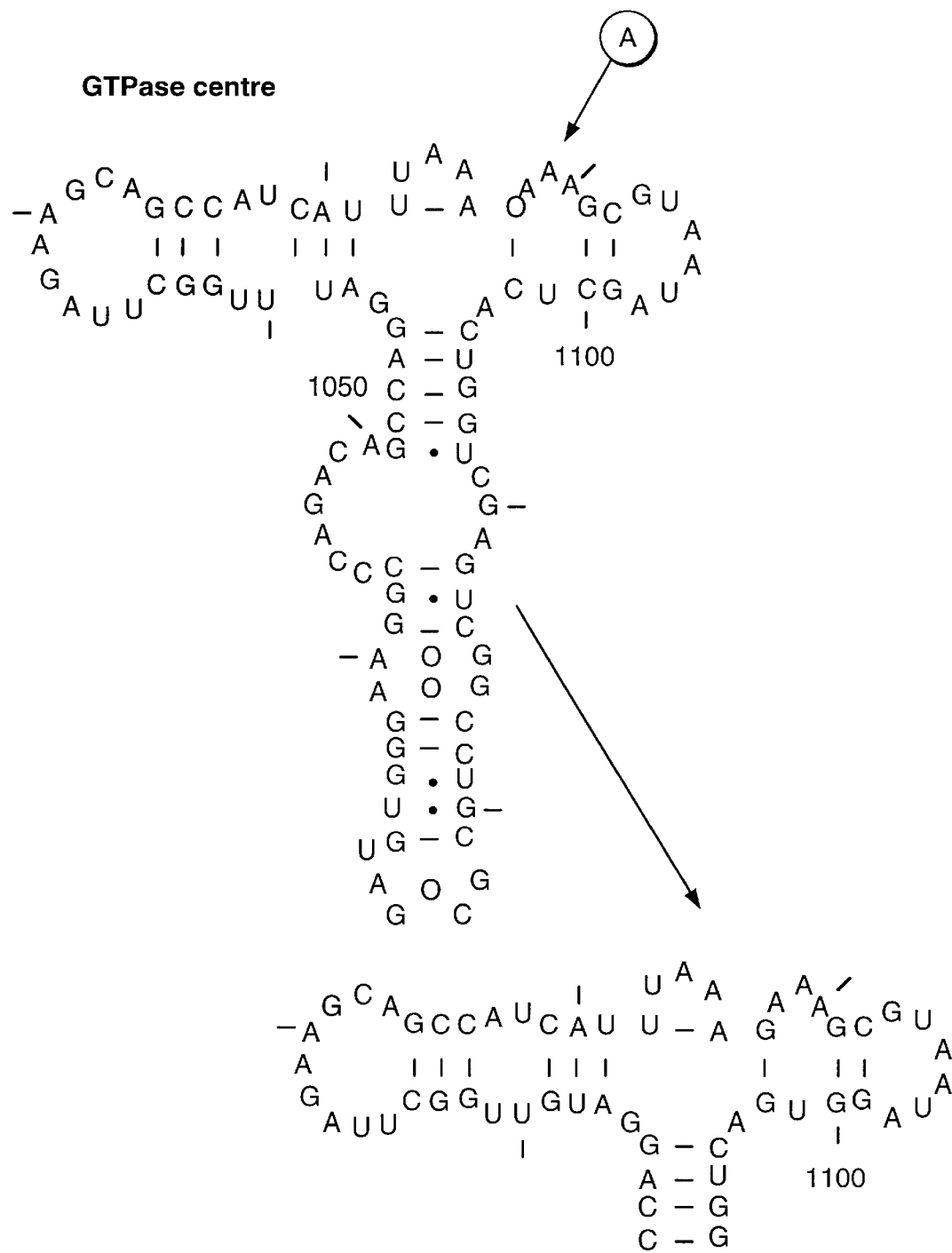

An antimicrobial-binding fragment (sub-region) of an antimicrobial-binding RNA useful according to the invention is identified from known antibiotic binding fragments available in the art. Such fragments serve as target RNAs. The complete 23S rRNA is bound in a variety of subregions by a number of antibiotics, including but not limited to those from the classes aminoglycoside, oxazolidinone, macrolide, tetracycline, and thiazole as illustrated in FIG. 2. The oxazolidinone antibiotics, as exemplified but not limited to those shown in FIG. 4, bind the 23S rRNA in the L1 or E site. The L1 or E site is highly conserved among bacteria, as exemplified by those sites shown for *Escherichia coli, Bacillus subtilis, Borrelia burgdorferi, Helicobacter pylon, Mycoplasma genitalium, Mycobacterium leprae* and *Haemophilus influenzae* in FIGS. 11 and 14. Identification of a candidate model target RNA for the L1 site is shown in FIG. 11 which shows reduction of 23S rRNA to generate small ribosomal subdomains that maintain the essential features of the RNA target (Gutell et al., 1993; Schnare et al., 1996). In this case the RNA target is characterized by intra helical hydrogen bonding and is likely to dictate that the RNA target be constructed from a relatively long oligoribonucleotide. The RNA folding may be further stabilized by the inclusion of the ribosomal protein L1. A model target RNA for the L1 site, which may be stabilized by the ribosomal protein L1, is useful according to the invention.

Example 6

A model sequence for the GTPase center (L11 binding site), the site of action of the thiazole antibiotics.

Figures 12, 12A:
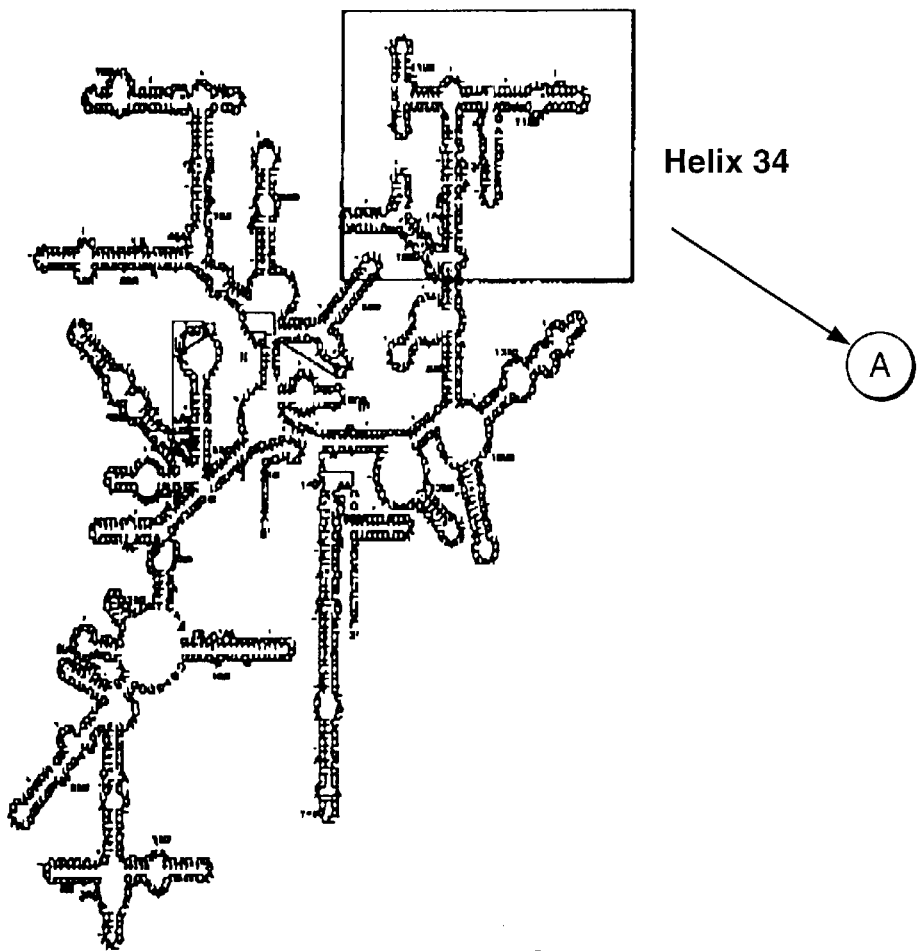
FIG. 12 shows the identification of a model sequence for the 16S rRNA spectinomycin binding site (SEQ ID NO: 11).
Figure 12B:
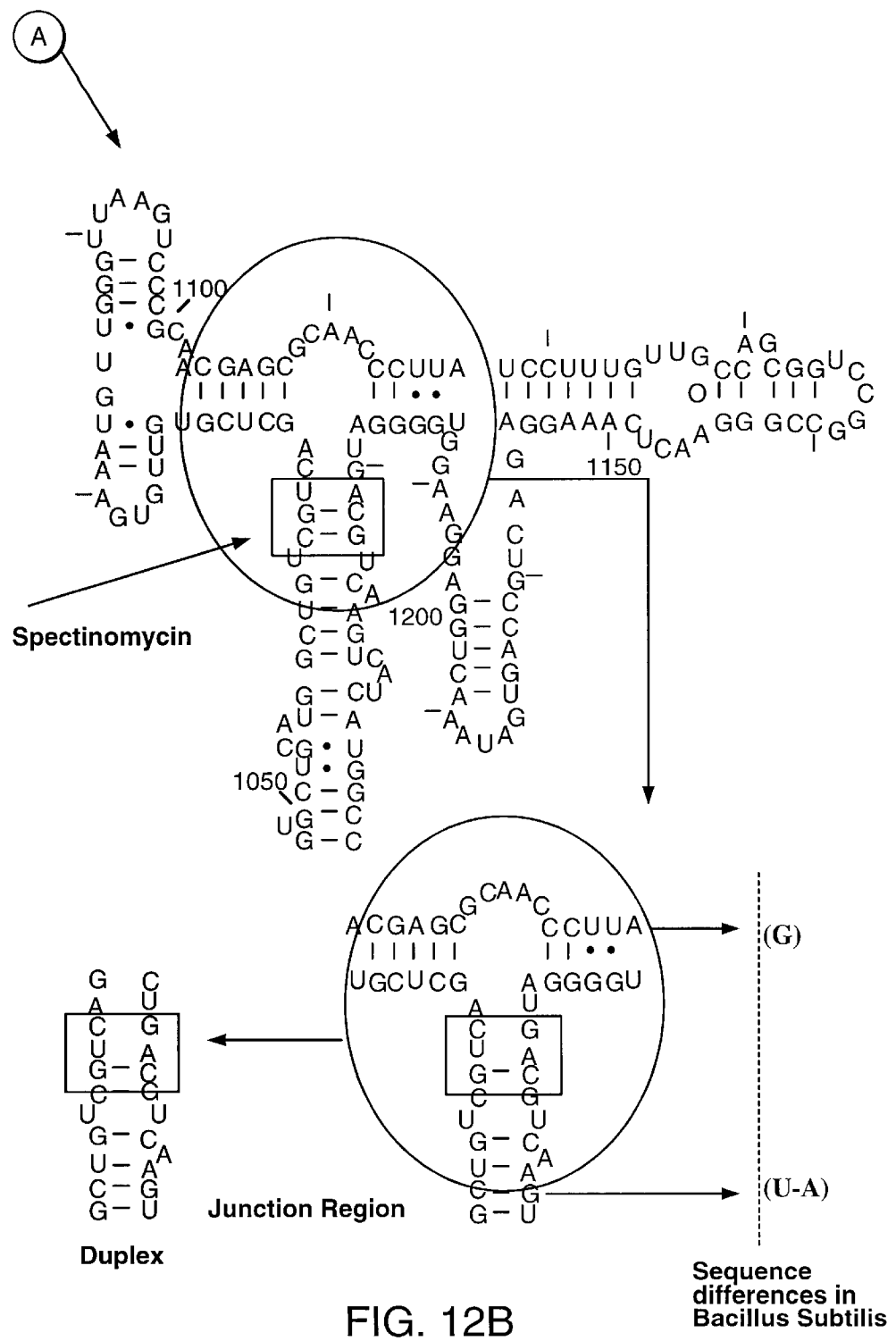

In addition to the L1 site, the 23S rRNA is bound by antibiotics in other subregions, including its GTPase center (L11 binding site), as shown in FIG. 2. The GTPase center contains the binding site for the antibiotic thiostrepton. The GTPase center is highly conserved among bacteria, as demonstrated in FIGS. 12 and 15 for *Escherichia coli, Bacillus subtilis, Borrelia burgdorferi, Helicobacter pylori, Mycoplasma genitalium, Mycobacterium leprae* and *Haemophilus influenzae*. Identification of a target RNA for the thiostrepton binding site is shown in FIG. 12, which shows reduction of 23S rRNA to generate small ribosomal subdomains that maintain the essential features of the RNA target (Gutell et al., 1993; Schnare et al., 1996). In this instance, the RNA target comprises a number of structural motifs, including two hairpin loops, a helical junction and a number of potentially unpaired bases. This potential complexity necessitates that the RNA target be constructed from a relatively long oligoribonucleotide. The L11 target RNA is useful according to the invention and may be further stabilized by the inclusion of the ribosomal protein L 11.

Example 7

A model sequence 16S rRNA site at which spectinomycin binds.

Figures 16, 16A:
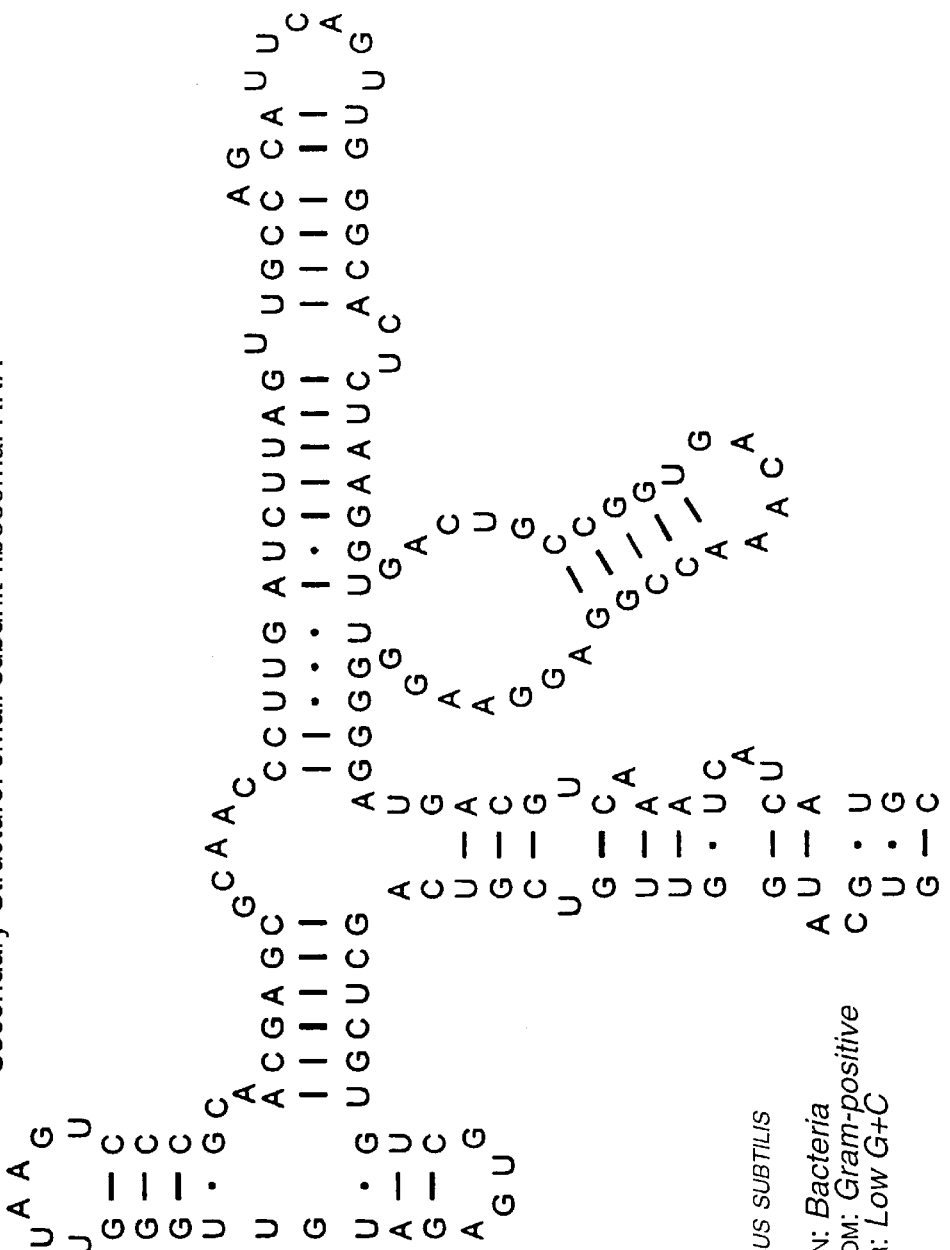
FIG. 16. Representative 16S rRNA sequences for helix 34, the S5 protein binding site at which spectinomycin binds. The diverse organisms *Bacillus subtilis* (SEQ ID NO: 31), *Borrelia burgdorferi* (SEQ ID NO: 32), *Campylobacter sputorum* (SEQ ID NO: 33), *Mycoplasma hyopneumoniae* (SEQ ID NO: 34), *Clostridium innocuum* (SEQ ID NO: 35), *Haemophilus influenzae* (SEQ ID NO: 36 ) and *Mycoplasma genitalium* (SEQ ID NO: 37) are shown.
Figure 16B:
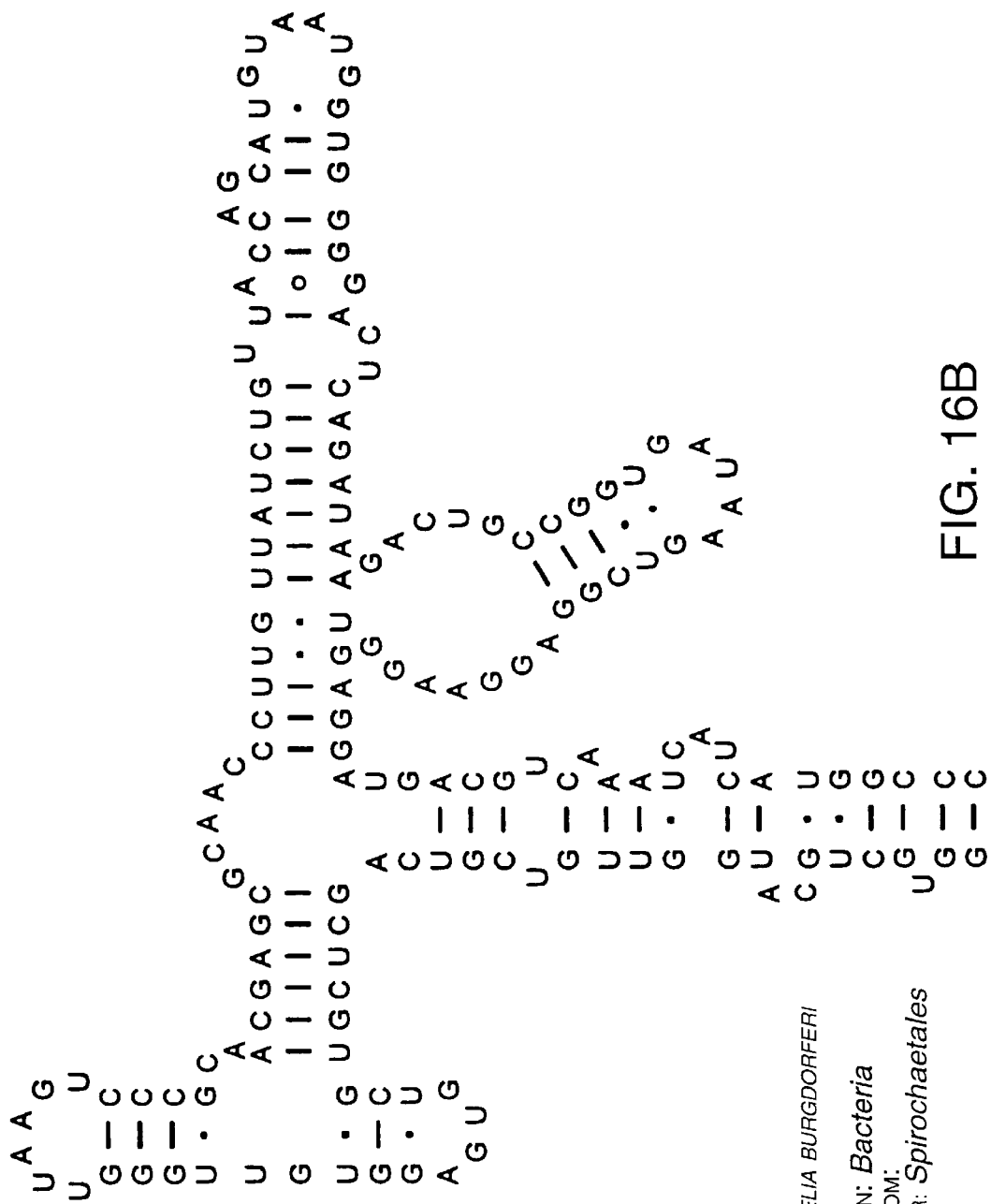
Figure 16C:
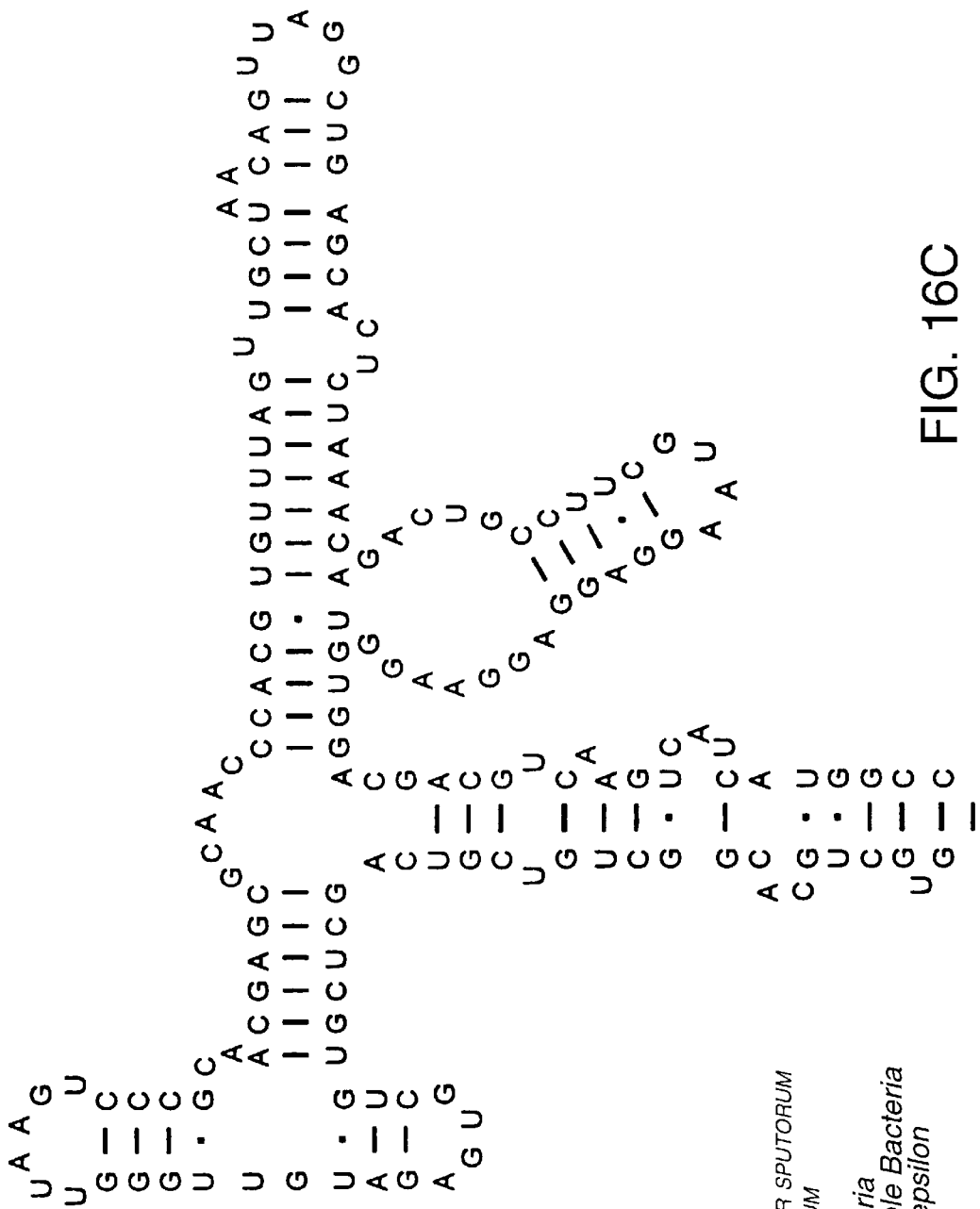
Figure 16D:
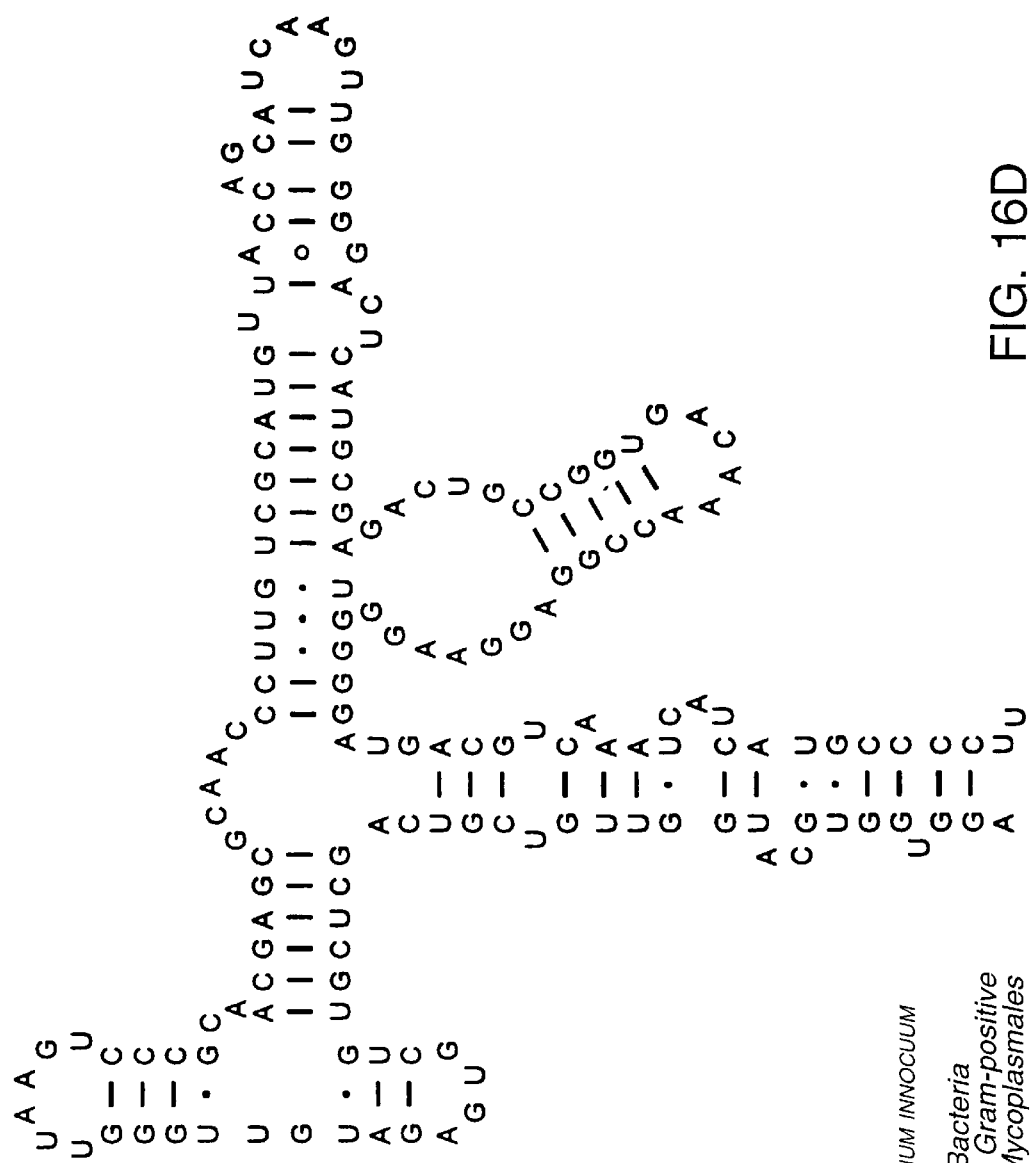
Figure 16E:
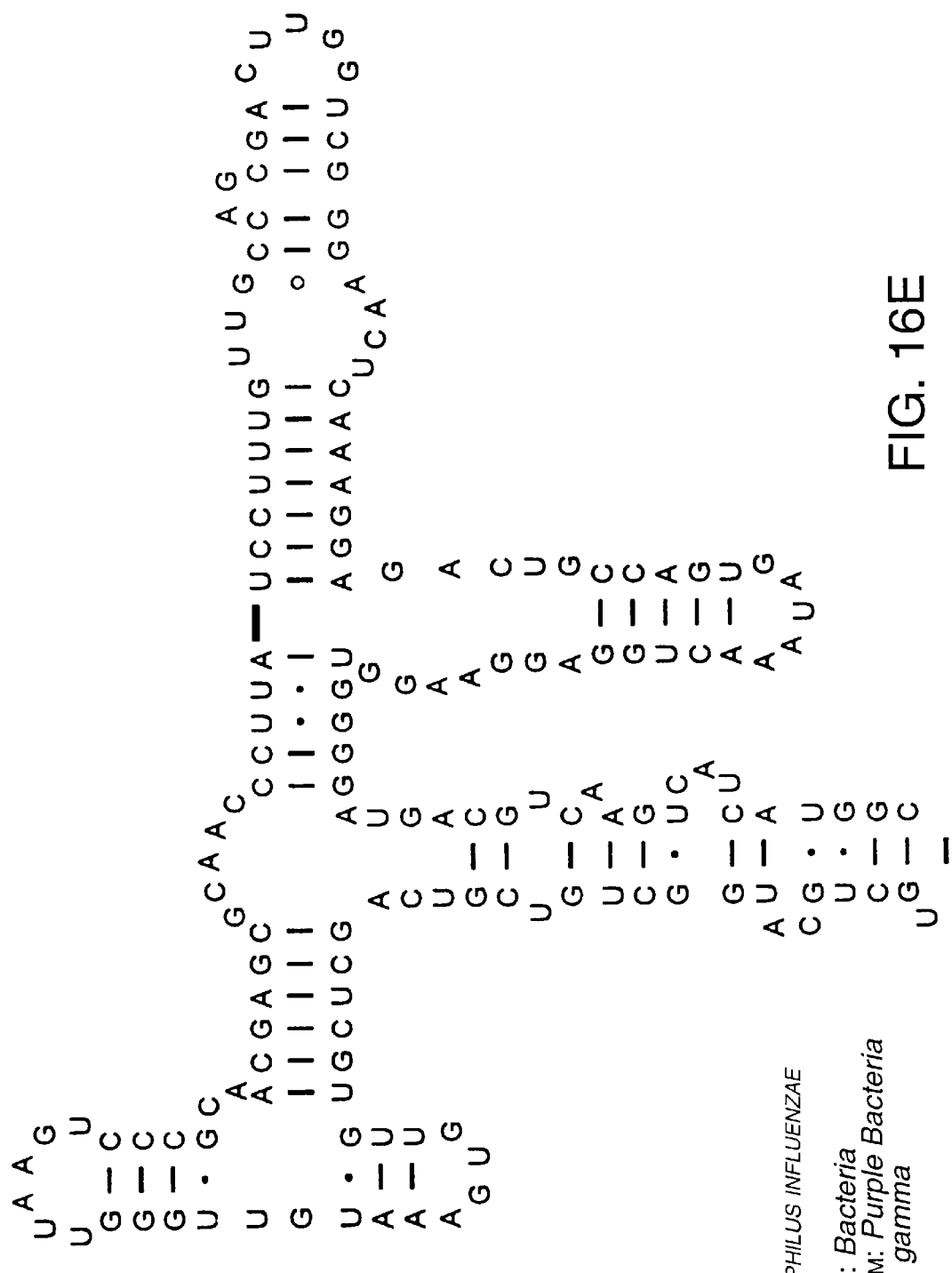
Figure 16F:
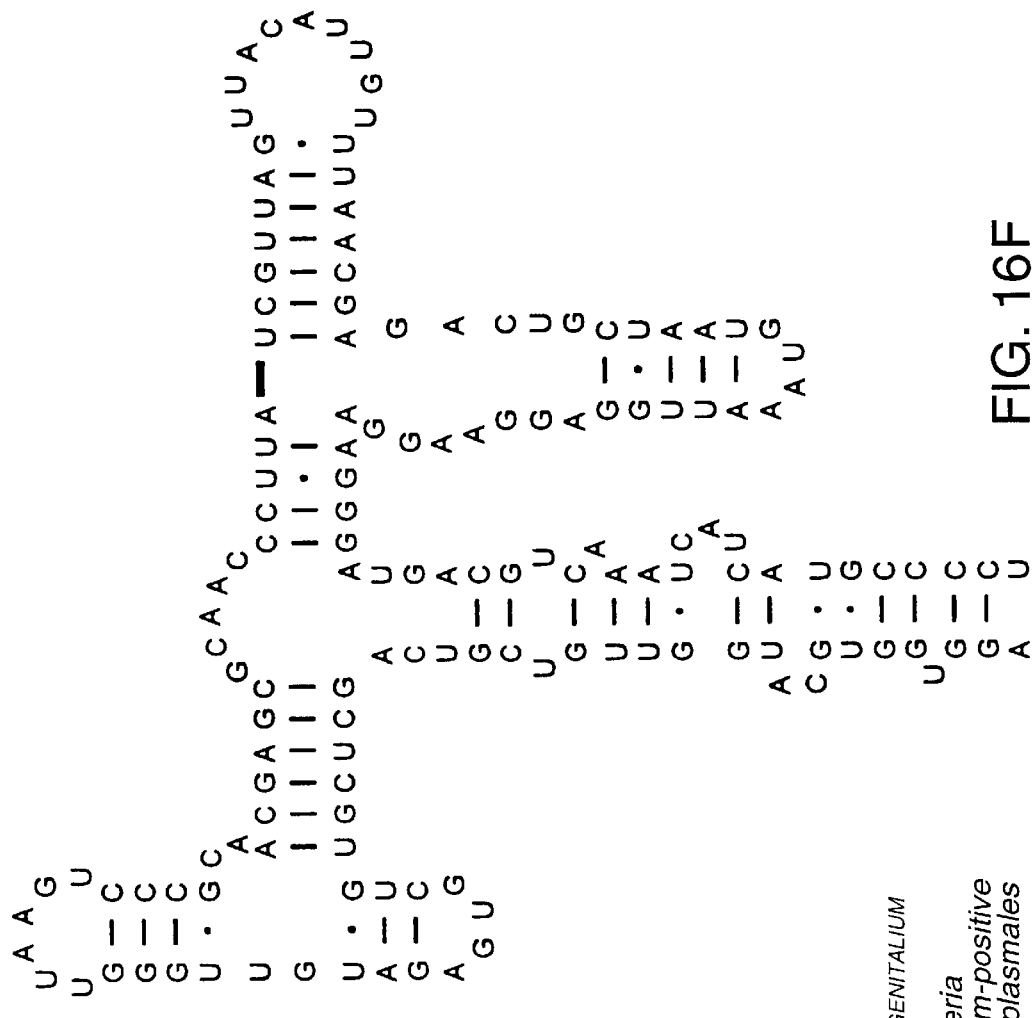
Figure 16G:
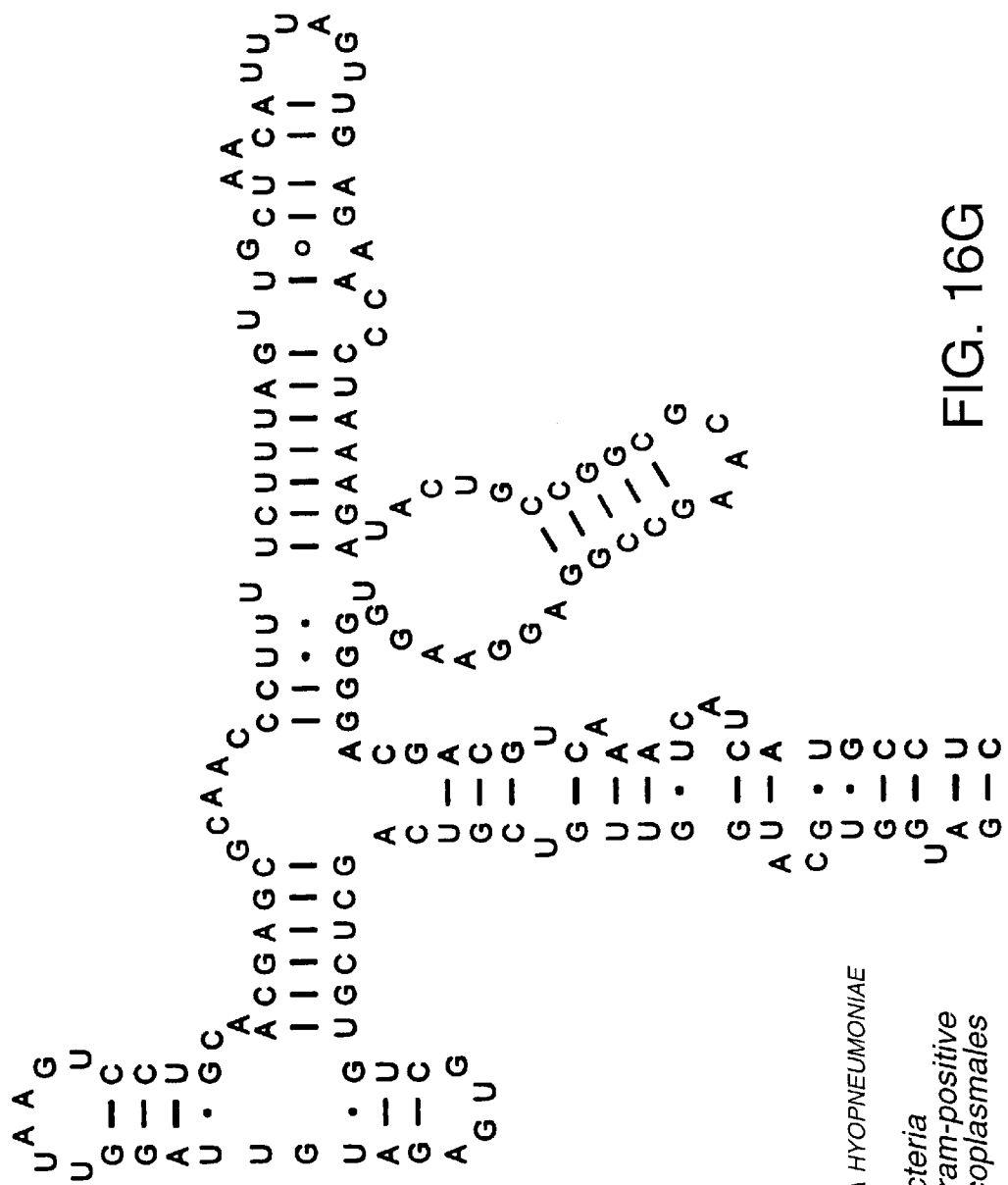

As illustrated in FIG. 1, a number of antibiotics bind the 16S rRNA in a variety of subregions. The antibiotic spectinomycin binds the subregion of 16S rRNA depicted in FIG. 12, which is known as helix 34 and the S5 protein binding site. The high conservation of this site among bacteria is shown in FIGS. 12 and 16, which depict the spectinomycin binding site for diverse organisms *Escherichia coli, Bacillus subtilis, Borrelia burgdorferi, Campylobacter sputorum, Mycoplasma hyopneumoniae, Clostridium innocuum, Haemophilus influenzae* and *Mycoplasma genitalium*. A model sequence for the spectinomycin binding site can be identified by reduction of the 16S rRNA to generate small ribosomal domains that maintain the essential features of the RNA target (Gutell et al., 1993; Schnare et al., 1996) (FIG. 12). In this case the RNA target comprises a short double stranded RNA sequence next to a complex 3 helical junction. The RNA target may be constructed from a relatively long oligoribonucleotide in which the arms of the helical junction are shortened and linked by loops. The target may be further reduced such that it consists of the double helical region alone. In FIG. 12, an *Escherichia coli* target RNA sequence is shown and the mutational differences for the gram-positive bacteria *Bacillus subtilis* target RNA sequence are shown in brackets. These model RNAs for the spectinomycin binding site are useful according to the invention.

TABLE 1

The following molecules are antimicrobials that contain amine groups that are appropriate for the introduction of fluorescent dyes. They are examples and are not a limiting set.

| Class | Antibiotic | Target | rRNA | Nucleotides(s) | Reference |
|---|---|---|---|---|---|
| Aminoglycoside | Amikacin | A site | 16S | 1408 | Prammananan et al., 1998, J. Infect. Dis. 177:1573 |
| Aminoglycoside | Apramycin | A site | 16S | 1408 1419 1494 | Woodcock et al., 1991, EMBO J. 10:3099 |

TABLE 1-continued

The following molecules are antimicrobials that contain amine groups that are appropriate for the introduction of fluorescent dyes. They are examples and are not a limiting set.

| Class | Antibiotic | Target | rRNA | Nucleotides(s) | Reference |
|---|---|---|---|---|---|
| Aminoglycoside | Bekanamycin | A site | 16S | | Hamasaki et al., 1998, Biochemistry 37:656 |
| Aminoglycoside | Gentamicin | A site (L6) | 16S | 1408 1419 1494 | Yoshizawa et al., 1998, EMBO J. 17:6437 |
| Aminoglycoside | Hygromycin B | A site | 16S | 1491 1495 | Moazed and Noller, 1987, Nature 327:389 |
| Aminoglycoside | Kanamycin | A site | 16S | 1408 1419 1494 | Beauclerk and Cundliffe, 1987, J. Mol. Biol. 193:661 |
| Aminoglycoside | Kasugamycin | P site | 16S | 794 926 | Woodcock et al., 1991, EMBO J. 10:3099 |
| Aminoglycoside | Neamin | A site | 16S | 1408 1419 1494 | Woodcock et al., 1991, EMBO J. 10:3099 |
| Aminoglycoside | Neomycin | A site | 16S | 1408 1419 1494 | Recht et al., 1999, J. Mol. Biol. 286:33 |
| Aminoglycoside | Paromomycin | A site | 16S | 1408 1419 1491 1494 | Fourmy et al., 1998, J. Mol. Biol. 277:333 |
| Aminoglycoside | Sisomycin | | | | Kojic et al., 1992, J. Bacteriol. 174:7868 |
| Aminoglycoside | Spectinomycin | S5 binding site | 16S | 1063–1065 1191–1193 | Moazed and Noller, 1987, Nature 327:389 |
| Aminoglycoside | Tobramycin | A site | 16S | 1408 | Prammananan et al., 1998, J. Infect. Dis. 177:1573 |
| Cyclic Peptide | Viomycin | | 23S | 913 914 | Moazed and Noller, 1987, Biochimie 69:879 |

TABLE 2

The following molecules are antimicrobials that contain ketone groups that are appropriate for the introduction of fluorescent dyes. They are examples and are not a limiting set.

| Class | Antibiotic | Target | rRNA | Nucleotides(s) | Reference |
|---|---|---|---|---|---|
| Macrolide | Spiramycin | peptide transferase | 23S | 2611 | Gauthier et al., 1988, Mol. Gen. Genet. 214:192 |
| Macrolide (14) | Erythromycin | peptidyl transferase | 23S | 2057 2058 2059 2447 2505 2611 | Douthwaite and Aagaard, 1993, J. Mol. Biol. 232:725 |
| Macrolide (16) | Tylosin | peptidyl transferase | 23S | | Rodriguez-Fonseca et al., 1995, J. Mol. Biol. 247:224 |
| Tetracycline | Chlortetracycline | A (P) site | 16S (23S) | | Mikulik et al., 1983, FEBS Lett. 152:125; Oehler et al., 1997, Nucleic Acids Res. 25:1219 |

TABLE 3

The following molecules are antimicrobials that contain aldehyde groups that are appropriate for the introduction of fluorescent dyes. They are examples and are not a limiting set.

| Class | Antibiotic | Target | rRNA | Nucleotides(s) | Reference |
|---|---|---|---|---|---|
| Oxazolidinone | DuPont 721 | E site, L1 binding site | 23S (16S) | 2113 2114 2118 2119 2153 (864) | Matassova et al., 1999, RNA 5:939 |
| Aminoglycoside | Streptomycin | A site, 915 region, S12, S5?, L11? | 16S | 523 911–915 | Woodcock et al., 1991, EMBO J. 10:3099: Spickler et al., 1997, J. Mol. Biol. 273:586 |

TABLE 4

The following molecules are antimicrobials that contain dehydrobutyrene and dehydroalanine groups that are appropriate for the introduction of fluorescent dyes. They are examples and are not a limiting set.

| Class | Antibiotic | Target | rRNA | Nucleotides(s) | Reference |
|---|---|---|---|---|---|
| Thiazole | Nosiheptide | GTPase associated centre | 23S | 1067 | Cundliffe and Thompson, 1981, J. Gen. Microbiol. 126:185 |
| Thiazole | Thiostrepton | GTPase associated centre | 23S | 1067 1095 | Egebjerg et al., 1989, EMBO J., 8:607 |

TABLE 5

Typical values of $R_o$

| Donor | Acceptor | Ro (Å)* |
|---|---|---|
| Fluorescein | Tetramethylrhodamine | 55 |
| IAEDANS | Fluorescein | 46 |
| EDANS | DABCYL | 33 |
| Fluorescein | Fluorescein | 44 |
| BODIPY FL | BODIPY FL | 57 |

*$R_o$ is the distance at which 50% of excited donors are deactivated by FRET. Data from Haugland, RP. 1996. Handbook of Fluorescent Probes and Research Chemicals, 6th edition. Molecular Probes, Inc. Eugene OR, USA.

TABLE 6

FRET-pairs suitable for use in the method of this invention.

| Donor | Acceptor |
|---|---|
| (a) Fluorescent donors | |
| Fluorescein | Tetramethyl rhodamine |
| Fluorescein | Cy-3 |
| EDANS | DABCYL |
| Dansyl | Fluorescein |
| Cy3 | Cy-5 |
| Tryptophan | AEDANS |
| Fluorescein | Tetramethyl rhodamine |
| Tetramethyl rhodamine | DABCYL |
| Fluorescein | DABCYL |
| DABCYL | Cy-3 |
| Fluorescein | Hexachlorofluorescein |
| Tetrachlorofluorescein | Cy-5 |
| (b) Luminescent donors | |
| Europium | Cy-5 |
| Terbium | Tetramethyl rhodamine |
| Terbium | Cy-3 |

TABLE 7

Antitumor antimicrobials acting on tRNA

| Antibiotic | Target | Reference |
|---|---|---|
| Enediynes | tRNA$^{Phe}$ | Sugiura et al., 1997, Bioorg. Med. Chem. 5:1229 |
| Colicin E5 (Nuclease) | tRNA(Tyr, His, Asn, Asp), anticodon loop | Ogawa et al., 1999, Science 283:2097 |

TABLE 8

Additional classes of antimicrobials.

| Class | Antibiotic | Target | rRNA | Nucleotides(s) | Reference |
|---|---|---|---|---|---|
| Alkaloid | Narciclasine | peptidyl transferase | 23S | ? | Rodriguez-Fonseca et al., 1995, J. Mol. Biol. 247:224 |
| Alkaloid | Emetine | yeast S14 binding site? | 16S | ? | Fewell and Woolford, 1999, Mol. Cell. Biol. 19:826 |
| N-glycosidase | Ricin | elongation factor binding site | 23S | 2660 | Endo and Tsurugi, 1988 J. Biol. Chem. 263:8735 |
| Nuclease | Colicin E3 | A site | 16S | 1493 1494 | Bowman et al., 1971, Nature New Biol. 234:133 |
| Nuclease | alpha-Sarcin | elongation factor binding site | 23S | 2660/2661 | Moazed et al., 1988, Nature 334:362 |
| Nucleoside derivative | Puromycin | A site (50S) | 23S | 2502 2504 | Jaynes EN et al., Biochemistry 1978 Feb 21; 17(4):561–9 |
| Nucleoside derivative | Sparsomycin | peptidyl transferase | 23S | 2602, 2603 | Lazaro E, et al., J Mol Biol 1996 Aug 16; 261(2):231–8 |
| Pyrrolidine derivative | Anisomycin | peptidyl transferase | 23S | 2447 2452 2453 | Rodriguez-Fonseca et al., 1995, J. Mol. Biol. 247:224 |

TABLE 8-continued

Additional classes of antimicrobials.

| Class | Antibiotic | Target | rRNA | Nucleotides(s) | Reference |
| --- | --- | --- | --- | --- | --- |
| Sesquiterpene | Fusarenon X | peptidyl transferase | 23S | | Jimenez and Vazquez Eur J Biochem 1975 Jun; 54(2):483–92 |
| Sesquiterpene | T2 toxin | peptidyl transferase | 23S | 2394 | Rodriguez-Fonseca et al., 1995, J. Mol. Biol. 247:224 |
| Streptogramin A (MLS group) | Virginiamycin M1 | peptidyl transferase | 23S | 2059 2394 2503 | Porse and Garrett J Mol Biol 1999 Feb 19; 286(2):375–87 |
| Streptogramin B (MLS group) | Vemamycin B | peptidyl transferase | 23S | 752 2062 2505 | Moazed and Noller 1987 Biochimie Aug; 69(8):879–84 |

References

The patent and scientific literature referred to herein establishes the knowledge that is available to those with skill in the art. The contents of all references mentioned herein are incorporated by reference in their entirety.

Aboul-ela, F., Karn, J. & Varani, G. (1995). The structure of the human immunodeficiency virus type 1 TAR RNA reveals principles of RNA recognition by Tat protein. J. Mol. Biol., 253, 313–332.

Agrawal, S., Goodchild, J., Civiera, M. P., Thornton, A. H., Sarin, P. S. & Zamecnik, P. C. (1988). Oligodeoxynucleoside phosphoramidates and phosphorothioates as inhibitors of human immunodeficiency virus. Proc. Natl. Acad. Sci. USA, 85, 7079–7083.

Beauclerk, A. A. and Cundliffe, E. (1987) Sites of action of two ribosomal RNA methylases responsible for resistance to aminoglycosides. J. Mol. Biol., 193, 661–671.

Bowman, C. M., Sidikaro, J., Nomura, M. (1971) Specific inactivation of ribosomes by colicin E3 in vitro and mechanism of immunity in colicinogenic cells. Nature New Biol., 234, 133–137.

Brodsky, A. S. & Williamson, J. R. (1997). Solution structure of the HIV-2 TAR-argininamide complex. J. Mol. Biol., 267, 624–639.

Cai, Z., Gorin, A., Frederick, R., Ye, X., Hu, W., Majumdar, A., Kettani, A. & Patel, D. J. (1998). Solution structure of P22 transcriptional antitermination N peptide-box B RNA complex. Nature Struct. Biol., 5, 203–212.

Connolly, B. A. & Newman, P. C. (1989). Synthesis and properties of oligonucleotides containing 4-thiothymidine, 5-methyl-2-pyrimidinone-1-beta-D(2'-deoxyriboside) and 2-thiothymidine. Nucl. Acids Res., 17, 4957–4974.

Cundliffe, E. and Thompson, J. (1981) The mode of action of nosiheptide (multhiomycin) and the mechanism of resistance in the producing organism. J Gen Microbiol, 126, 185–192.

De Guzman, R. N., Wu, Z. R., Stalling, C. C., Pappalardo, L., Borer, P. N. & Summers, M. F. (1998). Structure of the HIV-1 nucleocapsid protein bound to the SL3-RNA recognition element. Science, 279, 384–388.

Douthwaite, S. and Aagaard, C. (1993) Erythromycin binding is reduced in ribosomes with conformational alterations in the 23 S rRNA peptidyl transferase loop. J. Mol. Biol., 232, 725–731.

Egebjerg, J. Douthwaite, S., Garrett, R. A. (1989) Antibiotic interactions at the GTPase-associated centre within *Escherichia coli* 23S rRNA. EMBO J., 8, 607–611.

Endo, Y., Tsurugi, K. (1988) The RNA N-glycosidase activity of ricin A-chain. The characteristics of the enzymatic activity of ricin A-chain with ribosomes and with rRNA. J. Biol. Chem. 263, 8735–8739.

Fewell, S. W., Woolford, J. L. Jr. (1999) Ribosomal protein S14 of Saccharomyces cerevisiae regulates its expression by binding to RPS14B pre-mRNA and to 18S rRNA. Mol. Cell. Biol., 19, 826–834.

Fourmy, D., Recht, M. I. and Puglisi, J. D. (1998) Binding of neomycin-class aminoglycoside antibiotics to the A-site of 16 S rRNA. J. Mol. Biol., 277, 347–362.

Fourmy, D., Yoshizawa, S. and Puglisi, J. D. (1998) Paromomycin binding induces a local conformational change in the A-site of 16 S rRNA. J. Mol. Biol., 277, 333–345.

Gait, M. J., Earnshaw, D. J., Farrow, M. A., Fogg, J. H., Grenfell, R. L., Naryshkin, N. A. & Smith, T. V. (1998). Applications of chemically synthesised RNA. In RNA-Protein Interactions: A Practical Approach, ed. C. Smith, pp 1–36. Oxford: Oxford University Press.

Gait, M. J., Jones, A. S. & Walker, R. T. (1974). Synthetic-analogues of polynucleotides XII. Synthesis of thymidine derivatives containing an oxyacetamido-or an oxyformamido-linkage instead of a phosphodiester group. J. Chem. Soc. Perkin I, 14, 1684–1686.

Gauthier, A., Turmel, M., Lemieux, C. (1988) Mapping of chloroplast mutations conferring resistance to antibiotics in Chlamydomonas: evidence for a novel site of streptomycin resistance in the small subunit rRNA. Mol. Gen. Genet., 214, 192–197.

Grasby, J. A., Butler, P. J. G. & Gait, M. J. (1993). The synthesis of oligoribonucleotides containing O6-methylguanosine: the role of conserved guanosine residues in hammerhead ribozyme cleavage. Nucl. Acids Res., 21, 4444–4450.

Gutell, R. R., Gray, M. W. and Schnare, M. N. (1993) A compilation of large subunit (23S and 23S-like) ribosomal RNA structures: 1993. Nucleic Acids Res, 21, 3055–3074.

Hamasaki, K., Killian, J., Cho, J. and Rando, R. R. (1998) Minimal RNA constructs that specifically bind aminoglycoside antibiotics with high affinities. Biochemistry, 37, 656–663.

Hélene, C., Montenay-Garestier, T., Saison, T., Takasugi, M., Toulmé, J. J., Asseline, U., Lancelot, G., Maurizot, J. C., Toulmé, F. & Thuong, N. T. (1985). Oligodeoxynucleotides covalently linked to intercalating agents: a new class of gene regulatory substances. Biochimie, 67, 777–783.

Heyduk, E. & Heyduk, T. (1997). Thiol-reactive, luminescent europium chelates: luminescence probes for resonance energy transfer distance measurements in biomolecules. Anal. Biochem., 248, 216–227.

Iwai, S., Pritchard, C., Mann, D. A., Karn, J. & Gait, M. J. (1992). Recognition of the high affinity binding site in Rev-response element RNA by the human immunodeficiency virus type-1 Rev protein. Nucl. Acids Res., 20, 6465–6472.

Jaynes EN Jr, Grant PG, Giangrande G, Wieder R, Cooperman BS (1978) Photoinduced affinity labeling of the *Escherichia coli* ribosome puromycin site. Biochem. 17:561–9.

Jimenez A, Vazquez D (1975) Quantitative binding of antibiotics to ribosomes from a yeast mutant altered on the peptidyl-transferase center. Eur. J. Biochem. 54(2):483–92.

Karn, J., Gait, M. J., Churcher, M. J., Mann, D. A., Mikaélian, I. & Pritchard, C. (1995). Control of human immunodeficiency virus gene expression by the RNA-binding proteins Tat and Rev. In RNA-protein Interactions, ed. K. Nagai and I.

Mattaj, pp 192–220. Oxford: Oxford University Press.

Kojic, M., Topisirovic, L. and Vasiljevic, B. (1992) Cloning and characterization of an aminoglycoside resistance determinant from Micromonospora zionensis. J. Bacteriol. 174, 7868–7872.

Lamm, G. M., Blencowe, B. J., Sproat, B. S., Iribarren, A. M., Ryder, U. & Lamond, A. I. (1991). Antisense probes containing 2-aminoadenosine allow efficient depletion of U5 snRNP from HeLa splicing extracts. Nucl. Acids Res., 19, 3193–3198.

Lazaro E, Rodriguez-Fonseca C, Porse B, Urena D, Garrett RA, Ballesta JP (1996) A sparsomycin-resistant mutant of Halobacterium salinarium lacks a modification at nucleotide U2603 in the peptidyl transferase centre of 23 S rRNA. J. Mol. Biol. 261, 231–8.

Lee, B. L., Murakami, A., Blake, K. R., Lin, S. B. & Miller, P. S. (1988). Interaction of psoralen-derivatized oligodeoxyribonucleoside methylphosphonates with single-stranded DNA. Biochemistry, 27, 3197–3203.

Mag, M. & Engels, J. W. (1988) Synthesis and structure assignments of amide protected nucleosides and their use as phosphoramidites in deoxyoligonucleotide synthesis. Nucl. Acids Res., 16, 3525–3543.

Mann, D. A., Mikaélian, I., Zemmel, R. W., Green, S. M., Lowe, A. D., Kimura, T., Singh, M., Butler, P. J. G., Gait, M. J. & Karn, J. (1994). A molecular rheostat: Co-operative Rev binding to Stem I of the Rev-response element modulates human immunodeficiency virus type-1 late gene expression. J. Mol. Biol., 241, 193–207.

Matassova, N. B., Rodnina, M. V., Endermann, R., Kroll, H. P., Pleiss, U., Wild, H. and Wintermeyer, W. (1999) Ribosomal RNA is the target for oxazolidinones, a novel class of translational inhibitors. RNA, 5, 939–946.

Metzger, A. U., Bayer, P., Willbold, D., Hoffmann, S., Frank, R. W., Goody, R. S. & Rösch, P. (1997) The interaction of HIV-1 Tat (32–72) with its target RNA: a fluorescence and nuclear magnetic resonance study. Biochem. Biophys. Res. Comm., 241, 31–36.

Mikulik, K., Jiranova, A., Janda, I. and Weiser, J. (1983) Susceptibility of ribosomes of the tetracycline-producing strain of Streptomyces aureofaciens to tetracyclines. FEBS Lett., 152, 125–130.

Miller, P. S., Chandrasegaran, S., Dow, D. L., Pulford, S. M. & Kim, L. S. (1982) Synthesis and template properties of an ethyl phosphotriester modified decadeoxyribonucleotide. Biochem., 21, 5468–5474.

Miller, P. S., Dreon, N., Pulford, S. M. & McParland, K. B. (1980) Oligothymidylate analogues having stereoregular, alternating methylphosphonate/phosphodiester backbones. Synthesis and physical studies. J. Biol. Chem., 255, 9569–9665.

Moazed, D., Noller, H. F. (1987) Chloramphenicol, erythromycin, carbomycin and vernamycin B protect overlapping sites in the peptidyl transferase region of 23S ribosomal RNA. Biochirnie, 69, 879–884.

Moazed, D., Noller, H. F. (1987) Interaction of antibiotics with functional sites in 16S ribosomal RNA. Nature, 327, 389–394.

Moazed D, Noller HF (1987) Chloramphenicol, erythromycin, carbomycin and vernamycin B protect overlapping sites in the peptidyl transferase region of 23S ribosomal RNA. Biochimie 69(8):879–84.

Moazed, D., Robertson, J. M., Noller, H. F. (1988) Interaction of elongation factors EF-G and EF-Tu with a conserved loop in 23S RNA. Nature 334, 362–364.

Oehler R, Polacek N, Steiner G, Barta A (1997) Interaction of tetracycline with RNA: photoincorporation into ribosomal RNA of *Escherichia coli*. Nucl. Acids Res., 25, 1219–1224.

Ogawa, T., Tomita, K., Ueda, T., Watanabe, K., Uozumi, T., Masaki, H. (1999) A cytotoxic ribonuclease targeting specific transfer RNA anticodons. Science 283, 2097–2100.

Perrouault, L., Asseline, U., Rivalle, C., Thuong, N. T., Bisagni, E., Giovannangeli, C., Le Doan, T. & Hélene, C. (1990). Sequence-specific artificial photo-induced endonucleases based on triple helix-forming oligonucleotides. Nature, 344, 358–360.

Piccirilli, J. A., Krauch, T., Moroney, S. E. & Benner, S. A. (1990). Enzymatic incorporation of a new base pair into DNA and RNA extends the genetic alphabet. Nature, 343, 33–37.

Porse BT, Garrett RA (1999) Sites of interaction of streptogramin A and B antibiotics in the peptidyl transferase loop of 23 S rRNA and the synergism of their inhibitory mechanisms. J. Mol. Biol. 286(2):375–87.

Prammananan, T., Sander, P., Brown, B. A., Frischkorn, K., Onyi, G. O., Zhang, Y., Bottger, E. C., Wallace, R. J. Jr. (1998). A single 16S ribosomal RNA substitution is responsible for resistance to amikacin and other 2-deoxystreptamine aminoglycosides in Mycobacterium abscessus and Mycobacterium chelonae. J. Infect. Dis., 177, 1573–1581.

Puglisi, J. D., Tan, R., Calnan, B. J., Frankel, A. D. & Williamson, J. R. (1992). Conformation of the TAR RNA-arginine complex by NMR spectroscopy. Science, 257, 76–80.

Purohit, P. & Stern, S. (1994) Interactions of a small RNA with antibiotic and RNA ligands of the 30S subunit. Nature, 370, 659–662.

Recht, M. I., Douthwaite, S., Dahlquist, K. D. and Puglisi, J. D. (1999) Effect of mutations in the A site of 16 S rRNA on aminoglycoside antibiotic-ribosome interaction. J. Mol. Biol., 286, 33–43.

Rodriguez-Fonseca, C., Amils, R. and Garrett, R. A. (1995) Fine structure of the peptidyl transferase centre on 23S-like rRNAs deduced from chemical probing of antibiotic-ribosome complexes. J. Mol. Biol., 247, 224–235.

Rogers, J., Chang, A. H., von Ahsen, U., Schroeder, R. & Davies, J. (1996). Inhibition of the self-cleavage reaction of the human Hepatitis delta virus ribozyme by antibiotics. J. Mol. Biol., 259, 916–925.

Schmidt, S., Grenfell, R. L., Smith, T. V., Grasby, J. A., Mersmann, K. & Gait, M. J. (1996). Solid phase synthesis of oligoribonucleotides containing site-specific modifications. In Innovation and Perspectives in Solid Phase Synthesis and Combinatorial Libraries, ed. R. Epton, pp 11–18. Birmingham: Mayflower Scientific Ltd.

Schmidt, S., Niemann, A., Krynetskaya, N. F., Oretskaya, T. S., Metelev, V. G., Suchomlinov, V. V., Shabarova, Z. A. & Cech, D. (1992). The use of oligonucleotide probes containing 2'-deoxy-2'-fluoronucleosides for regiospecific cleavage of RNA by RNase H from Escherichia coli. Biochim Biophys Acta, 1130, 41–46.

Schnare, M. N., Damberger, S. H., Gray, M. W. and Gutell, R. R. (1996) Comprehensive comparison of structural characteristics in eukaryotic cytoplasmic large subunit (23 S-like) ribosomal RNA. J Mol Biol, 256, 701–719.

Selvin, P. R. (1995) Fluorescence resonance energy transfer. Methods Enzymol. 246, 300–335.

Slim, G., Pritchard, C., Biala, E., Asseline, U. & Gait, M. J. (1991). Synthesis of site-specifically modified oligoribonucleotides for studies of the recognition of TAR RNA by HIV-1 Tat protein and studies of hammerhead ribozymes. Nucl. Acids Res. Symp. Series, 24, 55–58.

Spahn, C. M. T. and Prescott, C. D. (1996) Throwing a spanner in the works: antibiotics and the translation apparatus. J. Mol. Med., 74, 423–439.

Spickler, C., Brunelle, M. N. and Brakier-Gingras, L. (1997) Streptomycin binds to the decoding center of 16 S ribosomal RNA. J. Mol. Biol., 273, 586–599.

Sproat, B. S., Iribarren, A. M., Garcia, R. G. & Beijer, B. (1991). New synthetic routes to synthons for 2'-O-allyloligoribonucleotide assembly. Nucl. Acids Res., 19, 733–738.

Sproat, B. S., Lamond, A. I., Beijer, B., Neuner, P. & Ryder, U. (1989). Highly efficient chemical synthesis of 2'-O-methyloligoribonucleotides and tetrabiotinylated derivatives; novel probes that are resistant to degradation by RNA or DNA specific nucleases. Nucl. Acids Res., 17, 3373–3386.

Stein, C. A., Subasinghe, C., Shinozuka, K. & Cohen, J. S. (1988). Physicochemical properties of phosphorothioate oligodeoxynucleotides. Nucl. Acids Res., 16, 3209–3221.

Stryer, L. (1978) Fluorescence energy transfer as a spectroscopic ruler. Ann. Rev. Biochem. 47, 819–846.

Sugiura, Y., Totsuka, R., Araki, M., Okuno, Y. (1997) Selective cleavages of tRNAPhe with secondary and tertiary structures by enediyne antitumor antibiotics. Bioorg. Med. Chem. 5, 1229–1234.

Sun, J. -S., Francois, J. -C., Lavery, R., Saison-Behmoaras, T., Montenay-Garestier, T., Thuong, N. T. & Hélene, C. (1988). Sequence-targeted cleavage of nucleic acids by oligo-alpha-thymidylate-phenanthroline conjugates: parallel and antiparallel double helices are formed with DNA and RNA, respectively. Biochemistry, 27, 6039–6045.

Tuschl, T., Gohlke, C., Jovin, T. M., Westhof, E. & Eckstein, F. (1994). A three-dimensional model of the hammerhead ribozyme based on fluorescence measurements. Science, 266, 785–789.

Vlassov, V. V., Gaidamakov, S. A., Zarytova, V. F., Knorre, D. G., Levina, A. S., Nikonova, A. A., Podust, L. M. & Fedorova, O. S. (1988). Sequence-specific chemical modification of double-stranded DNA with alkylating oligodeoxyribonucleotide derivatives. Gene, 72, 313–322.

von Ahsen, U. & Schroeder, R. (1991). Streptomycin inhibits splicing of group I introns by competition with the guanosine substrate. Nucl. Acids Res., 19, 2261–2265.

Wang, Y., Hamasaki, K. & Rando, R. R. (1997). Specificity of aminoglycoside binding to RNA constructs derived from the 16S rRNA decoding region and the HIV-RRE activator Region. Biochemistry, 36, 768–779.

Woodcock, J., Moazed, D., Cannon, M., Davies, J. and Noller, H. F. (1991) Interaction of antibiotics with A- and P-site-specific bases in 16S ribosomal RNA. EMBO J., 10, 3099–3103.

Yoshizawa, S., Fourmy, D. and Puglisi, J. D. (1998) Structural origins of gentamicin antibiotic action. EMBO J., 17, 6437–6448.

Zapp, M. L., Stern, S. & Green, M. R. (1993). Small molecules that selectively block RNA binding of HIV-1 Rev protein inhibit Rev function and viral production. Cell, 74, 969–978.

What is claimed is:

1. A method for determining whether a test compound binds to a target RNA, the method comprising the steps of:
   (a) contacting the test compound with a pair of indicator molecules comprising an antimicrobial labelled with a donor group or an acceptor group and the target RNA labelled with a group that is acceptor or donor, respectively, to the label on said antimicrobial, wherein the pair of indicator molecules bind to each other in an orientation that permits the donor group to come into sufficient proximity to the acceptor group to permit fluorescent resonance energy transfer and/or quenching to take place; and
   (b) measuring fluorescence of the target RNA and the antimicrobial in the presence of the test compound and comparing this value to fluorescence of a standard, thereby determining whether said test compound binds said target RNA.

2. The method of claim 1, in which the standard comprises said pair of indicator molecules in the presence or absence of test compound, said target RNA, labelled with a fluorescent donor or acceptor group, in the presence or absence of test compound, or said antimicrobial molecule, labelled with an acceptor or donor group, in the presence or absence of test compound.

3. A method for the identification of a compound that binds to a target RNA from within a plurality of test compounds, comprising the steps of the method according to claim 1 preceded by an initial step of providing a plurality of test compounds, wherein the test compound of (a) and (b) is a plurality of test compounds, and wherein the step of measuring fluorescence of the target RNA and the antimicrobial in the presence of the plurality of test compounds and comparing this value to fluorescence of a standard identifies a compound in the plurality of test compounds as binding to the target RNA.

4. The method of claim 1 or 3, wherein the pair of indicator molecules is a pre-formed indicator complex, the pre-formed indicator complex comprising a fluorescently-labelled antimicrobial bound to a fluorescently labelled target RNA in an orientation that permits the fluorescent groups present on each molecule to come into sufficient proximity to permit fluorescent resonance energy transfer to take place.

5. The method of claim 1 or 3, wherein the antimicrobial is selected from the antimicrobial classes aminoglycoside, cyclic peptide, macrolide, tetracycline, oxazolidinone, thiazole, protein, glycoprotein, alkyloid, nuclease, and N-glycosidase.

6. The method of claim 1 or 3, in which the antimicrobial binds the target RNA with a $K_d$ of between $1\times10^{-12}$ and $1\times10^{-4}$ M.

7. The method of claim 1 or 3, in which the target RNA is between 5 and about 750 nucleotides in length.

8. The method of claim 1 or 3, in which the target RNA is chemically modified.

9. The method of claim 1 or 3, in which the target RNA is a bacterial, viral, fungal, or eukaryotic RNA.

10. The method of claim 9, in which the target RNA is 16S ribosomal RNA.

11. The method of claim 10, in which the target RNA is an antimicrobial binding fragment of the 16S ribosomal RNA.

12. The method of claim 9, in which the target RNA is 23S ribosomal RNA.

13. The method of claim 12, in which the target RNA is an antimicrobial binding fragment of the 23S ribosomal RNA.

14. The method of claim 1 or 3, in which the target RNA and the labelled antimicrobial are fluorescently labelled by covalent attachment of said donor or acceptor group.

15. The method of claim 14, in which the target RNA is fluorescently labelled with said donor or acceptor group at the 3' or 5' end of a strand within the target RNA, or within the chain of the target RNA.

16. The method of claim 1 or 3, in which the antimicrobial or the target RNA molecule is adhered to a solid support.

17. The method of claim 1 or 3, in which either (i) the donor is attached to the target RNA, and the acceptor is attached to the antimicrobial, or (ii) the donor is attached to the antimicrobial, and the acceptor is attached to the target RNA.

18. The method of claim 1 or 3, in which the acceptor is able to quench fluorescence of the donor after binding of the target RNA and the antimicrobial.

19. The method of claim 1, in which the target RNA, the antimicrobial, and the test compound are mixed, and fluorescence of the mixture is compared to standards.

20. The method of claim 1, in which the test compound is first mixed with the target RNA in order to form a complex in the absence of the antimicrobial, and the antimicrobial is then added.

21. A kit for determining whether a test compound binds to a target RNA, the kit comprising (a) a target RNA labelled with a donor group or an acceptor group and (b) an antimicrobial labelled with a group that is acceptor or donor to the label on said target RNA, wherein the antimicrobial and the target RNA bind to each other in an orientation that permits the donor group to come into sufficient proximity to the acceptor group to permit fluorescent resonance energy transfer and/or quenching.

22. A method for determining the presence in a biological sample of a compound that binds to a target RNA molecule, comprising (a) contacting the sample with a pair of indicator molecules comprising an antimicrobial labelled with a donor group or an acceptor group and the target RNA labelled with a group that is acceptor or donor to the label on said antimicrobial, wherein the pair bind to each other in an orientation that permits the donor group to come into sufficient proximity to the acceptor group to permit fluorescent resonance energy transfer and/or quenching to take place; and (b) measuring fluorescence of the target RNA and the antimicrobial in said step (a) to obtain a fluorescence value and comparing this value to fluorescence of a standard, wherein a difference in said value and the fluorescence of said standard is an indication of the presence in a biological sample of a compound that binds to said target RNA.

23. The method of claim 22, said biological sample comprising a tissue or fluid from a mammal.

24. The method of claim 22, said biological sample comprising a plant extract.

25. The method of claim 22, said biological sample comprising a prokaryotic extract.

26. The method of claim 3, in which the target RNA, the antimicrobial, and the plurality of test compounds are mixed, and the fluorescence of the mixture is compared to standards.

27. The method of claim 3, in which the plurality of test compounds is first mixed with the target RNA in order to form a complex in the absence of the antimicrobial, and the antimicrobial is then added.

28. The method of claim 3, in which a complex is pre-formed between the target RNA and the antimicrobial before addition of the plurality of test compounds.

* * * * *